United States Patent
Schuch et al.

(10) Patent No.: US 11,413,334 B2
(45) Date of Patent: Aug. 16, 2022

(54) LYSIN POLYPEPTIDES ACTIVE AGAINST GRAM-NEGATIVE BACTERIA

(71) Applicant: CONTRAFECT CORPORATION, Yonkers, NY (US)

(72) Inventors: Raymond Schuch, Mountain Lakes, NJ (US); Simon Hoffenberg, Carmel, NY (US); Michael Wittekind, Bainbridge Island, WA (US)

(73) Assignee: CONTRAFECT CORPORATION, Yonkers, NY (US)

( * ) Notice: Subject to any disclaimer, the term of this patent is extended or adjusted under 35 U.S.C. 154(b) by 0 days.

(21) Appl. No.: 16/924,681

(22) Filed: Jul. 9, 2020

(65) Prior Publication Data

US 2020/0376096 A1    Dec. 3, 2020

Related U.S. Application Data

(62) Division of application No. 15/760,283, filed as application No. PCT/US2016/052338 on Sep. 16, 2016, now Pat. No. 10,744,189.

(60) Provisional application No. 62/220,212, filed on Sep. 17, 2015, provisional application No. 62/247,619, filed on Oct. 28, 2015.

(51) Int. Cl.
| | |
|---|---|
| *A61K 38/47* | (2006.01) |
| *A61K 38/12* | (2006.01) |
| *A61K 45/06* | (2006.01) |
| *A61K 9/00* | (2006.01) |
| *A61K 31/7036* | (2006.01) |
| *A61K 38/46* | (2006.01) |
| *A61K 38/16* | (2006.01) |
| *A61P 31/04* | (2006.01) |
| *C12N 9/36* | (2006.01) |

(52) U.S. Cl.
CPC ............ *A61K 38/47* (2013.01); *A61K 9/0019* (2013.01); *A61K 9/0073* (2013.01); *A61K 31/7036* (2013.01); *A61K 38/12* (2013.01); *A61K 38/162* (2013.01); *A61K 38/46* (2013.01); *A61K 45/06* (2013.01); *A61P 31/04* (2018.01); *C12N 9/2462* (2013.01); *C12Y 302/01017* (2013.01); *A61K 2121/00* (2013.01); *Y02A 50/30* (2018.01)

(58) Field of Classification Search
CPC .... A61K 38/47; A61K 9/0019; A61K 9/0073; A61K 31/7036; A61K 38/12; A61K 38/162; A61K 38/46; A61K 45/06; A61K 2121/00; A61K 38/16; A61P 31/04; C12N 9/2462; C12Y 302/01017; Y02A 50/30
See application file for complete search history.

(56) References Cited

U.S. PATENT DOCUMENTS

| | | | |
|---|---|---|---|
| 8,846,865 | B2 | 9/2014 | Briers et al. |
| 9,034,322 | B2 | 5/2015 | Fischetti et al. |
| 2013/0302306 | A1 | 11/2013 | Schuch et al. |
| 2014/0094401 | A1 | 4/2014 | Farris |
| 2014/0120074 | A1 | 5/2014 | Miller |
| 2015/0118731 | A1 | 4/2015 | Lavigne et al. |
| 2019/0290672 | A1 | 9/2019 | Wittekind |

FOREIGN PATENT DOCUMENTS

| | | |
|---|---|---|
| JP | 2010534684 A | 11/2010 |
| WO | 2012085259 A2 | 6/2012 |
| WO | 2013170015 A1 | 11/2013 |
| WO | 2014124047 A1 | 8/2014 |
| WO | 2015070911 A1 | 5/2015 |
| WO | 2015070912 A1 | 5/2015 |
| WO | 2015071436 A1 | 5/2015 |
| WO | 2015071437 A1 | 5/2015 |

OTHER PUBLICATIONS

Whisstock et al. Quaterly Reviews of Biophysics, 2003, "Prediction of protein function from protein sequence and structure", 36(3):307-340.*

Witkowski et al. Conversion of a beta-ketoacyl synthase to a malonyl decarboxylase by replacement of the active-site cysteine with glutamine, Biochemistry. Sep. 7, 1999;38(36): 11643-50.*

Vouillamoz et al. Bactericidal synergism between daptomycin and phage lysin Cpl-1 in mouse model of pneumococcal bacteraemia. International Journal of Antimicrobial Agents. 42: 416-421, 2013.*

Japanese Decision of Final Rejection issued in Japanese Patent Application No. 2018-513834, dated Jul. 20, 2021, with English language translation (9 pages).

Second Chinese Office Action issued in Chinese Patent Application No. 201680054182.8, dated Jul. 6, 2021, with English language translation (15 pages).

Lood et al., Novel Phage Lysin Capable of Killing the Multidrug-Resistant Negative Bacterium Acinetobacter baumannii in a Mouse Bacteremia Model, Antimicrob Agents Chemother 2015; 59(4): 1983-91.

Lai et al., Antibacterial activity of Acinetobacter baumannii phage pAB2 endolysin (LysAB2) against both Gram-positive and Gram-negative bacteria, Appl. Microbiol Biotechnol 2011; 90:529-539.

Briers et al., Art-175 is a Highly Efficient Antibacterial against Multidrug-Resistant Strains and Persisters of Pseudomonas aeruginosa, Antimicrob Agents Chemother. 2014; 58(7): 3774-84.

(Continued)

*Primary Examiner* — Iqbal H Chowdhury

(74) *Attorney, Agent, or Firm* — MH2 Technology Law Group LLP

(57) ABSTRACT

The present disclosure provides methods and compositions useful for the prophylactic and therapeutic amelioration and treatment of infections caused by Gram-negative bacteria, including *Pseudomonas aeruginosa*. The disclosure further provides compositions and methods of incorporating and utilizing lysin polypeptides of the present disclosure for augmenting the efficacy of antibiotics generally suitable for the treatment of Gram-negative bacterial infection.

13 Claims, 9 Drawing Sheets

Specification includes a Sequence Listing.

(56) References Cited

OTHER PUBLICATIONS

Briers et al., Engineered Endolysin-Based 'Artilysins' to Combat Multidrug-Resistant Gram-Negative Pathogens, MBio. 2014; 4:e01379-14.
Deslouches, B. et al., Activity of the De Novo Engineered Antimicrobial Peptide WLBU2 against Pseudomonas aeruginosa in Human Serum and Whole Blood: Implications for Systemic Applications, Antimicrobial Agents & Chemotherapy 2005; 49(8):3208-3216.
Brogden N. et al, Will new generations of modified antimicrobial peptides improve their potential as pharmaceuticals, Int J Antimicrob Agents. 2011; 38(3): 217-225.
Svenson, J. et al, Albumin binding of Short Cationic Antimicrobial Micropeptides and its influence on the in Vitro Bactericidal Effect, J. Med. Chem. 2007; 50 (14):3334-3339.
Fischetti, V., Bacteriophage lysins as effective antibacterials, Curr Opin Microbiol. 2008; 11(5): 393-400.
Loeffler et al.,Synergistic Lethal Effect of a Combination of Phage Lytic Enzymes with Different Activities on Penicillin-Sensitive and -Resistant *Streptococcus pneumoniae* Strains, Antimicrob Agents Chemother. 2003; 47(1): 375-377.
English-language translation of the Israeli Office Action issued in Israeli Patent Application No. 258122 dated Feb. 27, 2019, pp. 1-3.
English-language translation of the Russian Office Action issued in Russian Patent Application No. 2018107245/10(011078) dated Oct. 23, 2019, pp. 1-7.
Uchiyama et al., Characteristics of a novel Pseudomonas aeruginosa bacteriophage, PAJU2, which is genetically related to bacteriophage D3, Virus Research 139 (2009), 131-134.
Russian Office Action issued in corresponding Russian Application No. 2018107245/10 dated May 27, 2019, pp. 1-13, with English translation.
Severin, E.S. (Editor), Biokhimika: Textbook—2nd revised ed.—Moskva: GEOTAR-MED, 2004, (Series "XXI vek"), p. 9.
Pakula, A.A. et al., Genetic analysis of protein stability and function, Annu. Rev. Genet., vol. 23 (1989) pp. 289-310.
GenBank Database: AGO38582.1, Jan. 31, 2014, pp. 1-2.
NCBI Database Reference Sequence: YP_001293410.1, Jun. 18, 2007, p. 1.
UniProtKB Database: B5WZU3, Nov. 25, 2008, pp. 1-5.
GenBank Database: EDG23390.1, Apr. 6, 2007, pp. 1-2.
NCBI Database Reference Sequence: WP_014102102.1, May 18, 2013, p. 1.
Andreu, D. et al., Identification of an anti-mycobacterial domain in NK-lysin and granulysin, Biochem. J., 1999, 344, pp. 845-849.
Anonymous, putative endolysin [Pseudomonas phage PAJU2], Feb. 18, 2009, abstract at https://www.ncbi.nim.nih.gov/protein/YP_00284361.1.
Briers, Y. et al., Use of bacteriophase endolysin EL188 and outer membrane permeabilizers against Pseudomonas aeruginosa, J. of App. Microbiol. 2011, 110, pp. 778-785.
Farris, M.H. et al., Mitrecin A, an endolysin-like bacteriolytic enzyme from a newly isolated soil streptomycete, Letters in App. Microbiol. 2014, 58, pp. 493-502.
International Search Report for PCT/US2016/052338, dated Mar. 29, 2017.
Lukacik, P. et al., Structural engineering of a hage lysin that targets Gram-negative pathogens, PNAS, Jun. 19, 2012, vol. 102, No. 25, pp. 9857-9862.
Lukacik, P. et al., Using a bacteriocin structure to engineer a phage lysin that targets Yersinia pestis, Biochem. So. Trans. 2012, 40, pp. 1503-1506.
Morita, M. et al., Functional analysis of antibacterial activity of Bacilus amyloliquefaciens phage endolysin against Gram-negative bacteria, FEBS Letters, 2001, 500, pp. 56-59.
Pastagia, M. et al., Lysins: the arrival of pathogen-directed anti-infectives, J. Med. Microbiol. 2013, 62, pp. 1506-1516.
Wang, et al., Genomic insights into an obligate epibiotic bacterial predator: Micavibrio aeruginosavorus ARL-13, BMC Genomics, 2011, 12(453), pp. 1-12.

Golodne, D., Brazilian preliminary office action issued in Brazilian Patent Application No. BR112018005318-0 published in Brazilian Industrial Property Journal No. 2601 dated Nov. 10, 2020, with English language translation (7 pages).
Vouillamoz J, et al. "Bactericidal synergism between daptomycin and the phage lysin Cpl-1 in a mouse model of pneumococcal bacteraemia." Int J Antimicrob Agents. 2013, 42(5):416-421.
Silverman JA, et al. "Inhibition of daptomycin by pulmonary surfactant: in vitro modeling and clinical impact." J Infect Dis. 2005, 191(12):2149-2152.
Schuch R,"Combination therapy with lysin CF-301 and antibiotic is superior to antibiotic alone for treating methicillin-resistant *Staphylococcus aureus*-induced murine bacteremia. " J Infect Dis. 2014; 209(9):1469-1478.
Nguyen KT, et al. "Genetically engineered lipopeptide antibiotics related to A54145 and daptomycin with improved properties. Antimicrob Agents Chemother." Apr. 2010;54(4):1404-1413.
Van't Veen A, et al. "Influence of pulmonary surfactant on in vitro bactericidal activities of amoxicillin, ceftazidime, and tobramycin." Antimicrob Agents Chemother 1995 ;39(2):329-333.
Schwameis R, et al. "Effect of pulmonary surfactant on antimicrobial activity in vitro." Antimicrob Agents Chemother. 2013, 57(10):5151-5154.
EESR issued in European Patent Application No. 16778940.3 dated Oct. 21, 2020 (3 pages).
Becker, S.C. et al., The phage K lytic enzyme LysK and lysostaphin act synergistically to kill MRSA, FEMS Microbiol. Lett. 2008; 287:185-191.
Cheng, Q. et al., Removal of Group B Streptococci Colonizing the Vagina and Oropharynx of Mice with a Bacteriophage Lytic Enzyme, Antimicrob. Agents Chemother. 2005; 49(1):111-117.
Fenton, M. et al., Recombinant bacteriophage lysins as antibacterials, Bioengineered Bugs 2010; 1(1):9-16.
Garcia, J.L. et al., Cloning, Purification, and Biochemical Characterization of the Pneumococcal Bacteriophage Cp-1 Lysin, J. Virol. 1987; 61(8):2573-2580.
GenBank AFN38929.1, Mar. 28, 2014, available at https://www.ncbi.nlm.nih.gov/protein/AFN38929.1, pp. 1-3.
GenBank Database: AB254389.1, Oct. 5, 2006, available at https://www.ncbi.nlm.nih.gov/nuccore/ab254389.1, pp. 1-4.
GenBank KJ740396.1, Apr. 1, 2005, available at https://www.ncbi.nlm.nih.gov/nuccore/kj740396.1, pp. 1-2.
Gilmer, D.B. et al., Novel Bacteriophage Lysin with Broad Lytic Activity Protects against Mixed Infection by *Streptococcus pyogenes* and Methicillin-Resistant *Staphylococcus aureus*, Antimicrob. Agents Chemother. 2013; 57(6):2743-2750.
Goerke, J., Pulmonary surfactant: functions and molecular composition, Biochim et Biophys. Acta 1998; 1408:79-89.
Brazilian preliminary office action issued in Brazilian Patent Application No. BR112018005316-3 dated Oct. 27, 2020, with English language translation (6 pages).
Hermann et al. Colistin-Tobramycin Combinations Are Superior to Monotherapy Concerning the Killing of Biofilm Pseudomonas aeruginosa. JID 2010:202: 1585-1592.
Chinese office action issued in Chinese Patent Application No. 201680054182.8 dated Nov. 9, 2020, with English language translation (20 pages).
International Search Report for PCT/US2016/052348 dated Mar. 28, 2017.
Jung, D. et al., Structural Transitions as Determinants of the Action of the Calcium-Dependent Antibiotic Daptomycin, Chem. Biol. 2004; 11:949-957.
English-language translation of Israeli Office Action issued in Israeli Patent Application No. 258123 dated Feb. 27, 2019, pp. 1-3.
Office Action issued in Israeli Patent Application No. 258123 dated Jul. 30, 2020 with English language translation (8 pages).
Lakey, J.H. et al., Fluorescence Indicates a Calcium-Dependent Interaction between the Lipopeptide Antibiotic LY146032 and Phospholipid Membranes, Biochemistry 1988; 27:4639-4645.
Madsen, J. et al., Expression and Localization of Lung Surfactant Protein A in Human Tissues, Am. J. Respir. Cell Mol. Biol 2003; 29(5):591-597.

(56) References Cited

OTHER PUBLICATIONS

Martin, A.C. et al., Nucleotide Sequence and Transcription of the Left Early Region of Streptococcus pneumoniae Bacteriophage Cp-1 Coding for the Terminal Protein and the DNA Polymerase, Virology 1995; 221:21-32.
McGowan, S. et al., X-ray crystal structure of the streptococcal specific phage lysin PlyC, Proc. Natl. Acad. Sci. USA 2012; 109(31):12752-12757.
Nelson, D. et al., PlyC: A multimeric bacteriophage lysin, Proc. Natl. Acad. Sci. USA 2006; 103(28):10765-10770.
Oeschlin, F. et al., In Vitro Characterization of PlySK1249, a Novel Phage Lysin, and Assessment of its Antibacterial Activity in a Mouse Model of Streptococcus agalactiae Bacteremia, Antimicrob. Agents Chemother. 2013; 57(12):6276-623.
Pritchard, D.G. et al., LamdaSa1 and LambdaSa2 Prophage Lysins of Streptococcus agalactiae, Appl. Environmental Microbiol. 2007; 73(22):7150-7154.
Office Action issued in Japanese Patent Application No. 2018-513834 dated Sep. 15, 2020 with English language translation (14 pages).
English-language translation of Russian Office Action issued in corresponding Russian Patent Application No. 2018107249/04 dated Jan. 10, 2020, pp. 1-8.
Varea, J. et al., Structural and Thermodynamic Characterization of Pal, a Phage Natural Chimeric Lysin Active against Pneumococci, J. Biol. Chem. 2004; 279(42):43697-43707.
Wittekind, Michael et al., "Cell wall hydrolases and antibiotics: exploiting synergy to create efficacious new antimicrobial treatments", Current Opinion in Microbiology, 2016, 33, pp. 18-24.
Yang, H. et al., Novel Chimeric Lysin with High-Level Antimicrobial Activity against Methicillin-Resistant Staphylococcus aureus In Vitro and In Vivo, Antimicrob. Agents Chemother. 2014; 58(1):536-542.
Lood, R. et al., A Highly Active and Negatively Charged Streptococcus pyogenes Lysin with a Rare D-Alanyl-L-Alanine Endopeptidase Activity Protects Mice against Streptococcal Bacteremia, Antimicrob. Agents Chemother. 2014;58(6):3073-3084.
First Examination Report issued in Indian Patent Application No. 201817008090 dated May 24, 2021, with English language translation (5 pages).
Huning, Z., Chinese Office Action issued in Chinese Patent Application No. 201680054495.3 dated May 8, 2021 with English language translation (26 pages).
GenBank Database: AEP08879.1, Jan. 31, 2014. pp. 1-2.
Office Action issued in corresponding Japanese Patent Application No. 2018-513835 dated Jul. 8, 2020 with English language translation (12 pages).
Shibahara, N., Japanese Office Action issued in corresponding Japanese Patent Application No. 2018-513835 dated Mar. 16, 2021 with English language translation (6 pages).
Huning, Z., Chinese Office Action issued in Chinese Patent Application No. 201680054495.3, dated Dec. 10, 2020, with English language translation (25 pages).
Australian Examination Report issued in Australian Patent Application No. 2016324298, dated Sep. 22, 2021 (5 pages).
Mexican Office Action issued in Mexican Patent Application No. MX/a/2018/003101, dated Oct. 11, 2021 with English-language translation (13 pages).

\* cited by examiner

MTYTLSKRSL DNLKGVHPDL VAVVHRAIQL TPVDFAVIEG
LRSVSRQKEL VAAGASKTMN SRHLTGHAVD LAAYVNGIRW
DWPLYDAIAV AVKAAAKELG VAIVWGGDWT TFKDGPHFEL
DRSKYR (SEQ ID NO: 1)

FIG. 1A

ATGACATATACACCCTGAGCAAAAGAAGCCTGGATAACCTAAAAGGCGTTCATCCCGATCTCGGTTGCCGTTG
TCCATCGCGCCATCCAGCTTACACCGGTTGATTTCGCGGTGATCGAAGGCCTGCGCGTATCCCGGCCAA
AAGGAACTGGTGGCCGCGGGCCAGCAAGACCATGAACAGCCGACACTGAAGGCCATGCGGTTGA
TCTAGCCGCTTACGTCAATGGGATTCGGATCAAGACGCCATCGTGTGGGGCGGTGACTGTGGGCTGTGAAA
GCCGCAGCAAAGGAATTGGGTGTGGCCATCGTGTGGGGCGGTGACTGTGGGCTGTGAAA
GCACTTTGAACTGGGAGCAAATACAGATGA (SEQ ID NO: 11)

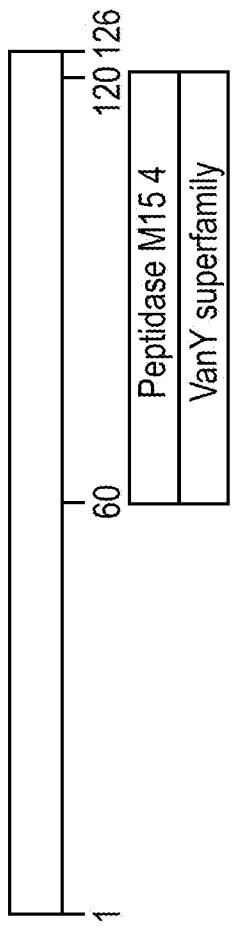

FIG. 1B

```
GN37            ------------MT--YTLSKRSLDNLKGVHPDLVAVVHRAIQLTPVDFAVIEGLRSVSRQKE  49  (SEQ ID NO: 18)
AGJ50592.1      ------------MS--FGLSQRSRERLKGVHPDLVAVVEAAIRLTPVDFMITEGLRTPARQAE  49  (SEQ ID NO: 1)
WP_001117823.1  ------------MPGKFRFSRRSEKNLEGVKPQLVAVVRRALELTEVDFGITEGLRSKYRQKQ  51  (SEQ ID NO: 19)
NP_543082.1     ------------MSGKFRFSRRSEKNLEGVKPQLVAVVRRALELTEVDFGITEGLRTKERQKQ  51  (SEQ ID NO: 20)
CAJ28446.1      MEVQPTIEEVSMGFKLGSRSLQRLQGVHPDLVKVVKRAIEISPVDFTVTEGLRTLERQKE    60  (SEQ ID NO: 21)
                              :    :   :**  **:*::**:*: ** .:**. * ***  :

GN37            LVAAGASKTMNSRHLTGHAVDLAAYVNG-IRWDWPLYDAIAVAAKELGVAIVWGGD       108  (SEQ ID NO: 18)
AGJ50592.1      LVRAGASRTLNSRHLTGHAVDVAAWIDGEVRWDWPLYPRIAEEAFKAAAKDRDVALIWGGD   109  (SEQ ID NO: 1)
WP_001117823.1  LVAAGKSQTMNSRHLTGDAVDVVAYIGSQVSWDWPLYEKIAQAFKQAAAELGTAIEWGGD   111  (SEQ ID NO: 19)
NP_543082.1     LVAEGKSQTMNSRHLTGDAVDVVAYIGSQVSWDWPLYEKIAQAFKQAAAELGTAIEWGGD   111  (SEQ ID NO: 20)
CAJ28446.1      LFAKGASKTMRSRHLTGHAVDISPLVDGKVSWDMKYYYPMADAMKQAAKELNIPVEWGGD  120  (SEQ ID NO: 21)
                *  * *::*:.*****..**:  :::   :  *** :  :*. :  **:*: :::****

GN37            WTTFKDGPHFELDRSKYR  126  (SEQ ID NO: 1)
AGJ50592.1      WPRLRDGPHFELDRRGYP  127  (SEQ ID NO: 18)
WP_001117823.1  WKTLKDGPHFQLKR----  125  (SEQ ID NO: 19)
NP_543082.1     WKTLKDGPHFQLKW----  125  (SEQ ID NO: 20)
CAJ28446.1      WKTFKDGPHFQLPYGVYK  138  (SEQ ID NO: 21)
                *  ::*****:*
```

FIG. 1C

GN2: MKISLEGLSLIKKFEGCKLEAYKCSAGVWTIGYHTAGVKEGDVCTQEEAEKLLRGDIFKEEYVQDSVKVDLLDQSQFDALVAWTFNLGPGN LRSSTMLKKLNNGEYESVPFEMRRWNKAGGKTLDGLIRRQAFSLLFESKEWHQV (SEQ ID NO: 2)

GN4: ATGAAAAATTAGTTGAGGGATTATCTCTCATCAAAAATTTGAGGGTTGTAAACTAGAAGCATACAAAGTTCTGCAGGAGTGTGGACTATAGTTATGGTCATCTGC
AGGTGTAAAAGAAGCTGATGTTTGCACACAAGAGGAAGCTGAAAAATTATTAAGAGAGAGATATCTTTAAATTTGAAGAGTAGTGTAAAGGTTGATTTA
GACCAAAGTCAATTTGACGCATTAGTTGCATGGACATTTAATTTAGGCCCAGTAATTTAAGAAGTTCAACCATGTTGAAAAAATTAAATAATGGAGAGTAATGAATCTGTT
CCTTTCGAAATGAGAAGGTGAATAAAGCAGGTGTAAAACTTAGAGTGTTTAATCAGAAGACGCCAAGCAGAATCATTATTATTTGAAAGTAAAGAGTGGCATCAAG
TATAA (SEQ ID NO: 12)

ATGGGTACATCCAAGGAGGCATCGACCTCATCAAATCCTTCGAGGGCCCTGCGCGCTTGTCCGCTTACCAGAGACTCGGTGGGTGTCTGGACCATAGTTACGGCACCACTCG
GGGCGTCACCCGCTACATGACGATCACCGTCGAGCAGCCGGATGCTGTCAGCGACATTCAGCGCTTCAGCACGCTGCTCCACGCTGCGTCGAACAAGGGTGACTACCAGGG
GAACCAGAACCAGTGGATGCCCTGATGAGCTTCGTCGTATACGAGCTGGCGCGCAATCTGGGGCCAATCTGGCGTCCAGCCTGCTCCACGCTGCTCGTGAACAAGGGTGACTACCAGGG
AGCAGGCGGACCAGTCCCGCTGGGTAATGCGGGCGGTTGAATGCCGGGTGAATGCGGGCGGTTGAAGGTCGGTGATTGGTCTCGCTTGTTCCTGAGCGCACTATGTG
A (SEQ ID NO: 13)

GN14: MNNELPWVAEARKYIGLREDTSKTSHNPKLLAMLDRMGEFSNESRAWWHDDETPWCGLFVGYCLGVAGRYVVREWYRARAWEAPQL
TKLDRPAYGALVTFTRSGGGHVGFIVGKDARGNLMVLGGNQSNAVSIAPFAVSRVTGYFWPSFWRNKTAVKSVPFEERYSLPLLKSNGELS
TNEA (SEQ ID NO: 4)

ATGAATAACGAACTTCCTTGGGTAGCCGAAGCCCGAAAGTATATCGGCTTCGCGGAAGACACTTCGAAGACTTCGCATAACCGAAGACTTCTTGCCATGCTTGACCGGCAT
GGGCGAATTTTCCAACGAATCCCGCGCTTGGTGGCACGACGAGAAACGCCTTGCGGTGCACTGTTCGTCGGCTATTGCTTGGTGCACGGCCTACGCGCTCGTCCGC
GAATGGTACAGGCGGCGCATGGAAGCCCCAGCTTGACGGCGGCTTGACCTTCACGCGAGCTGCACCGCGTAATCGGAGTCGAATGCGCGTAAGTATCGCACGGTTGCGCAGTCGGT
TTATTGTGGGCAAGGATGCGCGCGGCGAAATCTTATGGTTCTTGGCGGTCGCGAAATCAGTCGAAGCCCGTAAGTATGCGAACGCGTCGCAGTATCCCGCAGTATCCCGGTATCCCGGTAAGTATCGCAGTATTTCTG
GCCGTGCTTCTGGCGAAACCGACAAGACCGCAGTTAAAAGCGTTCCGTTTGAAGAAGAACGTTATTCGCTCGCGCTGTTGAAGTCGAATGAAGACGGTTATTCGCGTTGAAGTCGAAGCTAA
(SEQ ID NO: 14)

FIG. 2A

GN43: MKRTTLNLELESNTDRLLQEKDDLLPQSVTNSSDEGTPFAQVEGASDDNTAEQDSDKPGASVADADTKPVDPEMKTITVASGDTLSTVFTK
AGLSTSAMHDMLTSSKDAKRFTHLKVGQEVKLKLDPKGELQALRVKQSELETIGLDKTDKGYSFKREKAQIDLHTAYAHGRITSSLFVAGRN
AGLPYNLVTSLSNIFGYDIDFALDLREGDEFDVIYEQHKVNGKQVATGNILAARFVNRGKTYTAVRYTNKQGNTSYRADGSSMRKAFIRTP
VDFARISSRFSLGRRHPIILNKIRAHKGVDYAAPIGTPIKATGDGKILEAGRKGGYGNAVIQHGQRYRTIYGHMSRFAKGIRAGTSVKQQII
GYVGMTGLATGPHLHYEFQINGRHVDPLSAKLPMADPLGGADRKRFMAQTQPMIARMDQEKKTLLALNKQR (SEQ ID NO: 5)

ATGAAGAGGACCACGCTGAATCTGGAGCTTGAAAGCAACACCGATCGCCTCCTCCAGGAGAAAGAGGACCTCCTGCCGCAATGTCAGCGACGAAGGCAGCCTTTCGCTC
AGTTAGAAGGCGGCCTCCGACGACAACACCGCCGAGCAACTGGACAAGCCCTTCACCAAGCCGGATCGTAGCCGACACGTCCTTCACCAAGCCGGATCGTGAAGGTCGGCCAGGAGGT
GTGAAGCTGATACGCTGTCGACCGTATTCCAGGAGGCTGCCTCCACCTGCGAGTCAAGCTACTGCGGACGACGAACTCGGCGACGAGCTCAAGGCTACTCCTTCAAACGGTCAGGAGGCCC
CAAGCTCAAGCTGACCCCAAAGGAGAGCTCAGGGACTGCAGCCTGAGTCGCTGTTGCCGGTCGATACGCCTCGGCCATGCCCTATGGGCCGATACCCCGACTTCGCCCTCGATCTGCGTGAAGCCGACGAGTTCGACGTCAACACAAGCCCGAAGCAGCACACCGAAGGACGATCTCCGCGGCACGGCGATCGAGCGCGCGCCGAAGTCGCCAAGCACAGCGGCACCCGACACCGCCCGAAGCCCGAAGGAGCGCGTGAACTGCCACGTCGGGTGATTTCGCCGTATCAGCTCCGACTTGCCCTCGATCTGCGTGAAGCCGACGAGTTCGACGTCAACACAAGCCCGAAGCAGCACACCGAAGGACGATCTCCGCGGCACGGCGATCGAGCGCGCGCCGAAGTCGCCAAGCACAGCGGCACCCGACACCGCCCGAAGCCCGAAGGAGCGCGTGAACTGCCACGTCGGGTGATTTCGCCGTATCAGCTC
AAGACCTACACCGCGTGGCTATACCAACAGGGCAATACGCGTCGACGAGTTCGAATAACAAGATCCGGACAGATCCGAACAAGGCTGACAACAAGCGCCAACTGGAGCAACATGCCCATGCGCGCAAGGCTATCGCCAAGGGCTATCGCCAAGGGTATCCGCGCGGTACCAGCGTGAAG
GCCGGACGCAAGGGCGTACGGCAACGTCCGACCACCGCAACGCCCAGCAGCAGCAGGACACATCCAGCAGCCACTACGGACGCCTATCGGAGACATCGGGCAAAGACATGAGCCCTTCGCCAAGGGTATGCCGCGCGGTACCAGCGTGAAG
CAGGGCCCAGAGATCATGGCGGTTAGGACGATCGCCAAGGCCTTCATGGCGCAGATGCGCCAGCCCGATGATCGCGCGCCCATGATCGCGCGCGCCATGGATCAGGAGAAGAAAACCCTGCTGGCCCTGAACAAGCAGCGCTGA (SEQ ID NO: 15)

FIG. 2B

PGN4 (39 aa): NKGDYQGAADQFPRWVNAGGKRLDGLVKRRASQSRESQC (SEQ ID NO: 6)

FGN4-1 (42 aa): NKGDYQGAADQFPRWVNAGGKRLDGLVKRRAAERALFLEPLS (SEQ ID NO: 7)

FGN4-2 (31 aa): NKGDYQGAADQFPRWVNAGGKRLDGLVKRRA (SEQ ID NO: 8)

FGN4-3 (31 aa): NKGDYQGAADQFPRWVNAGGKRLDGLVKRRK (SEQ ID NO: 9)

FGN4-4 (43 aa): NKGDYQGAADQFPRWVNAGGKRLDGLVKRRAAERALFLEPLSC (SEQ ID NO: 10)

FIG. 5

LYSIN POLYPEPTIDES ACTIVE AGAINST GRAM-NEGATIVE BACTERIA

STATEMENT OF RELATED APPLICATIONS

This patent application is a divisional application of U.S. patent application Ser. No. 15/760,283 (allowed), filed Mar. 15, 2018, which is a national phase application of International Patent Application No. PCT/US2016/052338, filed Sep. 16, 2016, and which claims the priority of U.S. Provisional Patent Application 62/220,212 filed Sep. 17, 2015, and U.S. Provisional Patent Application 62/247,619 filed Oct. 28, 2015; the contents of these applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 9, 2020, is named 0341.0018-01_ST25.txt and is 22,391 bytes in size.

BACKGROUND OF THE DISCLOSURE

Technical Field

The present disclosure relates generally to the prophylaxis and treatment of infections caused by the Gram-negative bacteria. More specifically, the disclosure relates to agents and compositions capable of preventing and/or inhibiting growth of Gram-negative bacteria.

Description of the Related Art

Gram-negative pathogens pose a significant threat with evolving resistance to nearly all drugs previously considered for treatment. Of particular concern are healthcare-associated infections involving the Gram-negative pathogen *Pseudomonas aeruginosa* which can develop resistance to numerous antimicrobial agents such as antibiotics, including but not limited to ciprofloxacin, levofloxacin, gentamicin, cefepime, imipenem, meropenem (Lister et al. *Clin Microbiol Rev.* 4: 582-610 (2009)). In addition to resistance to individual drugs, the emerging and increasing prevalence of multidrug-resistant strains combined with the paucity of new antibiotics is cause for alarm. Novel and effective treatments for Gram-negative infections are clearly needed to address the threat from multi-drug resistance. One very promising approach is based on the use of bacterial peptidoglycan hydrolases, or PGHs, including lysins, autolysins, and some bacteriocins to degrade a major structural component of the bacterial cell wall (i.e., peptidoglycan). PGHs include glucosaminidases and muramidases (i.e., lysozymes), which cleave the sugar backbone of peptidoglycan, endopeptidases, which cleave the stem-peptide or cross-bridge, or L-alanine amidases, which cleave the amide bond connecting the sugar and peptide moieties (Bush K., *Rec Sci Tech.* (1):43-56 (2012); Reith J. et al. *Appl Microbiol Biotechnol.* (1):1-11 (2011)).

Work over the past 14 years has shown that PGHs can be recombinantly expressed, purified, and added exogenously to sensitive bacteria for rapid bacteriolysis. This "lysis from without" phenomenon is the basis of an effective antibacterial strategy currently under development for several Gram-positive bacterial pathogens. However, compared to Gram-positive bacteria, the use of lysins for treatment of Gram-negative bacterial infections has been limited due to the existence of the additional membrane layer within the bacterial cell wall. This additional layer, known as the outer membrane (OM), hinders the access of lysins to their peptidoglycan substrates in the cell wall. Nonetheless, recently, several PGHs from Gram-negative bacteria and associated bacteriophages have been reported with some innate ability to kill Gram-negative bacteria (Lood et al., *Antimicrob Agents Chemother,* 4: 1983-91, (2015)). For bactericidal Gram-negative lysins, the activity may be dependent on positively charged (and amphipathic) N- and C-terminal alpha helical domains in the native sequences, which enable binding to the anionic OM and effect translocation into the subjacent peptidoglycan (Lai et al. *Microbiol Biotechnol,* 90:529-539 (2011)). Recently, researchers have used this knowledge to create "artilysins," engineered lysins with added cationic peptides for antibacterial activity against Gram-negative *Pseudomonas aeruginosa* and *Acinetobacter baumannii* (Briers et al., *Antimicrob Agents Chemother.* 58(7): 3774-84 (2014)). These artilysins consist of positively charged PGHs (active against Gram-positive bacteria) fused to exogenously-derived cationic peptides that are not related to or derived from lysins (Briers et al., *Antimicrob Agents Chemother.* 58(7): 3774-84 (2014); Briers et al. *MBio.* 4:e01379-14 (2014); U.S. Pat. No. 8,846,865).

The citation of references herein shall not be construed as an admission that such references are relevant or that they constitute prior art to the present disclosure.

SUMMARY OF THE DISCLOSURE

In one aspect, the present disclosure provides a pharmaceutical composition comprising an effective amount of an isolated lysin polypeptide comprising an amino acid sequence having at least 80% or at least 85% or at least 90% or at least 95% identity to a polypeptide sequence selected from the group consisting of SEQ ID NO: 1-SEQ ID NO: 10, or a fragment thereof having lysin activity, wherein the lysin polypeptide inhibits the growth, or reduces the population, or kills *P. aeruginosa* and optionally at least one other species of Gram-negative bacteria; and a pharmaceutically acceptable carrier.

In some embodiments, lysin polypeptide or fragment is present in an amount effective to inhibit the growth, to reduce the population, or to kill *P. aeruginosa* and optionally at least one other species of Gram-negative bacteria.

In some embodiments, the pharmaceutical composition is a solution, a suspension, an emulsion, an inhalable powder, an aerosol, or a spray.

In some embodiments, the pharmaceutical composition further comprises one or more antibiotics suitable for the treatment of Gram-negative bacteria.

In another aspect, the disclosure provides a vector comprising an isolated polynucleotide comprising a nucleic acid molecule that encodes a lysin polypeptide comprising an amino acid sequence having at least 80% or at least 85% or at least 90% or at least 95% sequence identity to a sequence selected from the group consisting of SEQ ID NO: 1-SEQ ID NO: 10, or a fragment thereof having lysin activity, wherein the encoded lysin polypeptide inhibits the growth, or reduces the population, or kills *P. aeruginosa* and optionally at least one other species of Gram-negative bacteriaor a complementary sequence of said polynucleotide.

In another aspect, the disclosure provides a recombinant expression vector comprising a nucleic acid encoding a lysin polypeptide comprising an amino acid sequence at least 80% or at least 85% or at least 90% or at least 95% identical to a sequence selected from the group consisting of SEQ ID NO: 1-SEQ ID NO: 10, or a fragment thereof having lysin activity, wherein the encoded lysin polypeptide has the property of inhibiting the growth, or reducing the population, or killing *P. aeruginosa* and optionally at least one other species of Gram-negative bacteria, the nucleic acid being operatively linked to a heterologous promoter.

In some embodiments, the nucleic acid sequence is a cDNA sequence.

In yet another aspect, the disclosure provides an isolated polynucleotide comprising a nucleic acid molecule that encodes a lysin polypeptide comprising an amino acid sequence having at least 80% or at least 85% or at least 90% or at least 95% sequence identity to a sequence selected from the group consisting of SEQ ID NO: 1-SEQ ID NO: 10, or a fragment thereof having lysin activity, wherein the encoded lysin polypeptide inhibits the growth, or reduces the population, or kills *P. aeruginosa* and optionally at least one other species of Gram-negative bacteria.

In some embodiments, the polynucleotide is cDNA.

In another aspect, the disclosure provides a method of inhibiting the growth, or reducing the population, or killing of at least one species of Gram-negative bacteria, the method comprising contacting the bacteria with a composition containing an effective amount of a lysin polypeptide comprising an amino acid sequence at least 80% identical to polypeptide sequence selected from the group consisting of SEQ ID NO: 1-SEQ ID NO: 10, or active fragments thereof, wherein the lysin polypeptide has the property of inhibiting the growth, or reducing the population, or killing *P. aeruginosa* and optionally at least one other species of Gram-negative bacteria.

In a related aspect, the disclosure provides a method of treating a bacterial infection caused by a Gram-negative bacteria selected from the group consisting of *P. aeruginosa* and optionally one or more additional species of Gram-negative bacteria, comprising administering to a subject diagnosed with, at risk for, or exhibiting symptoms of a bacterial infection, a composition containing an effective amount of a lysin polypeptide comprising an amino acid sequence at least 80% identical to a polypeptide sequence selected from the group consisting of SEQ ID NO: 1-SEQ ID NO: 10, or an active fragment thereof, wherein the lysin polypeptide has the property of inhibiting the growth, or reducing the population, or killing *P. aeruginosa* and optionally at least one other species of Gram-negative bacteria.

In another aspect, the disclosure provides a method of treating a topical or systemic pathogenic bacterial infection caused by a Gram-negative bacteria selected from the group consisting of *P. aeruginosa* and optionally one or more additional species of Gram-negative bacteria in a subject, comprising administering to a subject composition containing an effective amount of a lysin polypeptide comprising an amino acid sequence at least 80% identical to polypeptide sequence selected from the group consisting of SEQ ID NO: 1-SEQ ID NO: 15, wherein the polypeptide or peptide has the property of inhibiting the growth, or reducing the population, or killing *P. aeruginosa* and optionally at least one other Gram-negative bacteria.

In yet another aspect, the disclosure provides a method of preventing or treating a bacterial infection comprising co-administering to a subject diagnosed with, at risk for, or exhibiting symptoms of a bacterial infection, a combination of a first effective amount of the composition containing an effective amount of lysin polypeptide comprising amino acid sequence at least 80%, or at least 85%, or at least 90%, or at least 95% identical to polypeptide sequence selected from the group consisting of SEQ ID NO: 1-SEQ ID NO: 10, or fragments thereof, and a second effective amount of an antibiotic suitable for the treatment of Gram-negative bacterial infection.

In some embodiments, Gram-negative bacteria is selected from the group consisting of *Pseudomonas aeruginosa*, *Klebsiella* spp., *Enterobacter* spp., *Escherichia coli*, *Citrobacter freundii*, *Salmonella typhimurium*, *Yersinia pestis*, and *Franciscella tulerensis*.

In some embodiments, lysin polypeptide amino acid sequence is at least 85% or at least 90% identical to a sequence selected from the group consisting of SEQ ID NO: 1-SEQ ID NO: 10, or a fragment thereof having lysin activity.

In some embodiments, the lysin polypeptide amino acid sequence is at least 95% identical to a sequence selected from the group consisting of SEQ ID NO: 1-SEQ ID NO: 10, or a fragment thereof having lysin activity.

In some embodiments, the Gram-negative bacterial infection is an infection caused by *Pseudomonas aeruginosa*.

In some embodiments, the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

In another aspect, the disclosure provides a method for augmenting the efficacy of an antibiotic suitable for the treatment of Gram-negative bacterial infection, comprising co-administering the antibiotic in combination with one or more lysin polypeptides comprising an amino acid sequence at least 80% identical to a polypeptide sequence selected from the group consisting of SEQ ID NO: 1-SEQ ID NO: 10, or an active fragment thereof, wherein administration of the combination is more effective in inhibiting the growth, or reducing the population, or killing the Gram-negative bacteria than administration of either the antibiotic or the lysin polypeptide or active fragment thereof individually.

In some embodiments, the lysin polypeptide amino acid sequence is at least 90% identical to a sequence selected from the group consisting of SEQ ID NO: 1-SEQ ID NO: 10, or a fragment thereof having lysin activity.

In some embodiments, the lysin polypeptide amino acid sequence is at least 95% identical to a sequence selected from the group consisting of SEQ ID NO: 1-SEQ ID NO: 10, or a fragment thereof having lysin activity.

In another aspect, an isolated lysin polypeptide, comprising an amino acid sequence having at least 80% or at least 85% or at least 90% or at least 95% identity to a polypeptide sequence selected from the group consisting of SEQ ID NO: 1-SEQ ID NO: 10, or a fragment thereof having lysin activity, wherein the lysin polypeptide inhibits the growth, or reduces the population, or kills *P. aeruginosa* and, optionally, at least one other species of Gram-negative bacteria.

BRIEF DESCRIPTION OF THE DRAWINGS

FIG. 1 provides the nucleotide and amino acid sequences of lysin polypeptide GN37 reported in the present disclosure. FIG. 1A (left) is an amino acid sequence of GN37. FIG. 1A (right) is a nucleotide sequence of GN37. FIG. 1B is a schematic of GN37, indicating that GN37 is a member of peptidase M15_4 family of PGHs with DD- and DL-carboxypeptidase activities (including members of the VanY superfamily) FIG. 1C shows a multiple sequence alignment comparing GN37 to a Gram-positive partial homolog (*Streptomyces*, GenBank sequence AGJ50592.1) and to putative or confirmed endolysins from other Gram-negative pathogens including *E. coli* (GenBank WP_001117823.1 and NP_543082.1—both putative endolysins), *Yersinia* spp. (GenBank CAJ28446.1-confirmed endolysin) and *Acinetobacter baumannii*, (GenBank WP_034684053.1, putative lysin).

FIG. 2 provides amino acid (bold font) and nucleotide (regular font) sequences of lysin polypeptides GN2, GN4, GN14, and GN43 reported in the present disclosure.

FIG. 5 provides amino acid sequences of five lysin peptides derived from GN4: PGN4, FGN4-1, FGN4-2, FGN4-3, and FGN4-4.

DETAILED DESCRIPTION

Definitions

Figure 3:
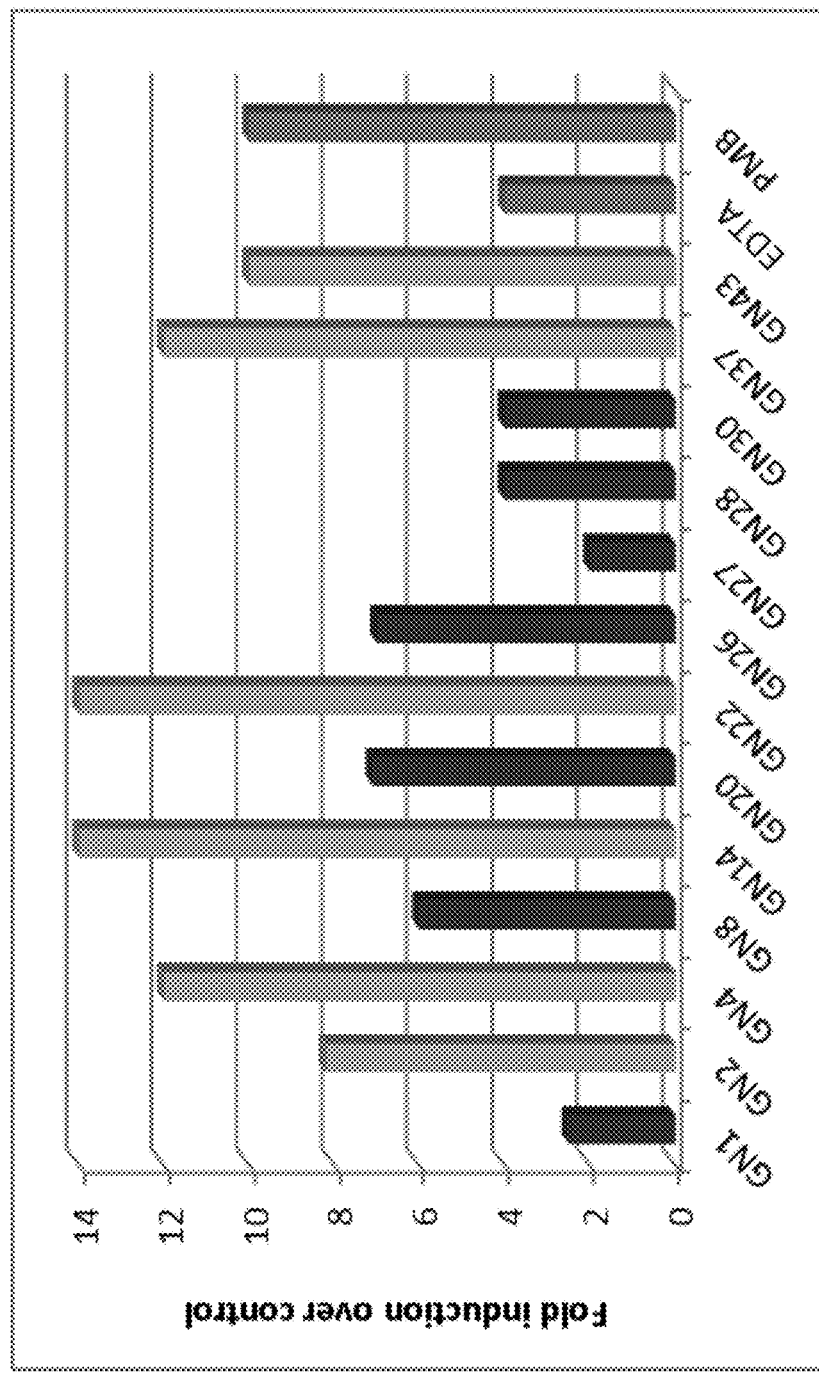
FIG. 3 is a bar graph depicting fold induction of fluorescence signal over control by *P. aeruginosa* strain PAO1 in the presence of various GN lysin polypeptides, wherein fluorescence indicates outer membrane permeabilization.

As used herein, the following terms and cognates thereof shall have the meanings ascribed to them below unless the context clearly indicates otherwise.

"Gram-negative bacteria" generally refers to bacteria which produce a crystal violet stain that is decolorized in Gram staining, i. e. they do not retain crystal violet dye in the Gram staining protocol. As used herein, the term "Gram-negative bacteria" may describe without limitation one or more (i.e., one or a combination) of the following bacterial species: *Acinetobacter baumannii, Acinetobacter haemolyticus, Actinobacillus actinomycetemcomitans, Aeromonas hydrophila, Bacteroides fragilis, Bacteroides* the *ataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei, Prevotella corporis, Prevotella intermedia, Prevotella endodontalis, Porphyromonas asaccharolytica, Campylobacter jejuni, Campylobacter coli, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydophila pneumoniae, Chlamydophila trachomatis, Ricketsia prowazekii, Coxiella burnetii, Ehrlichia chaffeensis,* or *Bartonella hensenae*. The compounds of the present disclosure will be useful in preventing or inhibiting pathogenic bacterial growth and in treating one or more bacterial infections, particularly but not necessarily exclusively involving Gram-negative bacteria and notably *P. aeruginosa*.

The term "bactericidal" in the context of an agent conventionally means having the property of causing the death of bacteria or capable of killing bacteria to an extent of at least a 3-log (99.9%) or better reduction among an initial population of bacteria.

The term "bacteriostatic" conventionally means having the property of inhibiting bacterial growth, including inhibiting growing bacterial cells, thus causing a 2-log (99%) or better and up to just under a 3-log reduction among an initial population of bacteria.

The term "antibacterial" in a context of an agent is used generically to include both bacteriostatic and bactericidal agents.

The term "drug resistant" in a context of a pathogen and more specifically a bacterium, generally refers to a bacterium that is resistant to the antimicrobial activity of a drug. When used in a more particular way, drug resistance specifically refers to antibiotic resistance. In some cases, a bacterium that is generally susceptible to a particular antibiotic can develop resistance to the antibiotic, thereby becoming a drug resistant microbe or strain. A "multi-drug resistant" pathogen is one that has developed resistance to at least two classes of antimicrobial drugs, each used as monotherapy. For example, certain strains of *Pseudomonas aeruginosa* have been found to be resistant to nearly all or all antibiotics including aminoglycosides, cephalosporins, fluoroquinolones, and carbapenems (Antibiotic Resistant Threats in the United States, 2013, U.S. Department of Health and Services, Centers for Disease Control and Prevention). One skilled in the art can readily determine if a bacterium is drug resistant using routine laboratory techniques that determine the susceptibility or resistance of a bacterium to a drug or antibiotic.

The term "pharmaceutically acceptable carrier" includes any and all solvents, additives, excipients, dispersion media, solubilizing agents, coatings, preservatives, isotonic and absorption delaying agents, surfactants, propellants and the like that are physiologically compatible. The carrier(s) must be "acceptable" in the sense of not being deleterious to the subject to be treated in amounts typically used in medicaments. Pharmaceutically acceptable carriers are compatible with the other ingredients of the composition without rendering the composition unsuitable for its intended purpose. Furthermore, pharmaceutically acceptable carriers are suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers or excipients include any of the standard pharmaceutical carriers such as phosphate buffered saline solutions, water, and emulsions such as oil/water emulsions and microemulsions.

For solid compositions comprising a lyophilized lysin polypeptide, excipients such as urea or mesna can be included to improve stability. Other excipients include bulking agents, buffering agents, tonicity modifiers, surfactants, preservatives and co-solvents.

For solid oral compositions comprising lysin polypeptide, suitable pharmaceutically acceptable excipients include, but are not limited to, starches, sugars, diluents, granulating agents, lubricants, binders, disintegrating agents and the like.

For liquid oral compositions, suitable pharmaceutically acceptable excipients include, but are not limited to, water, glycols, oils, alcohols, flavoring agents, preservatives, and the like.

For topical solid compositions such as creams, gels, foams, ointments, or sprays, suitable excipients include, but are not limited to a cream, a cellulosic or oily base, emulsifying agents, stiffening agents, rheology modifiers or thickeners, surfactants, emollients, preservatives, humectants, alkalizing or buffering agents, and solvents.

Suitable excipients for the formulation of the foam base include, but are not limited to, propylene glycol, emulsifying wax, cetyl alcohol, and glyceryl stearate. Potential preservatives include methylparaben and propylparaben.

The term "effective amount" refers to an amount which, when applied or administered in an appropriate frequency or dosing regimen, is sufficient to prevent or inhibit bacterial growth or prevent, reduce or ameliorate the onset, severity, duration or progression of the disorder being treated (here bacterial pathogen growth or infection), prevent the advancement of the disorder being treated, cause the regression of the disorder being treated, or enhance or improve the prophylactic or therapeutic effect(s) of another therapy, such as antibiotic or bacteriostatic therapy.

The term "co-administer" is intended to embrace separate administration of a lysin polypeptide and an antibiotic or any other antibacterial agent in a sequential manner as well as administration of these agents in a substantially simultaneous manner, such as in a single mixture/composition or in doses given separately, but nonetheless administered substantially simultaneously to the subject, for example at different times in the same day or 24-hour period. Such co-administration of lysin polypeptides with one or more additional antibacterial agents can be provided as a continuous treatment lasting up to days, weeks, or months. Additionally, depending on the use, the co-administration need not be continuous or co-extensive. For example, if the use were as a topical antibacterial agent to treat, e.g., a bacterial ulcer or an infected diabetic ulcer, the lysin could be administered only initially within 24 hours of the first antibiotic use and then the antibiotic use may continue without further administration of lysin.

The term "subject" refers to a subject to be treated and includes inter alia a mammal, a plant, a lower animal, a single cell organism or a cell culture. For example, the term "subject" is intended to include organisms, e.g., prokaryotes and eukaryotes, which are susceptible to or afflicted with Gram-negative bacterial infections. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or susceptible to a Gram-negative bacterial infection, whether such infection be systemic or confined to a particular organ or tissue.

The term "polypeptide" is used interchangeably with the term "protein" and "peptide" and refers to a polymer made from amino acid residues and having at least about 30 amino acid residues. The term includes not only polypeptides in isolated form, but also active fragments and derivatives thereof (defined below). The term "polypeptide" also encompasses fusion proteins or fusion polypeptides comprising a lysin polypeptide as described below and maintaining the lysin function. A polypeptide can be a naturally occurring polypeptide or an engineered or synthethically produced polypeptide. A particular lysin polypeptide can be, for example, derived or removed from a native protein by enzymatic or chemical cleavage, or can be prepared using conventional peptide synthesis techniques (e.g., solid phase synthesis) or molecular biology techniques (such as those disclosed in Sambrook, J. et al., *Molecular Cloning: A Laboratory Manual*, Cold Spring Harbor Press, Cold Spring Harbor, N.Y. (1989)) or can be strategically truncated or segmented yielding active fragments, as illustrated for example herein with a fragment of GN4 comprising the amphipathic domain of GN4 and further truncated versions thereof maintaining lysin activity against the same or at least one common target bacterium. Variants of native lysin polypeptides are also encompassed having at least 80% or at least 85% or at least 90% or at least 95% or at least 98% sequence identity with the native lysin polypeptide (which, as stated above includes active fragments of a native lysin protein).

The term "fusion polypeptide" refers to an expression product resulting from the fusion of two or more nucleic acid segments, resulting in a fused expression product typically having two domains or segments with different properties or functionality. In a more particular sense, the term "fusion polypeptide" also refers to a polypeptide or peptide comprising two or more heterologous polypeptides or peptides covalently linked, either directly or via an amino acid or peptide linker. The polypeptides forming the fusion polypeptide are typically linked C-terminus to N-terminus, although they can also be linked C-terminus to C-terminus, N-terminus to N-terminus, or N-terminus to C-terminus. The term "fusion polypeptide" can be used interchangeably with the term "fusion protein." Thus the open-ended expression "a polypeptide comprising" a certain structure includes larger molecules than the recited structure such as fusion polypeptides.

The term "heterologous" refers to nucleotide, peptide, or polypeptide sequences that are not naturally contiguous. For example, in the context of the present disclosure, the term "heterologous" can be used to describe a combination or fusion of two or more peptides and/or polypeptides wherein the fusion peptide or polypeptide is not normally found in nature, such as for example a lysin polypeptide or active fragment thereof and a cationic and/or a polycationic peptide, an amphipathic peptide, a sushi peptide (Ding et al. *Cell Mol Life Sci.*, 65(7-8):1202-19 (2008)), a defensin peptide (Ganz, T. *Nature Reviews Immunology* 3, 710-720 (2003)), a hydrophobic peptide and/or an antimicrobial peptide which may have enhanced lysin activity. Included in this definition are two or more lysin polypeptides or active fragments thereof. These can be used to make a fusion polypeptide with lysin activity The term "active fragment" refers to a portion of a full-length polypeptide disclosed herein which retains one or more functions or biological activities of the isolated original polypeptide. See for example GN4 in FIG. 2 and fragments thereof in FIG. 5 (FGN4-1 and FGN4-2). A biological activity of particular interest herein is that of a lysin active to bore through the outer membrane and hydrolyze the coating of Gram-negative bacteria, whether by cleaving a sugar backbone or peptide bond.

The term "amphipathic peptide" refers to a peptide having both hydrophilic and hydrophobic functional groups. Preferably, secondary structure places hydrophobic and hydrophilic amino acid residues at different ends of the peptide. These peptides often adopt a helical secondary structure.

The term "cationic peptide" refers to a peptide having positively charged amino acid residues. Preferably, a cationic peptide has a pKa-value of 9.0 or greater. The term "cationic peptide" in the context of the present disclosure also encompasses polycationic peptides.

The term "polycationic peptide" as used herein refers to a synthetically produced peptide composed of mostly positively charged amino acid residues, in particular lysine and/or arginine residues. The amino acid residues that are not positively charged can be neutrally charged amino acid residues and/or negatively charged amino acid residues and/or hydrophobic amino acid residues.

The term "hydrophobic group" refers to a chemical group such as an amino acid side chain which has low or no affinity for water molecules but higher affinity for oil molecules. Hydrophobic substances tend to have low or no solubility in water or aqueous phases and are typically apolar but tend to have higher solubility in oil phases. Examples of hydrophobic amino acids include glycine (Gly), alanine (Ala), valine (Val), leucine (Leu), isoleucine (Ile), proline (Pro), phenylalanine (Phe), methionine (Met), and tryptophan (Trp).

The term "augmenting" within the context of the present disclosure means that a degree of antimicrobial activity is higher than it would be otherwise. "Augmenting" encompasses additive as well as synergistic (superadditive) effects.

The term "synergistic" or "superadditive" in relation to an effect means a beneficial effect brought about by two active substances that exceeds that produced by each substance administered or applied alone. One or both active ingredients may be employed at a subtreshold level, i.e., a level at which if the active substance is employed individually produces no or a very limited effect.

The term "treatment" refers to any process, action, application, therapy, or the like, wherein a subject, including a human being, is subjected to medical aid with the object of curing a disorder, or eradicating a pathogen, or improving the subject's condition, directly or indirectly. Treatment also refers to reducing incidence, or alleviating symptoms, eliminating recurrence, preventing recurrence, preventing incidence, improving symptoms, improving prognosis or combinations thereof. "Treatment" further encompasses reducing the population, growth rate or virulence of the bacteria in the subject and thereby controlling or reducing a bacterial infection in a subject or bacterial contamination of an organ or tissue or environment. Thus "treatment" that reduces incidence is effective to inhibit growth of at least one Gram-negative bacterium in a particular milieu, whether it be a subject or an environment. On the other hand "treatment" of an already established infection refers to reducing the population or killing, including even eradicating the Gram-negative bacteria responsible for an infection or contamination.

The term "preventing" includes the prevention of the incidence, recurrence, spread, onset or establishement of a disorder such as a bacterial infection. It is not intended that the present disclosure be limited to complete prevention or to prevention of establishment of an infection. In some embodiments, the onset is delayed, or the severity of a subsequently contracted disease is reduced, and such constitute examples of prevention. Contracted diseases in the context of the present disclosure encompass both those manifesting with clinical or subclinical symptoms, such as the detection of as well as the detection of growth of a bacterial pathogen when symptoms associated with such pathologyare not yet manifest.

The term "derivative" in the context of a peptide or polypeptide (which as stated herein includes an active fragment) is intended to encompass for example, a polypeptide modified to contain one or more-chemical moieties other than an amino acid that do not substantially adversely impact or destroy the lysin activity. The chemical moiety can be linked covalently to the peptide, e.g., via an amino terminal amino acid residue, a carboxy terminal amino acid residue, or at an internal amino acid residue. Such modifications include the addition of a protective or capping group on a reactive moiety, addition of a detectable label, such as antibody and/or fluorescent label, addition or modification of glycosylation, or addition of a bulking group such as PEG (pegylation) and other changes that do not substantially adversely impact or destroy the activity of the lysin polypeptide.

Commonly used protective groups that may be added to lysin polypeptides include, but are not limited to t-Boc and Fmoc.

Commonly used fluorescent label proteins such as, but not limited to, green fluorescent protein (GFP), red fluorescent protein (RFP), cyan fluorescent protein (CFP), yellow fluorescent protein (YFP) and mCherry, are compact proteins that can be bound covalently or noncovalently to a lysin polypeptide or fused to a lysin polypeptide without interfering with normal functions of cellular proteins. Typically, a polynucleotide encoding a fluorescent protein is inserted upstream or downstream of the lysin polynucleotide sequence. This will produce a fusion protein (e.g., Lysin Polypeptide::GFP) that does not interfere with cellular function or function of a lysin polypeptide to which it is attached.

Polyethylene glycol (PEG) conjugation to proteins has been used as a method for extending the circulating half-life of many pharmaceutical proteins. Thus, in the context of lysin polypeptide derivatives, the term "derivative" encompasses lysin polypeptides chemically modified by covalent attachment of one or more PEG molecules. It is anticipated that pegylated lysin polypeptides will exhibit prolonged circulation half-life compared to the unpegylated lysin polypeptides, while retaining biological and therapeutic activity.

The term "percent amino acid sequence identity" with respect to the lysin polypeptide sequences is defined herein as the percentage of amino acid residues in a candidate sequence that are identical with the amino acid residues in the specific lysin polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available software such as BLAST or Megalign (DNASTAR) software. Two or more polypeptide sequences can be anywhere from 0-100% identical, or any integer value there between. In the context of the present disclosure, two polypeptides are "substantially identical" when at least 80% of the amino acid residues (preferably at least about 85%, at least about 90%, and preferably at least about 95%) are identical. The term "percent (%) amino acid sequence identity" as described herein applies to lysin peptides as well. Thus, the term "substantially identical" will encompass mutated, truncated, fused, or otherwise sequence-modified variants of isolated lysin polypeptides and peptides described herein, and active fragments thereof, as well as polypeptides with substantial sequence identity (e.g., at least 80%, at least 85%, at least 90%, or at least 95% identity as measured for example by one or more methods referenced above) as compared to the reference polypeptide.

Two amino acid sequences are "substantially homologous" when at least about 80% of the amino acid residues (preferably at least about 85%, at least about 90%, and preferably at least about 95%) are identical, or represent conservative substitutions. The sequences of lysin polypeptides of the present disclosure, are substantially homologous when one or more, or several, or up to 10%, or up to 15%, or up to 20% of the amino acids of the lysin polypeptide are substituted with a similar or conservative amino acid substitution, and wherein the resulting lysin have the profile of activities, antibacterial effects, and/or bacterial specificities of lysin polypeptides disclosed herein. The meaning of "substantially homologous" described herein applies to lysin peptides as well.

The term "inhalable composition" refers to pharmaceutical compositions of the present disclosure that are formulated for direct delivery to the respiratory tract during or in conjunction with routine or assisted respiration (e.g., by intratracheobronchial, pulmonary, and/or nasal administration), including, but not limited to, atomized, nebulized, dry powder and/or aerosolized formulations.

The term "biofilm" refers to bacteria that attach to surfaces and aggregate in a hydrated polymeric matrix of their own synthesis. A biofilm is an aggregate of microorganisms in which cells adhere to each other on a surface. These adherent cells are frequently embedded within a self-produced matrix of extracellular polymeric substance (EPS). Biofilm EPS, which is also referred to as slime (although not everything described as slime is a biofilm) or plaque, is a polymeric conglomeration generally composed of extracellular DNA, proteins, and polysaccharides.

The term "suitable" in the context of an antibiotic being suitable for use against certain bacteria refers to an antibiotic that was found to be effective against those bacteria even if resistance subsequently developed.

The term "antimicrobial peptide" (AMP) refers to a member of a wide range of short (generally 6 to 50 amino acid residues in length) cationic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphipathicity and short size), AMP sequences vary greatly, and at least four structural groups (alpha.-helical, beta.-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., *Nature Reviews Microbiology,* 7, 245-250 (2009)).

Defensins are a large family of small, cationic, cysteine- and arginine-rich antimicrobial peptides, found in both vertebrates and invertebrates (Wilmes, M. and Sahl, H., *Int J Med Microbiol.;*304(1):93-9 (2014)). Defensins are divided into five groups according to the spacing pattern of cysteines: plant, invertebrate, alpha-, beta-, and theta-defensins. The latter three are mostly found in mammals. alpha-defensins are proteins found in neutrophils and intestinal epithelia. Beta-defensins are the most widely distributed and are secreted by leukocytes and epithelial cells of many kinds theta-defensins have been rarely found so far e.g. in leukocytes of rhesus macaques. Defensins are active against bacteria, fungi and many enveloped and nonenveloped viruses. However, the concentrations needed for efficient killing of bacteria are mostly high, i.e. in the micromolar range. Activity of many peptides may be limited in the presence of physiological salt conditions, divalent cations and serum. In addition, defensins often have hemolytic activity which is not desirable for the products and methods of the present disclosure.

Sushi peptides are characterized by the presence of sushi domains, also known as complement control protein (CCP) modules or short consensus repeats (SCR)). Sushi domains are found in a variety of complement and adhesion proteins, which contain tandem arrangements of Sushi domains interspersed by short linking sequences. Sushi domains contain a consensus sequence spanning approximately 60 residues, which in turn contains four invariant cysteine residues that are involved in intramolecular disulphide bonds, a highly conserved tryptophan, and conserved glycine, proline and hydrophobic residues (Kirkitadze, M. and Barlow, P., *Immunol Rev.,* 180:146-61 (2001)). Sushi domains are known to be involved in protein—protein and protein—ligand interactions. Peptides containing a Sushi domain have been shown to have antimicrobial activities (Ding, J L. and Ho, B. *Drug Development Research,* 62:317-335 (2004)).

Cathelicidins are multifunctional antimicrobial peptides also known as cationic host-defence peptides (CHDP)—a class of peptides proposed as antimicrobial therapeutics—and an important component of innate host defence against infection. In addition to microbicidal potential, these peptides have properties with the capacity to modulate inflammation and immunity Recently, the delivery of exogenous human cathelicidin LL-37 was found to enhance a protective pro-inflammatory response to infection in a murine model of acute *P. aeruginosa* lung infection, demonstrating cathelicidin-mediated enhancement of bacterial clearance in vivo (Beaumont et al. *PLoS One.* 2; 9(6):e99029 (2014)). Thus, cathelicidin effectively promoted bacterial clearance from the lung in the absence of direct microbicidal activity, with an enhanced early neutrophil response that required both infection and peptide exposure and was independent of native cathelicidin production. Furthermore, although cathelicidin-deficient mice had an intact early cellular inflammatory response, later phase neutrophil response to infection was absent in these animals, with significantly impaired clearance of *P. aeruginosa*. These findings demonstrated the importance of the modulatory properties of cathelicidins in pulmonary infection in vivo and highlighted a key role for cathelicidins in the induction of protective pulmonary neutrophil responses, specific to the infectious milieu. Beaumont, P. E. et al, *PLoS One*. 2014; 9(6): e99029. Published online 2014 Jun. 2. doi: 10.1371/journal.pone.0099029.

EMBODIMENTS

The present disclosure relates to new antibacterial agents against Gram-negative bacteria. In particular, the present disclosure relates to lysin polypeptides (including active fragments thereof) active against Gram-negative bacteria, such as *Pseudomonas aeruginosa*. Examples of such lysin polypeptides are those having an amino acid sequence within the set SEQ ID NO: 1-SEQ ID NO: 10. The native sequences were identified by bioinformatics techniques from a previously sequenced but partially elucidated phage genome. Although some of the sequences thus identified had been annotated as putative endolysins, no function had been previously definitively attributed to polypeptides having these sequences. Moreover, several sequences annotated as putative endolysisns, on synthesis or expression, turned out to be wholly devoid of lysin activity or inactive against the target pathogen. On isolation, expression and testing, only a handful of the bioinformatically identified sequences in fact had Gram-negative lysin function. Additionally, active fragments of the lysins were identified and sequence-modified active peptides and polypeptides having Gram-negative lysin activity were prepared. Furthermore, in accordance with the present disclosure, such sequence modified papetides include fragments of the confirmed native Gram-negative lysin polypeptides maintaining lysin activity, as well as variants thereof having 80% or more (such as at least 85%, at lestt 90% at least 85% or at least 98%) sequence identity with the native lysin polypeptides or active fragments thereof and indeed the nonidentical portions might include substitutions with both natural and non-natural (synthetic) amino acid residues. The present inventors have determined that the alpha helical domain of the C-terminal end of these polypeptides is important for Gram-negative lysin activity and have conducted studies to pinpoint the activity, but any peptide with a sequence that is 80% or more (such as 85%, 90%, 95% or 98% or 99%) identical to the native lysins disclosed herein or fragments thereof can be quickly tested for activity against Gram-negative bacteria including *P. aeruginosa*, and others such as *Klebsiella* spp., *Enterobacter* spp., *Escherichia coli*, *Citrobacter freundii*, *Salmonella typhimurium*, *Yersinia pestis*, and *Franciscella tulerensis*. Such testing can follow for example the teachings provided in Examples 2, 3, 4, or Prophetic Example 1. Of course, the testing procedures and protocols themselves are not limited to those in these Examples but can be any methods known to those skilled in the art for assessing effectiveness of an antibacterial and indeed an antimicronbial agent.

In one embodiment, the present disclosure provides methods for treatment of a bacterial infection in a subject caused by Gram-negative bacteria comprising administering to the subject an effective amount of a lysin polypeptide having at least 80% or at least 85% or at least 90% or at least 95% amino acid sequence identity to SEQ ID NO: 1 through SEQ ID NO: 10. The bacteria may be selected from the group consisting of *Acinetobacter baumannii*, *Acinetobacter haemolyticus*, *Actinobacillus actinomycetemcomitans*, *Aeromonas hydrophila*, *Bacteroides fragilis*, *Bacteroides theataioatamicron*, *Bacteroides distasonis*, *Bacteroides ovatus*, *Bacteroides vulgatus*, *Bordetella pertussis*, *Brucella melitensis*, *Burkholderia cepacia*, *Burkholderia pseudomallei*, *Burkholderia mallei Fusobacterium*, *Prevotella corporis*, *Prevotella intermedia*, *Prevotella endodontalis*, *Porphyromonas asaccharolytica*, *Campylobacter jejuni*, *Campylobacter fetus*, *Campylobacter coli*, *Citrobacter freundii*, *Citrobacter koseri*, *Edwarsiella tarda*, *Eikenella corrodens*, *Enterobacter cloacae*, *Enterobacter aerogenes*, *Enterobacter agglomerans*, *Escherichia coli*, *Francisella tularensis*, *Haemophilus influenzae*, *Haemophilus ducreyi*, *Helicobacter pylori*, *Kingella kingae*, *Klebsiella pneumoniae*, *Klebsiella oxytoca*, *Klebsiella rhinoscleromatis*, *Klebsiella ozaenae*, *Legionella penumophila*, *Moraxella catarrhalis*, *Morganella morganii*, *Neisseria gonorrhoeae*, *Neisseria meningitidis*, *Pasteurella multocida*, *Plesiomonas shigelloides*, *Proteus mirabilis*, *Proteus vulgaris*, *Proteus penneri*, *Proteus myxofaciens*, *Providencia stuartii*, *Providencia rettgeri*, *Providencia alcalifaciens*, *Pseudomonas aeruginosa*, *Pseudomonas fluorescens*, *Salmonella typhi*, *Salmonella paratyphi*, *Serratia marcescens*, *Shigella flexneri*, *Shigella boydii*, *Shigella sonnei*, *Shigella dysenteriae*, *Stenotrophomonas maltophilia*, *Streptobacillus moniliformis*, *Vibrio cholerae*, *Vibrio parahaemolyticus*, *Vibrio vulnificus*, *Vibrio alginolyticus*, *Yersinia enterocolitica*, *Yersinia pestis*, *Yersinia pseudotuberculosis*, *Chlamydia pneumoniae*, *Chlamydia trachomatis*, *Ricketsia prowazekii*, *Coxiella burnetii*, *Ehrlichia chafeensis*, and *Bartonella hensenae*. For example, in a particular embodiment, the Gram-negative bacterial infection is an infection caused bacteria selected from the group consisting of *Acinetobacter baumannii*, *Bordetella pertussis*, *Burkholderia cepacia*, *Burkholderia pseudomallei*, *Burkholderia mallei*, *Campylobacter jejuni*, *Campylobacter coli*, *Enterobacter cloacae*, *Enterobacter aerogenes*, *Escherichia coli*, *Francisella tularensis*, *Haemophilus influenzae*, *Haemophilus ducreyi*, *Helicobacter pylori*, *Klebsiella pneumoniae*, *Legionella penumophila*, *Moraxella catarrhalis*, *Morganella morganii*, *Neisseria gonorrhoeae*, *Neisseria meningitidis*, *Pasteurella multocida*, *Proteus mirabilis*, *Proteus vulgaris*, *Pseudomonas aeruginosa*, *Salmonella typhi*, *Serratia marcescens*, *Shigella flexneri*, *Shigella boydii*, *Shigella sonnei*, *Shigella dysenteriae*, *Stenotrophomonas maltophilia*, *Vibrio cholerae*, and *Chlamydia pneumoniae*. In a specific embodiment, the Gram-negative bacterial infection is an infection caused by one or more of bacteria selected from the group consisting of *Salmonella typhimurium*, *Salmonella typhi*, *Shigella* spp., *Escherichia coli*, *Acinetobacter baumanii*, *Pseudomonas aeruginosa*, *Klebsiella pneumonia*, *Neisseria gonorrhoeae*, *Neisseria meningitides*, *Serratia* spp. *Proteus mirabilis*, *Morganella morganii*, *Providencia* spp., *Edwardsiella* spp., *Yersinia* spp., *Haemophilus influenza*, *Bartonella quintana*, *Brucella* spp., *Bordetella pertussis*, *Burkholderia* spp., *Moraxella* spp., *Francisella tularensis*, *Legionella pneumophila*, *Coxiella burnetii*, *Bacteroides* spp., *Enterobacter* spp., and *Chlamydia* spp.

Based on (i) the fact that the lysin peptides and polypeptides of the present disclosure are able to bore through the OM of Gram-negative bacteria and reach their substrate, killing such bacteria and substantially reducing the rate of growth of bacterial colonies, and (ii) on similar observations with other lysin polypeptides that are engineered to penetrate the OM in buffer and media such as artilysins, it is anticipated that the lysin polypeptides of the present disclosure will be useful in treating one or more Gram-negative bacterial infections. Moreover, the fact that the present lysin polypeptides possess activity against Gram-negative targets even before fusion (if any) with cationic and other antimicrobial peptides) may be advantageous over artilysisns as the latter appear to be inhibited by human sera. Deslouches, B. et al, Activity of the De Novo Engineered Antimicrobial Peptide WLBU2 against *Pseudomonas aeruginosa* in Human Serum and Whole Blood: Implications for Systemic Applications, Antimicrobial Agents & Chemotherapy, August 2005, p. 3208-3216 Vol. 49, No 8; Brogden N. et al, Int J Antimicrob Agents. 2011 September; 38(3): 217-225. doi: 10.1016/j.ijantimicag.2011.05.004; Svenson, J. et al, J. Med. Chem., 2007, 50 (14), pp 3334-3339.

In one embodiment, the terms "infection" and "bacterial infection" may refer inter alia to a respiratory tract infection (RTI), especially but not exclusively to lower respiratory tract infections. In another embodiment, the terms "infection" and "bacterial infection" may refer to a sexually transmitted disease. In yet another embodiment, the terms "infection" and "bacterial infection" may refer to a urinary tract infection. In a further embodiment, the terms "infection" and "bacterial infection" may refer to acute exacerbation of chronic bronchitis (ACEB). In still another embodiment, the terms "infection" and "bacterial infection" may refer to respiratory tract infections of patients having cystic fibrosis (CF). In still a further embodiment, the terms "infection" and "bacterial infection" may refer to acute otitis media or neonatal septisemia. In yet a further embodiment, the terms "infection" and "bacterial infection" may refer to acute sinusitis. In one embodiment, the terms "infection" and "bacterial infection" may refer to an infection caused by drug resistant bacteria even multidrug-resistant bacteria. In another embodiment, the terms "infection" and "bacterial infection" may refer to catheter-related sepsis. In yet another embodiment, the terms "infection" and "bacterial infection" may refer to chlamydia. In a further embodiment, the terms "infection" and "bacterial infection" may refer to community-acquired pneumonia (CAP) or to nosocomial respiratory tract infections. In still a further embodiment, the terms "infection" and "bacterial infection" may refer to a complicated skin and skin structure infection. In yet a further embodiment, the terms "infection" and "bacterial infection" may refer to uncomplicated skin and skin structure infections. In one embodiment, the terms "infection" and "bacterial infection" may refer to endocarditis. In another embodiment, the terms "infection" and "bacterial infection" may refer to febrile neutropenia. In still another embodiment, the terms "infection" and "bacterial infection" may refer to gonococcal cervicitis. In yet another embodiment, the terms "infection" and "bacterial infection" may refer to gonococcal urethritis. In a further embodiment, the terms "infection" and "bacterial infection" may refer to hospital-acquired pneumonia (HAP). In still a further embodiment, the terms "infection" and "bacterial infection" may refer to osteomyelitis. In yet a further embodiment, the terms "infection" and "bacterial infection" may refer to sepsis. Common Gram-negative pathogens and associated infections are listed in Table 1 of the present disclosure. These embodiments as well as pathogens and diseases listed in Table 1 are meant to serve as examples of uses of the present methods and are not intended to be limiting.

TABLE 1

Medically relevant Gram-negative bacteria and associated diseases.

| Gram-negative pathogen | Primary Disease/s |
|---|---|
| Salmonella typhimurium | Gastrointestinal (GI) infections-salmonellosis |
| Shigella spp. | GI infections-shigellosis |
| Escherichia coli | Urinary tract infections (UTIs) |
| Acinetobacter baumanii | Wound infections |
| Pseudomonas aeruginosa | bloodstream infections and pneumonia |
| Klebsiella pneumoniae | pneumonia, UTIs, and bloodstream infections |

TABLE 1-continued

Medically relevant Gram-negative bacteria and associated diseases.

| Gram-negative pathogen | Primary Disease/s |
|---|---|
| Neisseria gonorrhoeae | Sexually transmitted disease (STD)-gonorrhea |
| Neisseria meningitides | Meningitis |
| Serratia spp. | Catheter contaminations, UTIs, and pneumonia |
| Proteus mirabilis | UTIs |
| Morganella spp. | UTIs |
| Providencia spp. | UTIs |
| Edwardsiella spp. | UTIs |
| Salmonella typhi | GI infections-typhoid fever |
| Yersinia pestis | Bubonic and pneumonic plague |
| Yersinia enterocolitica | GI infections |
| Yersinia pseudotuberculosis | GI infections |
| Haemophilus influenza | Meningitis |
| Bartonella Quintana | Trench fever |
| Brucella spp. | Brucellosis |
| Bordetella pertussis | Respiratory-Whooping cough |
| Burkholderia spp. | Respiratory |
| Moraxella spp. | Respiratory |
| Francisella tularensis | Tularemia |
| Legionella pneumophila | Respiratory-Legionnaires' disease |
| Coxiella burnetii | Q fever |
| Bacteroides spp. | Abdominal infections |
| Enterobacter spp. | UTIs and respiratory |
| Chlamydia spp. | STDs, respiratory, and ocular |

In one embodiment, the present disclosure provides methods for treatment of the Gram-negative bacterial infection in a subject caused by *Pseudomonas aeruginosa* and optionally by at least one additional species of Gram-negative bacteria such as those selected from the group consisting of, *Klebsiella* spp., *Enterobacter* spp., *Escherichia coli, Citrobacter freundii, Salmonella typhimurium, Yersinia pestis*, and *Franciscella tulerensis*, which are the Gram-negative bacteria most significant in human disease.

In one embodiment, the present disclosure provides methods for treatment of the Gram-negative bacterial infection in a subject caused by *Pseudomonas aeruginosa*. *Pseudomonas aeruginosa* (*P. aeruginosa*) is an oxidase-positive, Gram-negative, rod-shaped organism that is found ubiquitously in the environment. *P. aeruginosa* can grow in numerous habitats, including but not limited to soil, water, and on plant and animal tissue. It is an opportunistic organism and one of the most problematic nosocomial pathogens capable of causing localized or systemic disease in susceptible individuals such as people who have cystic fibrosis, cancer, burns, diabetic ulcers or an immune system deficiency. In a hospital setting in particular, it has become resistant to many commonly used antibiotics.

According to data from the US Centers for Disease Control and Prevention and the National Nosocomial Infection Surveillance System, *P. aeruginosa* is the second most common cause of nosocomial pneumonia, the third most common cause of urinary tract infection, the fourth most common cause of surgical site infection, the seventh most frequently isolated pathogen from the bloodstream, and the fifth most common isolate overall from all sites (Solh and Alhajhusain, *J Antimicrob Chemother.* 64(2):229-38 (2009)). Furthermore, *P. aeruginosa* is the most common multidrug-resistant (MDR) Gram-negative pathogen causing pneumonia in hospitalized patients (Goossens et al., *Clin Microbiol Infect.* 980-3 (2003)).

Nonlimiting examples of infections caused by *P. aeruginosa* include: A) Nosocomial infections: 1. Respiratory tract infections especially in cystic fibrosis patients and mechanically-ventilated patients; 2. Bacteraemia and sepsis; 3, Wound infections, particularly those of burn victims; 4. Urinary tract infections; 5. Post-surgery infections on invasive devises; 6. Endocarditis by intravenous administration of contaminated drug solutions; 7, Infections in patients with acquired immunodeficiency syndrome, cancer chemotherapy, steroid therapy, hematological malignancies, organ transplantation, renal replacement therapy, and other conditions with severe neutropenia. B) Community-acquired infections: 1. Community-acquired respiratory tract infections; 2. Meningitis; 3. Folliculitis and infections of the ear canal caused by contaminated water; 4. Malignant otitis externa in the elderly and diabetics; 5. Osteomyelitis of the caleaneus in children; 6. Eye infections commonly associated with contaminated contact lens; 7. Skin infections such as nail infections in people whose hands are frequently exposed to water; 8. Gastrointestinal tract infections; and 9. Muscoskeletal system infections.

In some embodiments, the lysin polypeptides of the present disclosure are used to treat a subject at risk for acquiring an infection due to *P. aeruginosa* and/or another Gram-negative bacterium. Subjects at risk for acquiring a *P. aeruginosa* or other Gram-negative bacterial infection include for example, but are not limited to, cystic fibrosis patients, neutropenic patients, patients with necrotising enterocolitis, burn victims, patients with wound infections, and more generally patients in a hospital setting, in particular surgical patients and patients being treated using an implantable medical device such as a catheter, for example a central venous catheter, a Hickman device, or electrophysiologic cardiac devices, for example pacemakers and implantable defibrillators. Other patient groups at risk for infection with Gram-negative bacteria including *P. aeruginosa* include without limitation patients with implanted prostheses such a total joint replacement (for example total knee or hip replacement).

In one embodiment, the subject is suffering from a Gram-negative bacterial respiratory infection. In another embodiment, the subject is suffering from cystic fibrosis and each active ingredient is independently administered in an inhalable composition, an oral composition or a buccal composition. In a more specific embodiment, the subject is suffering from a Gram-negative bacterial respiratory infection associated with cystic fibrosis and each of the active ingredients is co-administered in an inhalable composition. In one embodiment, the subject is suffering from a wound that has been infected with *P. aeruginosa* or another Gram-negative bacterium. An example of a wound that is treatable by the methods of the present disclosure is an infected burn or a burn at risk of becoming infected. Such burns include thermal (heat) burns, cold temperature burns, chemical burns, electrical burns, or radiation burns.

Additionally, *P. aeruginosa* and other Gram-negative bacteria frequently colonize hospital food, sinks, taps, mops, and respiratory equipment. The infection is spread from patient to patient via contact with fomites or by ingestion of contaminated food and water (Barbara Iglewski, Medical Microbiology, 4th edition, Chapter 27, *Pseudomonas*, 1996).

In one emdodiment, the lysin polypeptides of the present disclosure are used for the treatment of a Gram-negative bacterial infection (or of an infection that has not been characterized) in a subject in combination with other therapies. Such optional combination therapy may comprise co-administering to the patient in need thereof an additional therapeutic agent, such as an antibiotic or other bactericidal or bacteriostatic agent, and/or another lysin targeting a different component of the pathogen's surface (for example, targeting a different component of the outer membrane).

Besides antibiotics, bactericidal and bacteriostatic agents include but are not limited to lysins, disinfectatnts, antiseptics, and preservatives. Any of these can be optionally used in combination with the lysin polypeptides of the present disclosure.

Antimicrobial disinfectants include, but are not limited to hypochlorites, chloramines, dichloroisocyanurate and trichloroisocyanurate, wet chlorine, chlorine dioxide, peracetic acid, potassium persulfate, sodium perborate, sodium percarbonate and urea perhydrate, iodpovidone, iodine tincture, iodinated nonionic surfactants, ethanol, n-propanol and isopropanol and mixtures thereof; 2-phenoxyethanol and 1- and 2-phenoxypropanol, cresols, hexachlorophene, triclosan, trichlorophenol, tribromophenol, pentachlorophenol, Dibromol and salts thereof, benzalkonium chloride, cetyl trimethylammonium bromide or chloride, didecyldimethylammonium chloride, cetylpyridinium chloride, benzethonium chloride, chlorhexidine, glucoprotamine, octenidine dihydrochloride, ozone and permanganate solutions, colloidal silver, silver nitrate, mercury chloride, phenylmercury salts, copper, copper sulfate, copper oxide-chloride, phosphoric acid, nitric acid, sulfuric acid, amidosulfuric acid, toluenesulfonic acid, sodium hydroxide, potassium hydroxide, and calcium hydroxide.

The combination of lysin polypeptides of the present disclosure with antiseptic reagents may provide more efficacy against Gram-negative bacteria than antibiotic combinations. Antiseptic reagents include, but are not limited to Daquin's solution, sodium or potassium hypochlorite solution, solution of sodium benzenesulfochloramide, certain iodine preparations, such as iodopovidone, peroxides as urea perhydrate solutions and pH-buffered peracetic acid solutions, alcohols with or without antiseptic additives, weak organic acids such as sorbic acid, benzoic acid, lactic acid and salicylic acid, some phenolic compounds, such as hexachlorophene, triclosan and Dibromol, and cation-active compounds, such as benzalkonium, chlorhexidine, methylisothiazolone, α-terpineol, thymol, chloroxylenol octenidine solutions.

The lysins of the present disclosure can be co-administered with standard care antibiotics or with antibiotics of last resort, individually or in various combinations as within the skill of the art. Traditional antibiotics used against *P. aeruginosa* activity include aminoglycosides, ticarcillin, ureidopenicillins, ceftazidime, cefepime, aztreonam, carbapenems, ciprofloxacin, levofloxacin, etc. (Table 2). Lysin polypeptides of the present disclosure may be co-administered with antibiotics used for the treatment of *P. aeruginosa* and others listed in Table 2. The list of antibiotics for other Gram-negative bacteria, such as *Klebsiella* spp., *Enterobacter* spp., *Escherichia coli*, *Citrobacter freundii*, *Salmonella typhimurium*, *Yersinia pestis*, and *Franciscella tulerensis*, will be similar as that provided above for *P. aeruginosa* and will be standard care antibiotics for a particular bacterium involved or even antibiotics of last resort (if the particular strain is resistant to standard care antibiotics).

Additional optional therapeutic agents to be co-administered include, but are not limited to the antibiotics mentioned above and those listed in Table 2, such as a ticarcillin-clavulanate combination, piperacillin-tazobactam combination, ceftazidime, cefepime, cefoperazone, ciprofloxacin, levofloxacin, imipenem, meropenem, doripenem, gentamicin, tobramycin, amikacin, polymyxin B, and colistin (polymixin E). For treatment of wounds, therapeutic agents to be co-administered include, but are not limited to, a propylene glycol hydrogel (e.g., SOLUGEL® (Johnson & Johnson)); an antiseptic; an antibiotic; and a corticosteroid.

TABLE 2

Antibiotics used for the treatment of *Pseudomonas aeruginosa*

| Class | Agent |
| --- | --- |
| Penicillins | Ticarcillin-clavulanate |
|  | Piperacillin-tazobactam |
| Cephalosporins | Ceftazidime |
|  | Cefepime |
|  | Cefoperazone |
| Monobactams | Aztreonam |
| Flouroquinolones | Ciprofloxacin |
|  | Levofloxacin |
| Carbapemens | Imipenem |
|  | Meropenem |
|  | Doripenem |
| Aminoglycosides | Gentamicin |
|  | Tobramycin |
|  | Amikacin |
| Polymixins | Colistin |
|  | Polymyxin B |

Antibiotic peptides such as polymyxin B and the related colistin (polymyxin E) have been used as antibacterial agents for the treatment of *P. aeruginosa* bacterial infections. Thus, in one embodiment, the lysin polypeptides of the present disclosure are to be co-administered with polymyxin B and/or colistin.

Combining lysin polypeptides of the present disclosure with antibiotics provides an efficacious new antimicrobial regimen. In one embodiment, co-administration of lysin polypeptides of the present disclosure with one or more antibiotics may be carried out at reduced doses and amounts of either the lysin or the antibiotic or both, and/or reduced frequency and/or duration of treatment with augmented bactericidal and bacteriostatic activity, reduced risk of antibiotic resistance and with reduced risk of deleterious neurological or renal side effects (such as those associated with colistin or polymyxin B use). Prior studies have shown that total cumulative colistin dose is associated with kidney damage, suggesting that decrease in dosage or shortening of treatment duration using the combination therpy with lysin polypepides could decrease the incidence of nephrotoxicity (Spapen et al. *Ann Intensive Care.* 1: 14 (2011)). As used herein the term "reduced dose" refers to the dose of one active ingredient in the combination compared to monotherapy with the same active ingredient. Ditto for "duration of treatment." In some embodiments, the dose of the lysin or the antibiotic in a combination may be suboptimal or even subthreshold compared to the respective monotherapy.

In some embodiments, lysin polypeptides of the present disclosure are used to treat a bacterial infection such as an infection caused by a drug resistant Gram-negative bacteria. In further embodiments, lysin polypeptides of the present disclosure alone or with one or more antibiotics are used to treat bacterial infection such as an infection caused by a multi-drug resistant Gram-negative bacteria. Drug resistant or multi-drug resistant Gram-negative bacteria in the context of this disclosure inludes, but is not limited to *P. aeruginosa.*

In practice, infections are commonly polymicrobial, with mixed Gram-positive and Gram-negative species (Citron et al. *J Clin Microbiol.* 45(9): 2819-2828 (2007)). In some embodiments, lysin polypeptides of the present disclosure active against gram-negative bacteria can be used not only with an antibiotic effective against gram-negative bacteria but also in combination with one or more antibiotic and/or one or more other lysins suitable for the treatment of Gram-positive bacteria depending on the infection of a given subject.

In one embodiment, lysin polypeptides of the present disclosure are capable of breaching or degrading a cell wall of Gram-negative bacteria. In a preferred embodiment, lysin polypeptides of the present disclosure are capable of breaching or degrading the cell wall of *P. aeruginosa.*

In some embodiments, the present disclosure provides a method of inhibiting the growth of one or more Gram-negative bacteria comprising administering to a subject or delivering to a particular environment one or more lysin polypeptides disclosed herein or a pharmaceutically acceptable composition thereof in an amount and under conditions such that the growth of Gram-negative bacteria is inhibited.

In another embodiment, the present disclosure provides a method of inhibiting the growth of *P. aeruginosa* and/or one or more other Gram-negative bacteria comprising administering to a subject one or more lysin polypeptides disclosed herein in combination with other clinically relevant agents.

In some embodiments, the present disclosure provides a method for increasing the permeability of an outer membrane of *P. aeruginosa* and/or one or more other Gram-negative bacteria by contacting the outer membrane with (exposing the bacteria to) one or more lysin polypeptides of the present disclosure.

In a further embodiment, the present disclosure provides a method for increasing the permeability of an outer membrane of *P. aeruginosa* and/or one or more other Gram-negative bacteria by contacting the outer membrane with lysin polypeptides disclosed herein in combination with other clinically relevant agents, such as antibiotics, bactericidal agents, anticeptics, etc.

In some embodiments, the present disclosure provides a method of augmenting antibiotic activity of one or more antibiotics against Gram-negative bacteria compared to the activity of said antibiotics used alone by administering to a subject one or more lysin polypeptides disclosed herein together with an antibiotic of interest. The combination is effective against bacteria and permits resistance against the antibiotic to be overcome and/or the antibiotic to be employed at lower doses, decreasing undesirable side effects, such as the nephrotoxic and neurotoxic effects of polymyxin B.

The compounds of the present disclosure can be used alone or in combination with additional permeabilizing agents of the outer membrane of the Gram-negative bacteria, including, but not limited to metal chelators as e.g. EDTA, TRIS, lactic acid, lactoferrin, polymyxins, citric acid (Vaara M. *Microbiol Rev.* 56(3):395-441 (1992)).

In one embodiment, the lysin polypeptides of the present disclosure are chemically modified. A chemical modification inludes but is not limited to, adding chemical moieties, creating new bonds, and removing chemical moieties. Chemical modifications can occur anywhere in a lysin polypeptide, including the amino acid side chains, as well as the amino or carboxyl termini. Such modification can be present at more than one site in a lysin polypeptide. Furthermore, one or more side groups, or terminal groups of a lysin polypeptide may be protected by protective groups known to the person ordinarily-skilled in the art.

In some embodiments, lysin polypeptides contain an attachment of duration enhancing moieties. In one embodiment, the duration enhancing moiety is polyethylene glycol. Polyethylene glycol ("PEG") has been used to obtain therapeutic polypeptides of enhanced duration (Zalipsky, S., *Bioconjugate Chemistry,* 6:150-165 (1995); Mehvar, R., *J.*

*Pharm. Pharmaceut. Sci.*, 3:125-136 (2000)). The PEG backbone [(CH$_2$CH$_2$—O—)$_n$, n: number of repeating monomers] is flexible and amphiphilic. When attached to another chemical entity, such as a lysin polypeptide, PEG polymer chains can protect such lysin polypeptide from immune response and other clearance mechanisms. As a result, pegylation can lead to improved lysin polypeptide efficacy and safety by optimizing pharmacokinetics, increasing bioavailability, and decreasing immunogenicity and dosing amount and/or frequency. "Pegylation" refers to conjugation of a PEG molecule with another compound, e.g. lysin polypeptide.

In one embodiment, the present disclosure relates to the prevention, reduction, treatment, or removal of Gram-negative bacterial contamination of medical devices, surfaces such as floors, stairs, walls and countertops in hospitals and other health related or public use buildings and surfaces of equipment in operating rooms, emergency rooms, hospital rooms, clinics, and bathrooms and the like. Examples of medical devices that can be protected using compositions described herein include but are not limited to tubings and other surface medical devices, such as urinary catheters, mucous extraction catheters, suction catheters, umbilical cannulae, contact lenses, intrauterine devices, intravaginal and intraintestinal devices, endotracheal tubes, bronchoscopes, dental prostheses and orthodontic devices, surgical instruments, dental instruments, tubings, dental water lines, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. The devices may include electrodes, external prostheses, fixation tapes, compression bandages, and monitors of various types. Medical devices can also include any device which can be placed at the insertion or implantation site such as the skin near the insertion or implantation site, and which can include at least one surface which is susceptible to colonization by Gram-negative bacteria.

In one embodiment, the lysin polypeptides of the present disclosure are used for preserving food against Gram-negative bacterial contamination comprising adding to the food the compositions of the present disclosure comprising lysin polypeptides. Examples of such food products are meat products (cured and/or uncured, fresh and/or cooked), salads and other vegetable products, drinks and dairy products, semi-processed foods, convenient foods as e.g. ready-to-eat meals and dried food products, etc.

One of the problems that bacteria pose towards humans is the formation of biofilms. Biofilm formation occurs when microbial cells adhere to each other and are embedded in a matrix of extracellular polymeric substance (EPS) on a surface. The growth of microbes in such a protected environment that is enriched with biomacromolecules (e.g. polysaccharides, nucleic acids and proteins) and nutrients allow for enhanced microbial cross-talk and increased virulence. As biofilm may develop in any supporting environment, a method or composition that can prevent or remove biofilm formation is needed. *Pseudomonas aeruginosa* has been shown to form biofilms on a variety of living and non-living surfaces such as the mucus plugs of the CF lung, contaminated catheters, contact lenses, etc (Sharma et al. *Biologicals,* 42(1):1-7 (2014)). Thus, in one embodiment, the lysin polypeptides of the present disclosure can be used for prevention, control, disruption, and treatment of bacterial biofilm, particulary those formed by or with the contribution of *P. aeruginosa.*

The lysin polypeptides of the present disclosure can be used in vivo, for example, to treat bacterial infections in a subject, as well as in vitro, for example to treat cells (e.g., bacteria) in culture to eliminate or reduce the level of bacterial contamination of a cell culture.

Methods for Producing Lysin Polypeptides

In one embodiment, the present disclosure includes methods for producing lysin polypeptides of the present disclosure which kill or inhibit the growth of one or more Gram-negative bacteria, preferably *P. aeruginosa*, the method comprising culturing a host cell comprising a lysin polynucleotide encoding one or more lysin polypeptides under suitable conditions to express the said polypeptide.

To obtain high level of lysin polypeptide expression, lysin polynucleotide sequences are typically expressed by operatively linking them to an expression control sequence in an appropriate expression vector and employing that expression vector to transform an appropriate cellular host. Such operative linking of a polynucleotide sequences encoding lysin polypeptides of the present disclosure to an expression control sequence, includes, the provision of an initiation codon, ATG, in the correct reading frame upstream of the polynucleotide (DNA) sequence. Generally, any system or vector suitable to maintain, propagate or express polynucleotides and/or to express a polypeptide in a host may be used for expression of lysin polypeptides. The appropriate DNA/polynucleotide sequence may be inserted into the expression system by any of a variety of well-known and routine techniques, such as, for example, those set forth in Sambrook et al., Molecular Cloning, A Laboratory Manual. Additionally, tags can also be added to lysin polypeptides to provide convenient methods of isolation, e.g., c-myc, biotin, poly-His, etc. Kits for such expression systems are commercially available.

A wide variety of host/expression vector combinations may be employed in expressing the polynucleotude sequences encoding lysin polypeptides of the present disclosure. Large numbers of suitable vectors are known to those of skill in the art, and are commercially available. Examples of suitable vectors are provided in Sambrook et al, eds., Molecular Cloning: A Laboratory Manual (3rd Ed.), Vols. 1-3, Cold Spring Harbor Laboratory (2001). Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Furthermore, said vectors may provide for the constitutive or inducible expression of lysin polypeptides of the present disclosure. More specifically, suitable vectors include but are not limited to derivatives of SV40 and known bacterial plasmids, e.g., *E. coli* plasmids colE1, pCR1, pBR322, pMB9 and their derivatives, plasmids such as RP4, pBAD24 and pBAD-TOPO; phage DNAS, e.g., the numerous derivatives of phage λ, e.g., NM989, and other phage DNA, e.g., M13 and filamentous single stranded phage DNA; yeast plasmids such as the 2 D plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Many of the vectors mentioned above are commercially available from vendors such as New England Biolabs, Addgene, Clontech, Life Technologies etc many of which also provide suitable host cells).

Additionally, vectors may comprise various regulatory elements (including promoter, ribosome binding site, terminator, enhancer, various cis-elements for controlling the expression level) wherein the vector is constructed in accordance with the host cell. Any of a wide variety of expression control sequences (sequences that control the expression of a polynucleotide sequence operatively linked to it) may be used in these vectors to express the polynucleotide sequences encoding lysin polypeptides. Useful control sequences include, but are not limited to: the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, $E.\ coli$ promoter for expression in bacteria, and other promoter sequences known to control the expression of genes of prokaryotic or eukaryotic cells or their viruses, and various combinations thereof.

A wide variety of host cells are useful in expressing the lysin polypeptides of present disclosure. Nonlimiting examples of host cells suitable for expression of lysin polypeptides of the present disclosure include well known eukaryotic and prokaryotic hosts, such as strains of $E.\ coli$, $Pseudomonas$, $Bacillus$, $Streptomyces$, fungi such as yeasts, and animal cells, such as CHO, R1.1, B—W and L-M cells, African Green Monkey kidney cells (e.g., COS 1, COS 7, BSC1, BSC40, and BMT10), insect cells (e.g., Sf9), and human cells and plant cells in tissue culture. While the expression host may be any known expression host cell, in a preferred embodiment the expression host is one of the strains of $E.\ coli$ These include, but are not limited to commercially available $E.\ coli$ strains such as Top10 (Thermo Fisher Scientific), DH5c (Thermo Fisher Scientific), XL1-Blue (Agilent Technologies), SCS110 (Stratagene), JM109 (Promega), LMG194 (ATCC), and BL21 (Thermo Fisher Scientific). There are several advantages of using $E.\ coli$ as a host system including: fast growth kinetics, where under the optimal environmental conditions, its doubling time is about 20 min (Sezonov et al., $J.\ Bacteriol.$ 189 8746-8749 (2007)), easily achieved high density cultures, easy and fast transformation with exogenous DNA, etc. Details regarding protein expression in $E.\ coli$, including plasmid selection as well as strain selection are discussed in details by Rosano, G. and Ceccarelli, E., $Front\ Microbiol.$, 5: 172 (2014).

Efficient expression of lysin polypeptides and vectors thereof depends on a variety of factors such as optimal expression signals (both at the level of transcription and translation), correct protein folding, and cell growth characteristics. Regarding methods for constructing the vector and methods for transducing the constructed recombinant vector into the host cell, conventional methods known in the art can be utilized. While it is understood that not all vectors, expression control sequences, and hosts will function equally well to express the polynucleotide sequences encoding lysin peptides of the present disclosure, one skilled in the art will be able to select the proper vectors, expression control sequences, and hosts without undue experimentation to accomplish the desired expression without departing from the scope of this disclosure. In some embodiments, the present inventors have found a correlation between level of expression and activity of the expressed polypeptide; in $E.$ $coli$ expression systems in particular, moderate levels of expression (for example between about 1 and 10 mg/liter) have produced lysin polypeptides with higher levels of activity than those that were expressed at higher levels in in $E.\ coli$ (for example between about 20 and about 100 mg/liter), the latter having sometimes produced wholly inactive polypeptides.

Lysin polypeptides of the present disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography can also employed for lysin polypeptide purification.

Alternatively, the vector system used for the production of lysin polypeptides of the present disclosure may be a cell free expression system. Various cell free expression systems are commercially available, including, but are not limited to those available from Promega, LifeTechnologies, Clonetech, etc.

As mentioned above, there is an array of choices when it comes to protein production and purification. Below, the inventors include by way of nonlimiting example a general protocol that can be used for the production of lysin polypeptides of the present disclosure in $E.\ coli$. Examples of suitable methods and strategies to be considered in protein production and purification are further provided in Structural Genomics Consortium, $Nat\ Methods.$, 5(2): 135-146 (2008). Exemplary Protocol:

1. DNA encoding lysin polypeptide is generated by total gene synthesis.
2. DNA fragments are next ligated into a preferably inducible vector such as pBAD24 (inducible with arabinose) and transformed into $E.\ coli$ cells (for example TOP10 from Invitrogen, Carlsbad, Calif.).
3. Transformed bacteria is spread on agar plates supplemented with broth, such as Lysogeny broth (LB), vector induction agent (e.g., 0.2% arabinose) and a selsctable marker (e.g., 50 µg/ml carbenicillin) and incubated preferably overnight at 37° C.
4. Single close cultures of $E.\ coli$ Top10 cells containing lysin plasmid are grown in broth supplemented with selectable marker (e.g., LB supplemented with 50 µg/ml carbenicillin) preferably overnight at 37° C. The culture may then be diluted for example 1:200 in fresh medium supplemented with selectable marker (e.g., LB supplemented with carbenicillin) and incubated for example for an additional 3 h. Lysin expression is induced with addition of the inducible agent (e.g., 0.2% L-arabinose), and the cells are inubated preferably overnight at 30° C.
5. Cell pellet is resuspended in buffer (e.g., 20 mM Tris, pH 6.8) and homogenized.
6. Protein solubilization and purification (using one or more chromatographic techniques) are performed in a well-buffered solution containing a suitable ionic strength of a monovalent salt, e.g., an ionic strength equivalent to 300-500 mM of NaCl.
7. Immobilized metal affinity chromatography (IMAC) is preferably used as the initial purification step. If additional purification is required, size-exclusion chromatography (gel filtration) can be used in a further step. If necessary, ion exchange chromatography can be used as a final step.

Identification of Lysin Polypeptides

The present disclosure is based on identification of five lysins with potent antibacterial activity against exponential phase *Pseudomonas aeruginosa* strain PAO1 (Examples 1 and 2). To identify the lysin polypeptides of the present disclosure, the inventors used a bioinformatics-based approach coupled with an antibacterial screen. Of the thus identified sequences, some were previously annotated as putative endolysins. However, the present inventors found that a substantial majority among them (they screened over 80 polypeptides) did not have any lysin activity or did not have activity against the target organism, *P. aeruginosa*. The five lysins identified as active were designated as GN37 (SEQ ID NO: 1), GN2 (SEQ ID NO: 2), GN4 (SEQ ID NO: 3), GN14 (SEQ ID NO: 4), and GN43 (SEQ ID NO: 5). Initially, the inventors evaluated the ability of purified lysins (which were synthesized, cloned into expression vector pBAD26, and then purified) to permeabilize the outer membrane (OM) of *P. aeruginosa*. (Example 1).

Most Gram-negative bacteria exclude hydrophobic compounds and do not allow the uptake of hydrophobic agents such asl-N-phenylnaphthylamine (NPN), crystal violet, or 8-anilino-1-naphthalenesulfonic acid (ANS). The strong resistance to hydrophobic compounds is due to the presence of outer membrane (OM), which contains associated proteins that anchor the OM to the peptidoglycan and keep it stable. Due to its hydrophobic nature, NPN fluoresces strongly under hydrophobic conditions and weakly under aqueous conditions (J Sokatch, The biology of *pseudomonas*, December 2012, Elsevier). Accordingly, NPN fluorescence can be used as a measurement of the outer membrane permeability.

In the present disclosure, the ability of numerous lysins (GN1, GN2, GN4, GNB, GN14, GN20, GN22, GN26, GN27, GN28, GN30, GN37, and GN43) to permeabilize the OM of *P. aeruginosa* strain PAO1 was tested by incubating NPN with PAO1 cells in the presence or absence of the above-mentioned lysins. As shown in FIG. 3, incubation of NPN in the presence of GN37 (SEQ ID NO: 1), GN2 (SEQ ID NO: 2), GN4 (SEQ ID NO: 3), GN14 (SEQ ID NO: 4), and GN43 (SEQ ID NO: 5) resulted in highest induction of fluorescence compared with fluorescence emitted without the presence of lysins (negative control). Moreover, each of the five lysins (GN2, GN4, GN14, GN37, and GN43) caused significantly stronger OM permeability compared to that caused by the established permeabilizing agent EDTA (ethylene diamine tetraacetate). Furthermore, each of the five lysins permeabilized the OM similarly to or better than a known antibiotic of last resort used in the treatment of *P. aeruginosa*, Polymyxin B (PMB). The active lysins of the present disclosure generally have a C-terminal (except GN14 which has an N-terminal) alpha-helix amphipathic domain varying in size between 15 amino acid residues for GN14 and 33 amino acid residues for GN43. Common features of GN2, GN4, GN14, GN37, and GN43 including the sequence of the alpha-helical amphipathic domain are included in Table 3. Secondary polypeptide structure can be determined using various software programs such as Jpred4 at www.compbio.dundee.ac.uk/jpred/. The amphipathic alpha helices in particular were examined using Helical Wheel (kael.net/helical.htm). Nucleic acid sequences of GN37 (SEQ ID NO: 11), GN2 (SEQ ID NO: 12), GN4 (SEQ ID NO: 13), GN14 (SEQ ID NO: 14), and GN43 (SEQ ID NO: 15) are also provided (FIG. 1A and FIG. 2).

TABLE 3

General features of each lysin polypeptide and sequences of the corresponding C-terminal alpha-helical amphipathic domains (Bolded and underlined region represents alpha-helical amphipathic domain).

GN2  hypothetical protein GOS_817346 [marine metagenome]
GenBank: EDG23390.1
147 amino acids, 16,700 Da, pI 6.16
50-75% identical to range of Gram-negative phage lysins
MKISLEGLSLIKKFEGCKLEAYKCSAGVWTIGYGHTAGVKEGDV
CTQEEAEKLLRGDIFKFEEYVQDSVKVDLDQSQFDALVAWTFNL
GPGNLRSSTMLKKLNNGEYESVPFEMRRWNKAGG**KTLDGLIRR
RQAESLLFESKEWH**QV (SEQ ID NO: 2)

GN4  putative endolysin [*Pseudomonas* phage PAJU2]
NCBI Reference Sequence: YP_002284361.1
144 amino acids, 16,199 Da, pI 9.58
>90% identical to a range of *P. aeruginosa* phage lysozymes and muramidases
MRTSQRGIDLIKSFEGLRLSAYQDSVGVWTIGYGTTRGVTRYMT
ITVEQAERMLSNDIQRFEPELDRLAKVPLNQNQWDALMSFVYNL
GAANLASSTLLKLLNKGDYQGAADQFP**RWVNAGGKRLDGLVKR
RAAERALFL**EPLS (SEQ ID NO: 3)

GN14 putative endolysin [*Pseudomonas* phage Lu11]
NCBI Reference Sequence: YP_006382555.1
189 amino acids, 20,380 Da, pI 9.14
>97% identical to only three *P. aeruginosa* phage lysins
MNNELPWVAEARKYIGLREDTSKTSHNPKLLAMLDRMGEFSNES
RAWWHDDETPWCGLFVGYCLGVAGRYVVREWYRARAWEAPQ
LTKLDRPAYGALVTFTRSGGGHVGFIVGKDARGNLMVLGGNQS
NAVSIAPFAVSRVTGYFWPSFWRNKTAVKSVPFEERYSLPLLKSN
GELSTNEA (SEQ ID NO: 4)

GN37 peptidase M15 [*Micavibrio aeruginosavorus*]
NCBI Reference Sequence: WP_014102102.1
126 amino acids, pI 9.69
MTYTLSKRSLDNLKGVHPDLVAVVHRAIQLTPVDFAVIEG
LRSVSRQKELVAAGASKTMNSRHLTGHAVDLAAYVNGIRW
DWPLYDAIAVAVKAAAKELGVAIVWGGDWTTF**KDGPHFELDRS
KYR** (SEQ ID NO: 1)

GN43 100% identical to MULTISPECIES: peptidase M23 [*Pseudomonas*]
NCBI Reference Sequence: WP_003085274.1
439 amino acids, 48,311 da, pI 9.55
MKRTTLNLELESNTDRLLQEKDDLLPQSVTNSSDEGTPFAQVEG
ASDDNTAEQDSDKPGASVADADTKPVDPEWKTITVASGDTLSTV
FTKAGLSTSAMHDMLTSSKDAKRFTHLKVGQEVKLKLDPKGEL
QALRVKQSELETIGLDKTDKGYSFKREKAQIDLHTAYAHGRITSS
LFVAGRNAGLPYNLVTSLSNIFGYDIDFALDLREGDEFDVIYEQH
KVNGKQVATGNILAARFVNRGKTYTAVRYTNKQGNTSYYRADGS
SMRKAFIRTPVDFARISSRFSLGRRHPILNKIRAHKGVDYAAPIG
TPIKATGDGKILEAGRKGGYGNAVVIQHGQRYRTIYGHMSRFAKG
IRAGTSVKQGQIIGYVGMTGLATGPHLHYEFQINGRHVDPLSAKL
PMADPIGGADRKRFMAQTQPMIARMDQEKKTLLALNKQR
(SEQ ID NO: 5)

Since GN2, GN4, GN14, GN37, and GN43 exhibited potent membrane-permeabilizing activity, the antibacterial activity of each of the five lysins against *P. aeruginosa* strain PAO1 was evaluated (Example 2). In addition to using EDTA and PMB as positive controls, human lysozyme and novobiocin were included as well. Human lysozyme (HuLYS) is a naturally occurring antimicrobial peptide found in a variety of tissues, cells, and secretions involved in the pathophysiology of lung infection (Callewaert et al. *J. Biosci.* 35:127-160 (2010)). It has been shown to be effective against both Gram-positive and Gram-negative organisms, including *P. aeruginosa* by degrading peptidoglycans in the bacterial cell wall. Novobiocin (Albamycin, Cathamycin, Spheromycin) is an aminocoumarin antibiotic isolated from *Streptomyces niveus*. It is mostly active against Gram-positive bacteria, but certain Gram-negative strains are also susceptible (Lindsey Grayson, Kucers' The Use of Antibiotics: A Clinical Review of Antibacterial, Antifungal and Antiviral Drugs, CRC Press 6th Edition, 2010).

Figure 4:
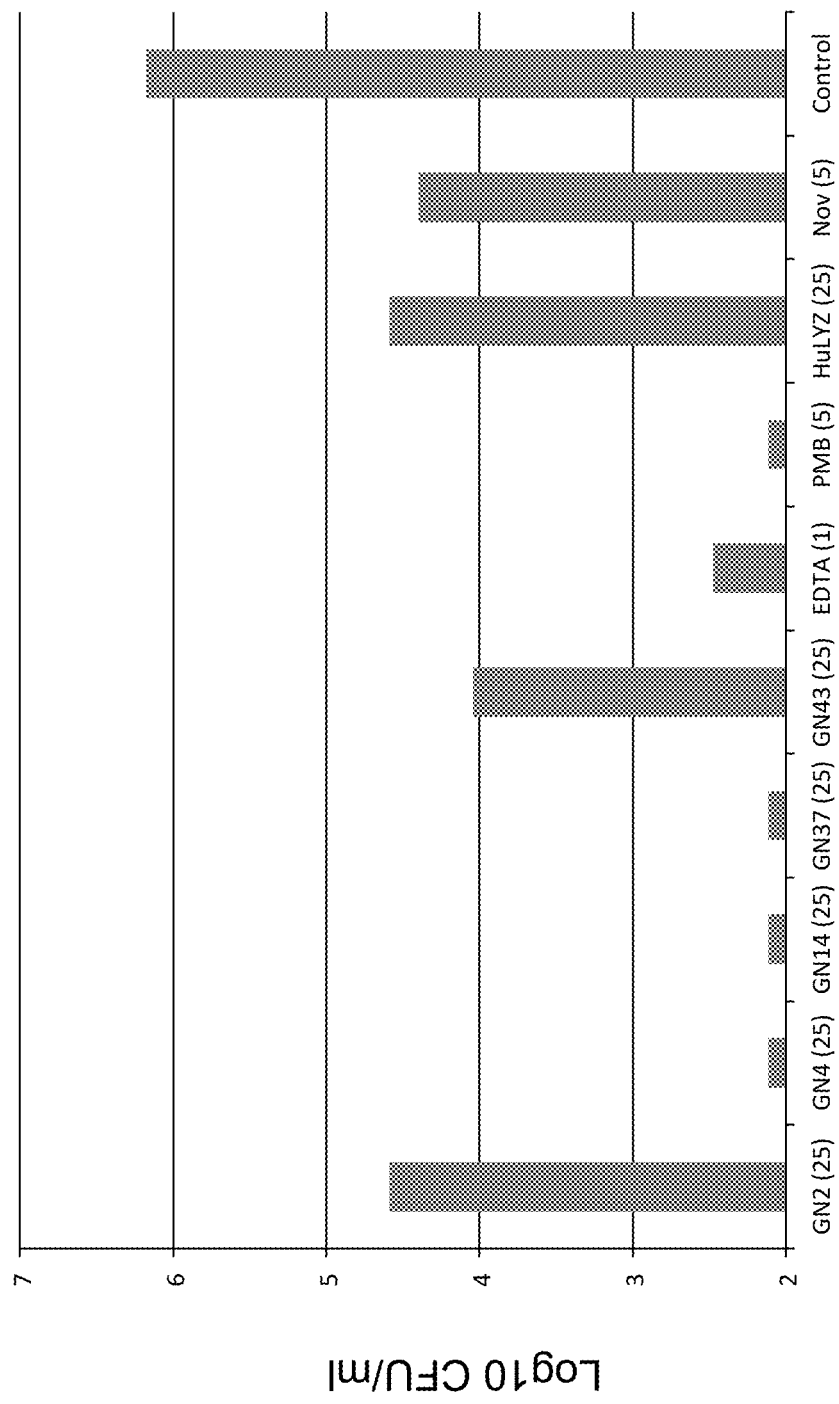
FIG. 4 is a bar graph showing antibacterial activity of GN lysin polypeptides against *P. aeruginosa* strain PAO1. The reduction in colony forming units (CFU) is presented on a logarithmic scale.

As shown in FIG. 4, all five lysins (GN2, GN4, GN14, GN37, and GN43) displayed greater antibacterial activity against *P. aeruginosa* strain PAO1 than either HuLYS or novobiocin alone, while GN4, GN14, and GN37 exhibited equivalent antibacterial activity to that of EDTA and PMB.

GN37 was derived from *Micavibrio aeruginosavorus*, a predator of *P. aeruginosa* that has not been previously used as a source of anti-*pseudomonas* PGH activities. The use of live *Micavibrio aeruginosavorus* has been suggested as a biological-based agent to control MDR *P. aeruginosa* (Dashiff et al. *J Appl.*, 110(2):431-44 (2011)). But to the inventors' knowledge there has been no report of using this organism as a source for individual antimicrobial proteins, PGHs, bacteriocins, antibiotics, etc. The inventors reasoned that an epibiotic predatory bacterium that attaches to the surface of *Pseudomonas aeruginosa* and extracts nutrients from within must encode an anti-*pseudomonas* PGH activity to pierce the outer membrane and cell wall. Based on this, the genomic sequence of *Micavibrio aeruginosavorus* strain ARL-13 was scanned for genes annotated as PGH-like enzymes. Five hydrolases were identified, cloned, and screened for anti-*pseudomonas* activity. The locus now designatated as GN37 was the only ORF which yielded a clearing zone (halo) on agar overlay plates. Thus, due to the unique source of GN37 and potent activity described in Example 3, GN37 was examined in further detail. As illustrated in Example 3, a multiple sequence alignment comparing GN37 to various known or putative lysins revealed that GN37 is only 67% identical to Mitrecin A (Farris and Steinberg, *Lett Appl Microbiol.*, 58(5):493-502 (2014); and patent publication US20140094401 A1). Unlike GN37, Mitrecin A was identified in the genome of the Gram-positive organism (i.e., *Streptomyces*). Furthermore, the activity described for Mitrecin A is very weak compared to that of GN37 (at roughly equivalent concentrations). Mitrecin A only achieved a <1-log decrease in bacterial viability over 16 hours of incubation (against *Yersinia pseudotuberculosis*), compared to the >3-log decrease after only 1 hour of GN37 treatment.

Figure 6:
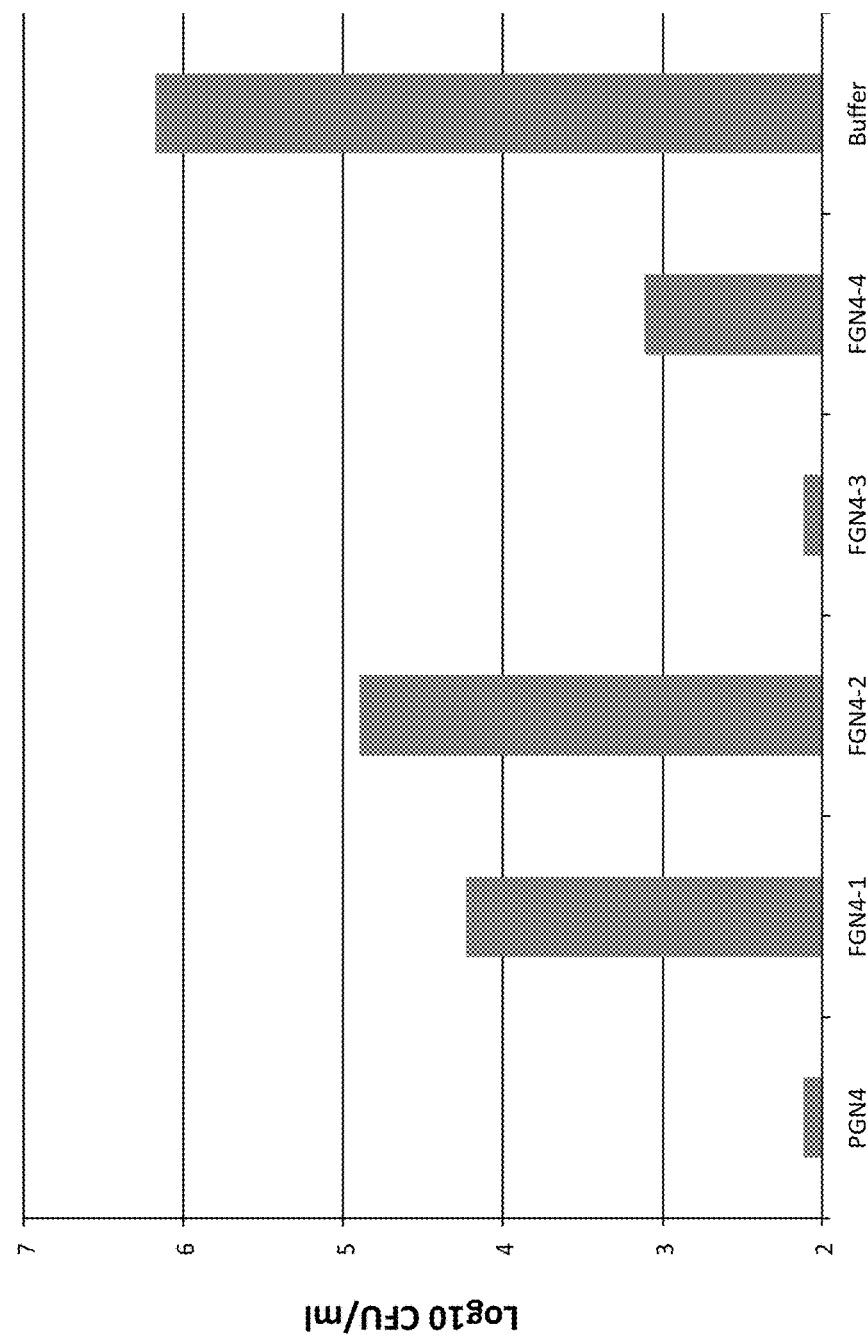
FIG. 6 is a bar graph showing the antibacterial activity of each GN4-derived lysin peptide (PGN4, FGN4-1, FGN4-2, FGN4-3, and FGN4-4) against *P. aeruginosa* strain PAO1. The reduction in CFU counts is presented along a logarithmic scale.

In addition to the full-length lysins disclosed here, the present disclosure provides peptide derivatives based on the C-terminal alpha-helical amphipathic domain of lysins of the present disclosure. Progressive truncation (amino acid deletion) of the C-terminal (and/or to of the N-terminal) of polypeptides comprising this domain can yield active lysin peptide fragments down to a minimum length active lysin peptide. Such peptides can be further modified by addition of one or more amino acids (other than those of the naturally occurring lysin) to the truncated C- (or N-) terminal in a manner not disrupting the alpha helix. Both C- and N-terminal alpha-helical amphipathic domains can be identified using bioinformatics approach. Examples of alpha helix nondisrupting amino acids are hydrophobic or charged residues that extend the alpha helical region or that promote membrane insertion Amino acid addition is further illustrated using the lysin polypeptide GN4 (Example 4, FIG. 5). While peptides FGN4-1 (SEQ ID NO: 7) and FGN4-2 (SEQ ID NO: 8) are peptide fragments of GN4 (SEQ ID NO: 3), PGN4 (SEQ ID NO: 6), FGN4-3 (SEQ ID NO: 9), and FGN4-4 (SEQ ID NO: 10) each contain a modification (FIG. 5), a viability assay indicated that PGN4 and FGN4-3 exhibit greater antibacterial activity than the other GN4 peptides tested (FIG. 6). PGN4-4 is a 39 amino acid polypeptide, which comprises a 31 amino acid polypeptide FGN4-2 and an 8-residue antibacterial peptide identified from the hepatitis B capsid (SQSRESQC) (amino acid numbers 32-39 of SEQ ID NO: 6). Thus, as seen in FIG. 6, the addition of SQSRESQC (amino acid numbers 32-39 of SEQ ID NO: 6) peptide augments the activity of FGN4-2. Comparison of the native fragment FGN4-1 and FGN4-4, which has a C-terminus cysteine (FGN4-4) added, indicates that the addition of cysteine to the C-terminus enhanced the activity of the FGN4-1. The cysteine was added to see if it would promote dimerization and augment activity. The results indicate that the terminal cysteine augments activity. Additional modifications include FGN4-2 in which 11 C-terminal residues are removed. These residues are not required for the alpha helical structure (based on secondary protein structure considerations) and the inventors probed to see whether activity would be maintained. Removal of all 11 residues did reduce activity but activity could be restored and in fact improved by other modifications, such as those described earlier in this paragraph. In light of the foregoing, those of ordinary skill can readily produce truncated lysins with their C-terminal alpha helical amphipathic domain intact by producing lysin polypeptides progressively lacking one or more amino acid residues from the C-terminal of this domain or from the N-terminal or both and testing such polypeptides alone or in combination with one or more antibiotics active against Gram-negative bacteria for activity against (i.e. ability to inhibit, reduce the population or kill) *P. aeruginosa* and/or another Gram-negative bacterium. Such testing can follow for example the teachings provided in Examples 2, 3, 4, or Prophetic Example 1. Of course, the testing procedures and protocols themselves are not limited to those in these Examples but can be any methods known to those skilled in the art for assessing effectiveness of an antibacterial and indeed an antimicrobial agent.

Figure 7:
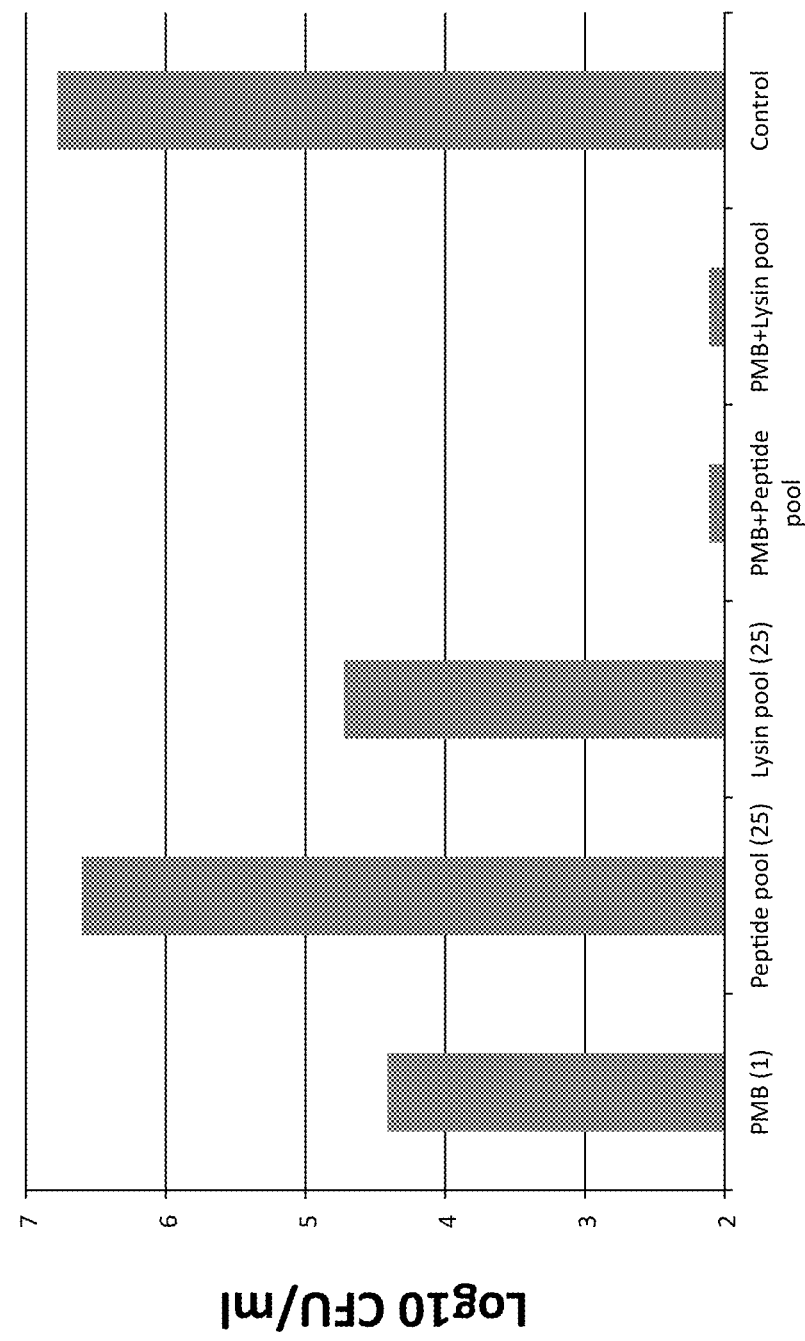
FIG. 7 is a bar graph showing the antibacterial activity in human serum of pooled GN lysin polypeptides and GN4-derived lysin peptides of the present disclosure against *P. aeruginosa* strain PAO1. The reduction in CFU counts is presented along a logarithmic scale.

For the analysis of antibacterial activity in human serum, the GN lysin polypeptides and GN peptides were each pooled in the presence and absence of sub-MIC concentration of polymyxin B (Example 5, FIG. 7). PMB is a potent antibiotic with activity against *P. aeruginosa* and, at a concentration of 1 mcg/ml, resulted in a <2-log 10 decrease in viability after treatment for 1 hour in human serum. The GN4 peptide pool (containing each peptide at 25 mcg/ml, labeled "peptide pool" in FIG. 7) alone did not result in decreased viability and the lysin polypeptide pool (containing each GN lysin at a concentration of 25 mcg/ml) alone resulted only in a <2-log 10 reduction in viability (FIG. 7). When combined with the PMB, however, both the peptide pool and the lysin pool resulted in a ≥4-log 10 decrease in viability (FIG. 7). These findings indicate a strong additive or even synergistic effect of the combination of PMB and the GN lysin polypeptides of the present disclosure. It is anticipated that individual lysin polypeptides will also result in a substantial decrease in viability of Gram-negative bacteria such as *P. aeruginosa* if used individually instead of in a pool. An observation regarding FIG. 7 is that the peptide pool alone is not as active as would have been predicted from FIG. 6. This is most likely due to the fact that biological activity of many antibacterial agents is diminished in the presence of human serum (Zhanel et al., *Antimicrob Agents Chemother.* 42(9): 2427-2430 (1998)). However, once the lysin pool is co-administered with PMB, the antibacterial activity of the lysin pool is restored, despite of the presence of serum (FIG. 7). Thus, the decrease in lysin pool antimicrobial activity in the presence of human serum may be due to the antagonistic activity among the peptides in the peptide pool that is no longer inhibitory in the presence of PMB. Alternatively, one or more proteins present in the human serum may have antagonistic effect on the lysin pool, wherein the effect is repressed upon the addition of PMB. The two possible scenarios can be distinguished by repeating the assay using individual lysin polypeptides, performing the assay in serum in the presence or absence of PMB, and comparing the results to those obtained using lysin pools. Furthermore, the inhibition of lysin pool activity in serum could be due to the high salt concentrations disrupting the electrostatinc interaction between lysin and outer membrane.

The GN lysin polypeptides of the present disclosure have bacterial activity distinct from traditional antibiotic, vaccine, and anti-toxin treatments and are useful to combat infections caused by Gram-negative bacteria. As described in the Examples, unlike other treatments lysins provide a rapid bactericidal and, when used in sub MIC amounts bacteriostatic effect, and are active against a range of antibiotic resistant bacteria, mirroring results previously obtained using specific lysins against Gram-positive bacteria including S. aureus, S. pyogenes, S. pneumoniae, B. anthracia, and B. cereus and have not been associated with evolving resistance (Fischetti, V. Curr Opin Microbiol., 11(5): 393-400 (2008)). Based on the present disclosure, in a clinical setting, lysins are a potent alternative for treating infections arising from drug- and multidrug-resistant bacteria. Existing resistance mechanisms for Gram-negative bacteria should not affect sensitivity to the PGH activity of lysins.

The lysin polypeptides of the present disclosure differ from existing PGHs under development for the treatment of Gram-negative infections. Previously described artilysins consist of positively charged PGHs fused to exogenously-derived cationic peptides (Briers et al., Antimicrob Agents Chemother. 58(7): 3774-84 (2014); Briers et al. MBio. 4:e01379-14 (2014); U.S. Pat. No. 8,846,865). Moreover, the artilysins use polycationic peptides that are not derived from endolysins. On the contrary, polycationic regions of lysin polypetides of the present disclosure are derived from lysins that naturally interact with and destabilize the OM of P. aeruginosa, a feature that is anticipated to result in improved targeting efficiency against this pathogen.

The lysin polypeptides of the present disclosure need not be modified by the addition of antimicrobial cationic peptides, although fusion polypeptides containing such peptides added to lysin polypeptides isolated and recombinantly generated as described herein are certainly being contemplated. However, even in the absence of added cationic or other antimicrobial (antibacterial) peptides, the lysin polypeptides of the present disclosure have substantial anti-Gram-negative antibacterial activity, including both bacteriostatic and bactericidal activity. The foregoing notwithstanding, the present disclosure also contemplates fusion lysin polypeptides comprising a lysin polypeptide having native Gram-negative antibacterial function fused to an antimicrobial peptide (AMP, defensin, sushi peptide, cationic peptide, polycationic peptide, amphipatic peptide, hydrophobic peptide) stretch such as those described in US Patent Application US2015/0118731_and International Patent Applications WO 2014/0120074, WO 2015/070912; WO 2015/071436; WO 2015/070911; WO.2015/071437; WO/2012/085259; WO 2014/001572, and WO 2013/0344055. Fusion polypeptides containing additional bactericidal segments, i.e., segments having bactericidal activity on their own prior to fusion or contributing positively to the bactericidal activity of the parent lysin polypeptide, are also contemplated.

Pharmaceutical Compositions and Preparations

The compositions of the present disclosure can take the form of solutions, suspensions, emulsion, tablets, pills, pellets, capsules, capsules containing liquids, powders, sustained-release formulations, suppositories, tampon applications emulsions, aerosols, sprays, suspensions, lozenges, troches, candies, injectants, chewing gums, ointments, smears, a time-release patches, a liquid absorbed wipes, and combinations thereof.

Administration of the compositions of the present disclosure or pharmaceutically acceptable forms thereof may be topical, i.e., the pharmaceutical composition is applied directly where its action is desired (for example directly to a wound), or systemic. In turn, systemic administration can be enteral or oral, i.e., substance is given via the digestive tract, parenteral, i.e., substance is given by other routes than the digestive tract such as by injection or inhalation. Thus, the lysin polypeptides of the present disclosure can be administered to a subject orally, parenterally, by inhalation, topically, rectally, nasally, buccally or via an implanted reservoir or by any other known method. The lysin polypeptides of the present disclosure can also be administered by means of sustained release dosage forms.

For oral administration, the lysin polypeptides of the present disclosure can be formulated into solid or liquid preparations, for example tablets, capsules, powders, solutions, suspensions and dispersions. The compound can be formulated with excipients such as, e.g., lactose, sucrose, corn starch, gelatin, potato starch, alginic acid and/or magnesium stearate.

For preparing solid compositions such as tablets and pills, a lysin polypeptide of the present disclosure or a fragment thereof is mixed with a pharmaceutical excipient to form a solid preformulation composition. If desired, tablets may be sugar coated or enteric coated by standard techniques. The tablets or pills may be coated or otherwise compounded to provide a dosage form affording the advantage of prolonged action. For example, the tablet or pill can include an inner dosage and an outer dosage component, the latter being in the form of an envelope over the former. The two components can be separated by enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The topical compositions of the present disclosure may further comprise a pharmaceutically or physiologically acceptable carrier, such as a dermatologically or an otically acceptable carrier. Such carriers, in the case of dermatologically acceptable carriers, are preferably compatible with skin, nails, mucous membranes, tissues and/or hair, and can include any conventionally used dermatological carrier meeting these requirements. In the case of otically acceptable carriers, the carrier is preferably compatible with all parts of the ear. Such carriers can be readily selected by one of ordinary skill in the art. Carriers for topical administration of the compounds of the present disclosure include, but are not limited to, mineral oil, liquid petroleum, white petroleum, propylene glycol, polyoxyethylene and/or polyoxypropylene compounds, emulsifying wax, sorbitan monostearate, polysorbate 60, cetyl esters wax, cetearyl alcohol, 2-octyldodecanol, benzyl alcohol, and water. In formulating skin ointments, the active components of the present disclosure may be formulated in an oleaginous hydrocarbon base, an anhydrous absorption base, a water-in-oil absorption base, an oil-in-water water-removable base and/or a water-soluble base. In formulating otic compositions, the active components of the present disclosure may be formulation in an aqueous polymeric suspension including such carriers as dextrans, polyethylene glycols, polyvinylpyrrolidone, polysaccharide gels, Gelrite®, cellulosic polymers like hydroxypropyl methylcellulose, and carboxy-containing polymers such as polymers or copolymers of acrylic acid, as well as other polymeric demulcents. The topical compositions according to the present disclosure may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (OAV or oil in water) or, conversely, (W/O or water in oil), microemulsions or alternatively microcapsules, microparticles or lipid vesicle dispersions of ionic and/or nonionic type, creams, lotions, gels, foams (which will generally require a pressurized canister, a sutiable applicator an emulsifier and an inert propellant), essences, milks, suspensions, or patches. Topical compositions of the present disclosure may also contain adjuvants such as hydrophilic or lipophilic gelling agents, hydrophilic or lipophilic active agents, preserving agents, antioxidants, solvents, fragrances, fillers, sunscreens, odor-absorbers and dyestuffs. In a further aspect, the topical antibacterial compositions may be administered in conjunction with devices such as transdermal patches, dressings, pads, wraps, matrices and bandages capable of being adhered or otherwise associated with the skin or other tissue of a subject, being capable of delivering a therapeutically effective amount of one or more antibacterial lysin polypeptides in accordance with the present disclosure.

In one embodiment, the topical compositions of the present disclosure additionally comprise one or more components used to treat topical burns. Such components typically include, but are not limited to, a propylene glycol hydrogel; a combination of a glycol, a cellulose derivative and a water soluble aluminum salt; an antiseptic; an antibiotic; and a corticosteroid. Humectants (such as solid or liquid wax esters), absorption promoters (such as hydrophilic clays, or starches), viscocity building agents, and skin-protecting agents may also be added. Topical formulations may be in the form of rinses such as mouthwash. See, e.g., WO2004/004650.

The compounds of the present disclosure may also be administered by injection of a therapeutic agent comprising the appropriate amount of lysin polypeptide and a carrier. For example, the lysin polypeptides can be administered intramuscularly, intrathecally, subdermally, subcutaneously, or intravenously to treat infections by Gram-negative bacteria, more specifically those caused by *P. aeruginosa*. The carrier may be comprised of distilled water, a saline solution, albumin, a serum, or any combinations thereof. Additionally, pharmaceutical compositions of parenteral injections can comprise pharmaceutically acceptable aqueous or nonaqueous solutions of lysin polypeptides in addition to one or more of the following: pH buffered solutions, adjuvants (e.g., preservatives, wetting agents, emulsifying agents, and dispersing agents), liposomal formulations, nanoparticles, dispersions, suspensions or emulsion, s as well as sterile powders for reconstitution into sterile injectable solutions or dispersions just prior to use.

In cases where parenteral injection is the chosen mode of administration, an isotonic formulation is preferably used. Generally, additives for isotonicity can include sodium chloride, dextrose, mannitol, sorbitol, and lactose. In some cases, isotonic solutions such as phosphate buffered saline are preferred. Stabilizers can include gelatin and albumin. A vasoconstriction agent can be added to the formulation. The pharmaceutical preparations according to this type of application are provided sterile and pyrogen free.

The diluent may further comprise one or more other excipient such as, e.g., ethanol, propylene glycol, an oil or a pharmaceutically acceptable emulsifier or surfactant.

In another embodiment, the compositions of the present disclosure are inhalable compositions. The inhalable compositions of the present disclosure can further comprise a pharmaceutically acceptable carrier. In one embodiment, lysin polypeptide(s) of the present disclosure are advantageously formulated as a dry, inhalable powder. In specific embodiments, lysin polypeptides inhalation solution may further be formulated with a propellant for aerosol delivery. In certain embodiments, solutions may be nebulized.

A surfactant can be added to an inhalable pharmaceutical composition of the present disclosure in order to lower the surface and interfacial tension between the medicaments and the propellant. Where the medicaments, propellant and excipient are to form a suspension, a surfactant may or may not be required. Where the medicaments, propellant and excipient are to form a solution, a surfactant may or may not be necessary, depending in part, on the solubility of the particular medicament and excipient. The surfactant may be any suitable, non-toxic compound which is non-reactive with the medicament and which substantially reduces the surface tension between the medicament, the excipient and the propellant and/or acts as a valve lubricant.

Examples of suitable surfactants include, but are not limited to: oleic acid; sorbitan trioleate; cetyl pyridinium chloride; soya lecithin; polyoxyethylene(20) sorbitan monolaurate; polyoxyethylene (10) stearyl ether; polyoxyethylene (2) oleyl ether; polyoxypropylene-polyoxyethylene ethylene diamine block copolymers; polyoxyethylene(20) sorbitan monostearate; polyoxyethylene(20) sorbitan monooleate; polyoxypropylene-polyoxyethylene block copolymers; castor oil ethoxylate; and combinations thereof.

Examples of suitable propellants include, but are not limited to: dichlorodifluoromethane, trichlorofluoromethane, dichloro-tetrafluoroethane and carbon dioxide.

Examples of suitable excipients for use in inhalable compositions include, but are not limited to: lactose, starch, propylene glycol diesters of medium chain fatty acids; triglyceride esters of medium chain fatty acids, short chains, or long chains, or any combination thereof; perfluorodimethylcyclobutane; perfluorocyclobutane; polyethylene glycol; menthol; lauroglycol; diethylene glycol monoethylether; polyglycolized glycerides of medium chain fatty acids; alcohols; *eucalyptus* oil; short chain fatty acids; and combinations thereof.

In some embodiments, the compositions of the present disclosure comprise nasal applications. Nasal applications include for instance nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application.

In another embodiment, the pharmaceutical compositions of the present disclosure contain a complementary agent, including one or more antimicrobial agents and or one or more conventional antibiotics. In order to accelerate the treatment of the infection, or augment the antibacterial effect, the therapeutic agent containing one or more lysin polypeptides of the present disclosure may further include at least one complementary agent which can also potentiate the bactericidal activity of the lysin polypeptide. The complementary agent may be one or more antibiotics used to treat Gram-negative bacteria. In preferred embodiment, the complementary agents is an antibiotic or antimicrobial agents used for the treatment of infections caused by *P. aeruginosa*.

Dosage and Frequency of Administration to Subjects

The compositions of the present disclosure may be presented in unit dosage form and may be prepared by any methods well known in the art. The amount of active ingredients which can be combined with a carrier material to produce a single dosage form will vary depending upon the host being treated, the duration of exposure of the recipient to the infectious bacteria, the size and weight of the subject, and the particular mode of administration. The amount of active ingredients that can be combined with a carrier material to produce a single dosage form will generally be that amount of each compound which produces a therapeutic effect. Generally, out of one hundred percent, the total amount will range from about 1 percent to about ninety-nine percent of active ingredients, preferably from about 5 percent to about 70 percent, most preferably from about 10 percent to about 30 percent.

Dosages administered depend on a number of factors including the activity of infection being treated, the age, health and general physical condition of the subject to be treated, the activity of a particular lysin polypeptide, the nature and activity of the antibiotic if any with which a lysin polypeptide according to the present disclosure is being paired and the combined effect of such pairing. Generally, effective amounts of the present lysin polypeptides to be administered are anticipated to fall within the range of 1-50 mg/kg administered 1-4 times daily for a period up to 14 days. The antibiotic if one is also used will be administered at standard dosing regimens or in lower amounts. All such dosages and regimens however (whether of the lysin polypeptide or any antibiotic administered in conjunction therewith) are subject to optimization. Optimal dosages can be determined by performing in vitro and in vivo pilot efficacy experiments as is within the skill of the art, but taking the present disclosure into account.

In some embodiments, time exposure to the active lysin polypeptide(s) units may influence the desired concentration of active lysin polypeptide units per ml. Carriers that are classified as "long" or "slow" release carriers (such as, for example, certain nasal sprays or lozenges) could possess or provide a lower concentration of lysin polypeptide units per ml, but over a longer period of time, whereas a "short" or "fast" release carrier (such as, for example, a gargle) could possess or provide a high concentration of lysin polypeptide units per ml, but over a shorter period of time. There are circumstances where it may be necessary to have a much higher unit/ml dosage or a lower unit/ml dosage.

For any lysin polypeptide of the present disclosure, the therapeutically effective dose can be estimated initially either in cell culture assays or in animal models, usually mice, rabbits, dogs, or pigs. The animal model can also be used to achieve a desirable concentration range and route of administration. Obtained information can then be used to determine the effective doses, as well as routes of administration in humans. Dosage and administration can be further adjusted to provide sufficient levels of the active ingridient or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy and the judgment of the treating physician.

A treatment regimen can entail daily administration (e.g., once, twice, thrice, etc. daily), every other day (e.g., once, twice, thrice, etc. every other day), semi-weekly, weekly, once every two weeks, once a month, etc. In one embodiment, treatment can be given as a continuous infusion. Unit doses can be administered on multiple occasions. Intervals can also be irregular as indicated by monitoring clinical symptoms. Alternatively, the unit dose can be administered as a sustained release formulation, in which case less frequent administration is required. Dosage and frequency may vary depending on the patient. It will be understood by one of skill in the art that such guidelines will be adjusted for localized administration, e.g. intranasal, inhalation, rectal, etc., or for systemic administration, e.g. oral, rectal (e.g., via enema), i.m. (intramuscular), i.p. (intraperitoneal), i.v. (intravenous), s.c. (subcutaneous), transurethral, and the like.

EXAMPLES

Example 1

Identification of Gram Negative Lysins

Putative PGH candidates, that may be used to kill Gram-negative bacteria, were identified using a bioinformatics search protocol. First, the inventors generated a short list of *P. aeruginosa* PGHs obtained from annotated genome sequences that were screened with search terms for bacteriophage lysins, including "amidase", "lysozyme", "glucosaminidase", "endopeptidase", "peptidoglycan hydrolase", "lytic transglycosylase", "endolysin", "lysin", and "cell wall hydrolase". The PGHs identified in this manner were then used to search, by BLASTP analysis, all *P. aeruginosa* genome sequences in GenBank (*P. aeruginosa* group; Taxid: 136841) and the genomic sequence of *Micavibrio aeruginosavorus* strain ARL-13 to generate a larger group of putative PGHs. A subset of this group, comprised of 46 PGHs, was then chosen for further study—the criteria for inclusion here was diversity with respect to sequence conservation and including both highly and poorly conserved enzymes with a range of putative catalytic/cell wall binding activities. The 46 PGHs were synthesized, cloned into the bacterial expression vector pBAD24 (Guzman et al., *J Bacteriol*. (14):4121-30 (1995)), and transformed into *E. coli* strain Top10 (Life Technologies). To assess activity, all *E. coli* clones (including vector controls) were screened using a plate-based assay for lytic activity against *P. aeruginosa* strain PAO1. Positive clones were then further analysized with respect to the induction of soluble protein in liquid LB cultures in the manner described (Schuch et al., *Nature*, 418 (6900):884-9, (2002)). For the soluble and active lysins, crude *E. coli* extracts of induced cultures were then examined for the ability to induce permeabilizaton of P. aeruguinosa strain PAO1 using the hydrophobic fluorescent probe 1-N-phenylnaphtthylmine (NPN). The NPN assay is a standard method (Helander and Mattila-Sandholm, *J Appl Microbiol.*, 88(2):213-9. (2000)) to screen for compounds that disrupt the bacterial outer membrane. This screening approach ultimately yielded 5 candidate PGHs (with N- and C-terimnal alpha helical domains) in the genomes of Pseudomonas aeruginosa strains, and other Gram-negative organisms (including *Micavibrio aeruginosavorus*), as well as those identified using marine metagenomics. The resulting proteins were then tested for their antibacterial activity against *P. aeruginosa* strain PAO1, which is resistant to penem antibiotics (Okamoto et al. *Antimicrob Agents Chemother.* 45(7):1964-71 (2001)).

In order to evaluate the activity of purified lysins, the uptake of hydrophobic fluorescent probe 1-N-phenylnaphtthylmine (NPN) by *P. aeruginosa* strain PAO1 was examined Since the outer membrane of Gram-negative bacteria acts as a permeability barrier to hydrophobic compounds, including lysins and NPN, the permeabilizing activity of GNs can be and was evaluated by the ability of hydrophobic compound to reach the inner target. Thus, while NPN is normally excluded by the outer membrane, it exhibits prominent fluorescence intensity when it partitions into the outer membrane lipid bilayer.

*P. aeruginosa* PAO1 was obtained from the American Type Culture Collection (ATCC). Bacteria were cultured at initial concentration of $10^5$ CFU/ml in LB medium (Sigma-Aldrich) in a shaker-incubator at 37° C. and 250 r.p.m. *P. aeruginosa* culture was grown to the beginning of exponential phase (A550~0.3) to which each of the candidate lysins (GNs) was added at a concentration of 10 mcg/ml. To measure the uptake of NPN, 10 μM NPN was added to exponentially growing cells containing GN1, GN2, GN4, GNB, GN14, GN20, GN22, GN26, GN27, GN28, GN30, GN37, and GN43 in PBS and fluorescence was monitored at 420 nm at 1 hour with a fluorescence spectrophotometer (FIG. 3). Antibiotic polymyxin B (5 mcg/ml) and EDTA (1 mM) were used as positive controls, while cells treated with NPN but without the addition of lysin served as a negative control.

As shown in FIG. 3, a strong fluorescent signal was observed when *P. aeruginosa* cells were treated with GN2 (SEQ ID NO: 2), GN4 (SEQ ID NO: 3), GN14 (SEQ ID NO: 4), GN37 (SEQ ID NO: 1), or GN43 (SEQ ID NO: 5) in the presence of NPN (grey bars). The general features of each lysin are shown in Table 4.

Collectively, these results identify a group of GN lysins that exhibit an ability to permeate the OM of Gram-negative bacteria, establishing a first step in identifying lysins active against Gram-negative bacteria without the need to resort to addition of heterologous peptide segments.

Example 2

GN Lysins Exhibit Strong Antibacterial Activity Against Gram-Negative Bacteria

In order to evaluate the antibacterial activity of purified lysins, the viability of live *P. aeruginosa* strain PAO1 following the incubation with individual GN lysins was evaluated. Briefly, $10^6$ PAO1 cells were treated with the indicated GN lysin at a concentration of 25 mcg/ml for 1 hour (at 37° C., without agitation) in the presence of 20 mM Tris-HCl (pH 7.2) buffer. Polymyxin B (PMB, at 25 mcg/ml), novobiocin (Nov, at 5 mcg/ml), EDTA (1 mM) and human lysozyme (HuLYZ, at 25 mcg/ml) were used as controls. The threshold of detection was 2.0 Log 10 CFU/ml.

As FIG. 4 shows, each GN lysin exhibited greater antibacterial activity than either HuLYZ or novobiocin, while each of GN4 (SEQ ID NO: 3), GN14 (SEQ ID NO: 4), and GN37 (SEQ ID NO: 1) showed stronger or equivalent antibacterial activity when compared to EDTA and PMB respectively.

This experiment demonstrates that GNs can exhibit equivalent or greater antibacterial activity than any of conventional antibiotics, human lysozyme or the chelating agent EDTA against Gram-negative bacteria.

Example 3

GN37 is Highly Effective Gram-Negative Antibacterial Agent

GN37 lysin is a 126 amino acid polypeptide (FIG. 1A) encoded by the 381-bp MICA_542 locus of *Micavibrio aeruginosavorus*. *M. aeruginosavorus* is a predator of *P. aeruginosa* and has not been previously exploited as a source of anti-*pseudomonas* PGH activities. The GN37 lysin is a highly positively charged protein with a predicted pI of 9.69. Additionally, GN37 is a member of the Peptidase_M15_4 family of PGHs with DD- and DL-carboxypeptidase activities (including members of the VanY superfamily) (FIG. 1B). Based on BLASTP analysis, GN37 (SEQ ID NO: 1) is ≤67% [identical to proteins from >50 different Gram-negative species and 1 Gram-positive bacterium species. A multiple sequence alignment is shown in FIG. 1C comparing GN37 to the Gram-positive homolog (from *Streptomyces*, GenBank sequence AGJ50592.1) and proteins from Gram-negative pathogens including *E. coli* (WP_001117823.1 and NP_543082.1), *Yersinia* spp. (CAJ28446.1) and *Acinetobacter baumannii*,

TABLE 4

General Features of G2, GN4, GN14, GN37, and GN43.

| Lysin | Size (aa) | pI | Class | Source | GenBank Accession | Homology | Feature |
|---|---|---|---|---|---|---|---|
| GN2 | 147 | 6.16 | Lysozyme | Marine metagenome | EDG23390.1 | 50-75% range of Gram- lysins | α-helical C-terminus |
| GN4 | 144 | 9.58 | Lysozyme | Pseudomonas phage PAJU2 | YP_002284361.1 | >90% (Pa phage lysins) | α-helical C-terminus |
| GN14 | 189 | 9.14 | NLPC_P60 | Pseudomonas phage PAJU2 | YP_006382555.1 | >97% to 3 Pa phage lysins | Amidase? |
| GN37 | 126 | 9.69 | Peptidase_M15_4 | Micavibrio aeruginosavorus | WP_014102102.1 | ≤67% to bacteriocin and G- petidases | Large α-helical N- terminal binding domain |
| GN43 | 439 | 9.55 | LysM-Peptidase_M 23 | Pseudomonas Spp. | PaerPAb_03459 | ≤100% to range of pseudomonas peptidases | Multi domain |

(WP_034684053.1). Importantly, there are no sequences in the public database with >67% identity to GN37.

Example 4

Peptide Derivatives of GN4 Exhibit Potent Antibacterial Activity

In addition to the full-length lysins, five peptide derivatives of GN4 (corresponding to an alpha-based helical C-terminal fragment) were also generated and examined (FIG. 5). The first peptide (FGN4-1, (SEQ ID NO: 7)) corresponds to a 42 amino acid C-terminal alpha-helical domain. This was arrived at taking into account protein secondary structure predictions that this region was sufficient to generate the C-terminal alpha-helical amphipathic domain of GN4 (alternatively it could have been arrived at by progressive truncation of the very end of the C-terminal and testing the effect on activity each time). The rationale for the additional modifications has been described elsewhere in the specification A single C-terminal cysteine was added to FGN4-1 (SEQ ID NO: 7) to generate FGN4-4 (SEQ ID NO: 10). For the 3 additional peptides, the 11 C-terminal residues of FGN4-1 were either removed (FGN4-2, (SEQ ID NO: 8)) or removed and replaced with either a single lysine (K) residue (FGN4-3, (SEQ ID NO: 9)) or an 8-residue antibacterial peptide identified from the hepatitis B capsid (PGN4, (SEQ ID NO: 6)). The hepatitis B peptide is SQSRESQC (amino acid numbers 32-39 of SEQ ID NO: 6) and has Epitope ID number 96916 from the Immune Epitope Database. The antibacterial activity of each GN4-derived peptide was examined in a killing assay (FIG. 6), where $10^5$ PAO1 cells were treated with the indicated peptide derivative at a concentration of 10 mcg/ml for 1 hour (at 37° C., without agitation) in the presence of 20 mM Tris-HCl (pH 7.2) buffer. The threshold of detection was 2.0 log 10 CFU/ml. As illustrated in FIG. 6, each of the tested peptides showed some antibacterial activity (compared to the buffer that served as a negative control), whereas FGN4-1 and FGN4-4 exhibited superior activity, with a ≥4 log decrease in cell viability.

Example 5

GN Lysins and GN Peptides Display Robust Antibacterial Properties

The antibacterial properties of GN lysins and GN-peptides were next assessed in human serum. *P. aeruginosa* cells were incubated in human serum for 1 h at 37° C., without agitation, and the activity against exponential phase of PAO1 was examined GN Lysins and GN peptides (at 25 mcg/ml) were each pooled in the presence and absence of a sub-MIC concentration of polymyxin B (PMB) (1 mcg/ml). The threshold of detection was 2.0 log 10 CFU/ml. As shown in FIG. 7, GN lysin pool alone demonstrated antibacterial properties similar to those displayed by Polymxin B. Furthermore, when combined with PMB, both the peptide pool and the lysin pool resulted in a ≥4-log 10 decrease in viability.

Collectively, these findings indicate a strong additive or synergistic activity between PMB and either the lysin polypeptides (GNs) or lysin peptides in human serum. Since prior studies have demonstrated strong antimicrobial activity of individual components of a combined lysin mixture, it is anticipated that in addition to lysin pools, individual lysin components will also exhibit a strong additive or synergistic activity with antibiotics (Loeffler et al. *Antimicrob Agents Chemother.* January; 47(1): 375-377 (2003)).

Prophetic Example 1

Testing of Isolated GN Lysins

In this Example, the goal is to verify that GN lysin polypeptides and peptide derivatives of GN4 described herein are individually capable of inhibiting the growth of or killing Gram-negative bacterial strains in addition to *P. aeruginosa*. To do so, the isolated polypeptides of this disclosure (which may be expressed as described herein and purified by conventional techniques) will be tested for antimicrobial activity against various Gram-negative strains such as *Klebsiella pneumoniae* NCTC 9633 (ATCC 13883), *Enterobacter aerogenes* NCTC 10006 (ATCC 13048), *Citrobacter freundii* NCT 9750 (ATCC 8090), *Salmonella typhimurium* CDC 6516-60 (ATCC 14028), *Yersinia pestis* (ATCC BAA-1511D-5), *Francisella* tulerensis (ATCC 6223) and *Escherichia coli* DSM 1103 (ATCC 25822), all commercially available. In additional arms of this experiment, the strain can be selected to be resistant to one or more standard care antibiotics, such as multi-drug resistant *P. aeruginosa* Br667strain.

Briefly, GN lysin polypeptides and GN4 peptides will be tested at a concentration of 5-15 mcg/ml for 1 hour (at 37° C., without agitation) in the presence of 20 mM Tris-HCl (pH 7.2) buffer. The threshold of detection will be 2.0 Log 10 CFU/ml. The activity of each lysin polypeptide or fragment thereof will be tested alone, or in combination with an antibiotic active against Gram-negative bacteria such as polymyxin B or another antibiotic active against Gram-negative bacteria such as gentamicin. In arms of this experiment wherein the ability of a lysin polypeptide to overcome resistance to an antibiotic is being tested, the selected antibiotic will be one to which the particular bacterium is resistant. A 100 µL aliquot of inoculum will be removed from the culture medium at different time-points (0, 1, 4 and 8 h) for the determination of CFU/mL by the plate count technique.

Based on the conservation of the outer membrane structure of Gram-negative bacteria, and on the effectiveness of GN4 and its foregoing derivatives and other lysins of the present disclosure and Examples against *P. aeruginosa*, it is anticipated that the lysin polypeptides of the present disclosure will exhibit antibacterial activity against additional (other than *P. aeruginosa*) strains of Gram-negative bacteria.

Prophetic Example 2

Testing the Synergistic and Additive Effects Between GN Lysins/Lysin Peptides and Additional Antibiotics Similar to the experimental design described in Example 5, the lysin polypeptides disclosed herein will be tested for synergistic or additive effects when used in combination with additional (other than PMB) antibiotics. The synergistic or additive antibacterial properties of GN lysins and GN-peptides will be assessed in human serum. *P. aeruginosa* will be incubated in human serum for 1 h at 37° C., without agitation, and the activity against exponential phase of PAO1 will be examined GN Lysins and GN peptides (at 10-25 mcg/ml) will each be incubated in the presence and absence of a sub-MIC concentration of an antibiotic such as novobiocin, an aminoglycoside, Carbapenem, Ceftazidime (3rd generation), Cefepime (4th generation), Ceftobiprole (5th generation), a Fluoroquinolone, Piperacillin, Ticarcillin, Colistin, a Rifamycin (such as rifampicin, rifabutin, rifapentin etc.), and a Penicillin. Bacterial viability will be determined in CFU/mL by the plate count technique.

Prophetic Example 3

Testing of Lysin Polypeptides for the Treatment of Multidrug-Resistant *P. aeruginosa* Using In Vivo Model of Pneumonia Adult C57 Black mice will be maintained in a controlled environment in cages in specific pathogen-free conditions. They will be briefly anesthetized with inhaled sevorane (Abbot Laboratories) in an oxygenated chamber and placed in a supine position with their heads elevated. MDR *P. aeruginosa* strain Ka02 bacterial inoculums ($10^6$ cfu's in 50 µl of lactated Ringer's solution) will be instilled slowly into the left lung of each animal using a gavage needle.

Animals will be randomly separated into 3 experimental treatment groups. The 3 groups will consist of the following: 1) Saline-Treated Group (n=5), wherein saline will be administered i.v. 1 hr after infection followed by one further i.p. administration at 5 hr post-infection; 2) Lysin Polypeptide GN4 Group (n=5), wherein GN4 will be administered i.v. 1 hr after infection at a dose of 20 mg/kg followed by one further i.p. administration at 5 hr post-infection at a dose of 15 mg/kg; and 3) Positive control-Imipenem-Treated Group (n=5), wherein "Tienam" (Merck, Sharpe and Dohme)] (active ingredient, imipenem, a carbapenem antibiotic) will be administered i.p. 1 hr after infection at a dose of 25 mg/kg followed by further i.p. administrations at 25 mg/kg at time points of 5 hr, 24 hr, 29 hr, 48 hr and 53 hr following infection.

Survival will be monitored for all three groups every 12 hrs until day 9 post-infection. The same experimental design will be used to test antimicrobial activity in vivo of additional lysin polypeptides disclosed herein.

Prophetic Example 4

Testing of Protection Potential of Lysin Polypeptides Against *Pseudomonas aeruginosa* Induced Sepsis in a Mouse Model of Neutropenia The protective efficacy of the lysin polypeptides against invasive infection with *Pseudomonas aeruginosa* will be measured in the neutropenic mouse model, described previously (Pier et al. *Infect. Immun.* 57:174-179 (1989); Schreiber et al. *J. Immunol.* 146:188-193 (1991)). Adult BALB/c ByJ mice (Jackson Laboratories, Bar Harbor, Me.) will be maintained in a pathogen-free, *pseudomonas*-free environment. Neutropenia will be established by administering 3 mg of cyclophosphamide (Cytoxan®, Bristol-Myers Squibb, Princeton, N.J.) intra-peritoneally to each mouse on days 1, 3, and 5. On day 5, the cyclophosphamide will be administered at time 0 hours, and 2 hours later, lysin (at 20 mg/kg) or PBS control will be administered ip, followed by $10^3$ cfu of live *Pseudomonas aeruginosa* 06ad PA two hours later. Mice will be monitored daily thereafter and mortality will be measured as an outcome. Furthermore, in order to determine optimal lysin concentration for the treatment of animals, additional concentrations of lysin polypeptides will be tested.

The same experimental design will be used to test the protective antimicrobial activity in vivo of additional lysin polypeptides disclosed herein.

Prophetic Example 5

Treatment of Systemic Infection in a Human Subject

A patient diagnosed with systemic respiratory infection due to the multidrug resistant *P. aeruginosa* will be treated with intravenous or aerosolized polymyxin B, in combination with one or more lysin polypeptides disclosed herein.

The recommended dosage of intravenous polymyxin B is 1.5 to 2.5 mg/kg/day (1 mg=10,000 IU) (Sobieszczyk M E et al., *J Antimicrob Chemother.*, 54(2):566-9 (2004)). IV infusions of polymyxin B will be given over 60-90 minutes for 15 days. A pharmaceutical composition comprising one or more lysin polypetides of the present disclosure will be administered intravenously daily at a predetermined concentration. Alternatively, aerosolized polymyxin B therapy will be administered daily (for 14 days) at 2.5 mg/kg/day in combination with a pharmaceutical composition comprising one or more lysin polypetides of the present disclosure. Depending on a clinical status of an individual patient, duration and/or concentration of treatment regiment may vary. Additionally, intravenous or aerosolized polymyxin B can be administered in multiple occurrences during the day. Detailed information regarding the use of intravenous and aerosolized polymyxins is provided, e.g., by Falagas et al. *Clin Med Res.* 4(2): 138-146 (2006)).

At the end of the treatment, patients will be evaluated for microbiological clearance as well as for safety. It is anticipated that treatment of patients affliccted with systemic respiratory infection will lead to reduction of symptoms associated with the infection and/or a decrease or eradication of the causative bacterial population in the patients.

Prophetic Example 6

Topical Treatment of Diabetic Ulcer in a Human Subject

A diabetic foot ulcer infection is one of the severe complications of diabetes mellitus and one of the leading causes of hospitalization among diabetic patients. Importantly, *P. aeruginosa* frequently causes severe tissue damage in diabetic foot ulcers (Sivanmaliappan and Sevanan, *Int J Microbiol.* article ID: 605195 (2011). In order to show efficacy of lysin polypetides of the present disclosure in the treatment of diabetic foot ulcer infection, a clinical study will be conducted.

Initially, a wound culture specimen of an individual patient will be tested for the presence of *P. aeruginosa*. Next, susceptibility of *P. aeruginosa* to one or more lysin polypeptide(s) of the present disclosure (e.g., in a pool) will be confirmed using for example the disc diffusion method according to the Clinical and Laboratory Standards Institute (CLSI) criteria (van der Heijden et al. Ann *Clin Microbiol Antimicrob.* 6:8 (2007)). Alternatively, the patients will be pre-selected to fulfill the microbial susceptibility to lysin criterion. In parallel, the susceptibility of an individual strain to a suitable antibiotic to he used, e.g., polymyxin B will be determined, in vitro (or the patients will be preselected to fulfill the criterion of microbial susceptibility to a specific antibiotic). A susceptible strain, e.g., *P. aeruginosa* ATCC 27853 (susceptible to polymyxin) may be used as quality control (QC). In addition, the susceptibility of *P. aeruginosa* present in a wound culture specimen to a combination therapy comprising both lysin polypeptide(s) and an antibiotic of choice, such as polymyxin B (to exclude the possibility of lysin inhibition by the wound environment—see Example 5 and FIG. 7 and discussion thereof above) will be performed.

Following in vitro susceptibility studies, the inventors will test in vivo efficacy of lysin polypeptides of the present disclosure in the treatment of diabetic ulcer infections. Lysin may be administered by injection, e.g., intravenous or subcutaneous injection or can be applied directly to the wound as a topical formulation. Furthermore, lysin polypeptides will be tested in combination with an antibiotic used for the treatment of diabetic ulcer, wherein the antibiotic may be administered systemically (orally or parenterally) or topically as indicated according to the standard dosage of a specific antibiotic. For example, if polymyxin B is used in combination with lysin polypeptides, the recommended dosage of intravenous polymyxin B is 1.5 to 2.5 mg/kg/day.

Since diabetic foot ulcer infections are commonly polymicrobial, with mixed Gram-positive and Gram-negative species (Citron et al. *J Clin Microbiol*. 45(9): 2819-2828 (2007)), lysin polypeptides of the present disclosure can be used in combination with more than one antibiotic and/or one or more other lysins suitable for the treatment of Gram-positive bacteria present in the foot ulcer infection of a given patient. It is anticipated that lysin treatment will be followed by a high response rate for example in terms of log reduction or eradication of bacterial population or any other clinical or laboratory measure of improvement. The response to a combination of a lysin according to the present disclosure and an antibiotic is anticipated to be even higher as lysins and antibiotics synergize. Indeed it may be possible to reduce the administered amount of one or both of a lysin or an antibiotic without sacrificing effectiveness.

Prophetic Example 7

Topical Treatment of Burn in a Human Subject

Burn wound infections pose significant concerns as they delay healing, promote scarring and may result in bacteremia, sepsis or organ failure. *P. aeruginosa* is the most common source of burn infections (Church et al. *Clinical Microbiology Reviews*, 19 (2), 403-434 (2006)). Because lysin polypeptides of the present disclosure have been shown to be active against *P. aeruginosa*, it is anticipated that they can be used for the treatment of such infections as monotherapy or advantageously in combination without one or more antibiotics.

Topical compositions in a form of cream, gel, and/or foam comprising lysin polypeptides of the present disclosure will be applied on the affected skin area of patients suffering from various degree burns, including I, II, and III degree burns. The topical composition containing lysin polypeptides with or without antibiotics or additional active agents (lysins active against different target organisms and optionally antibiotics addressing these target organisms) will be applied directly to the infected burn area for different time intervals.

Topical application of lysin polypeptides is anticipated to result in the reduction or elimination of patients' symptoms, as well as in the reduction or eradication of the causative bacterial population.

The foregoing Examples are illustrative of the methods and features described herein and are not intended to be limiting. Moreover, they contain statements of general applicability to the present disclosure and such statements are not confined to the particular Example they appear in but constitute conclusions descriptions and expressions of broader implication of the experimental results described herein.

The contents of all cited references are incorporated by reference in their entirety as if fully transcribed herein for all purposes.

```
GN37
Polypeptide sequence
                                            SEQ ID NO: 1
MTYTLSKRSLDNLKGVHPDLVAVVHRAIQLTPVDFAVIEGLRSVSRQKE

LVAAGASKTMNSRHLTGHAVDLAAYVNGIRWDWPLYDAIAVAVKAAAKE

LGVAIVWGGDWTTFKDGPHFELDRSKYR
                                               (SEQ ID NO: 1)

GN2
Polypeptide sequence
                                            SEQ ID NO: 2
MKISLEGLSLIKKFEGCKLEAYKCSAGVWTIGYGHTAGVKEGDVCTQEE

AEKLLRGDIFKFEEYVQDSVKVDLDQSQFDALVAWTFNLGPGNLRSSTM

LKKLNNGEYESVPFEMRRWNKAGGKTLDGLIRRRQAESLLFESKEWHQV
                                               (SEQ ID NO: 2)

GN4
Polypeptide sequence
                                            SEQ ID NO: 3
MRTSQRGIDLIKSFEGLRLSAYQDSVGVWTIGYGTTRGVTRYMTITVEQ

AERMLSNDIQRFEPELDRLAKVPLNQNQWDALMSFVYNLGAANLASSTL

LKLLNKGDYQGAADQFPRWVNAGGKRLDGLVKRRAAERALFLEPLS
                                               (SEQ ID NO: 3)

GN14
Polypeptide sequence
                                            SEQ ID NO: 4
MNNELPWVAEARKYIGLREDTSKTSHNPKLLAMLDRMGEFSNESRAWWH

DDETPWCGLFVGYCLGVAGRYVVREWYRARAWEAPQLTKLDRPAYGALV

TFTRSGGGHVGFIVGKDARGNLMVLGGNQSNAVSIAPFAVSRVTGYFWP

SFWRNKTAVKSVPFEERYSLPLLKSNGELSTNEA
                                               (SEQ ID NO: 4)

GN43
Polypeptide sequence
                                            SEQ ID NO: 5
MKRTTLNLELESNTDRLLQEKDDLLPQSVTNSSDEGTPFAQVEGASDDN

TAEQDSDKPGASVADADTKPVDPEWKTITVASGDTLSTVFTKAGLSTSA

MHDMLTSSKDAKRFTHLKVGQEVKLKLDPKGELQALRVKQSELETIGLD

KTDKGYSFKREKAQIDLHTAYAHGRITSSLFVAGRNAGLPYNLVTSLSN

IFGYDIDFALDLREGDEFDVIYEQHKVNGKQVATGNILAARFVNRGKTY

TAVRYTNKQGNTSYYRADGSSMRKAFIRTPVDFARISSRFSLGRRHPIL

NKIRAHKGVDYAAPIGTPIKATGDGKILEAGRKGGYGNAVVIQHGQRYR

TIYGHMSRFAKGIRAGTSVKQGQIIGYVGMTGLATGPHLHYEFQINGRH

VDPLSAKLPMADPLGGADRKRFMAQTQPMIARMDQEKKTLLALNKQR
                                               (SEQ ID NO: 5)

PGN4
Polypeptide sequence
                                            SEQ ID NO: 6
NKGDYQGAADQFPRWVNAGGKRLDGLVKRRASQSRESQC
                                               (SEQ ID NO: 6)
```

FGN4-1
Polypeptide sequence
SEQ ID NO: 7
NKGDYQGAADQFPRWVNAGGKRLDGLVKRRAAERALFLEPLS
(SEQ ID NO: 7)

FGN4-2
Polypeptide sequence
SEQ ID NO: 8
NKGDYQGAADQFPRWVNAGGKRLDGLVKRRA
(SEQ ID NO: 8)

FGN4-3
Polypeptide sequence
SEQ ID NO: 9
NKGDYQGAADQFPRWVNAGGKRLDGLVKRR<u>K</u>
(SEQ ID NO: 9)

FGN4-4
Polypeptide sequence
SEQ ID NO: 10
NKGDYQGAADQFPRWVNAGGKRLDGLVKRRAAERALFLEPLS<u>C</u>
(SEQ ID NO: 10)

GN37
Polynucleotide sequence
SEQ ID NO: 11
ATGACATACACCCTGAGCAAAAGAAGCCTGGATAACCTAAAAGGCGTTC

ATCCCGATCTGGTTGCCGTTGTCCATCGCGCCATCCAGCTTACACCGGT

TGATTTCGCGGTGATCGAAGGCCTGCGCTCCGTATCCCGCCAAAAGGAA

CTGGTGGCCGCCGGCGCCAGCAAGACCATGAACAGCCGACACCTGACAG

GCCATGCGGTTGATCTAGCCGCTTACGTCAATGGCATCCGCTGGGACTG

GCCCCTGTATGACGCCATCGCCGTGGCTGTGAAAGCCGCAGCAAAGGAA

TTGGGTGTGGCCATCGTGTGGGCGGTGACTGGACCACGTTTAAGGATG

GCCCGCACTTTGAACTGGATCGGAGCAAATACAGATGA
(SEQ ID NO: 11)

GN2
Polynucleotide sequence
SEQ ID NO: 12
ATGAAAATTAGTTTAGAGGGATTATCTCTCATCAAAAAATTTGAGGGTT

GTAAACTAGAAGCATACAAATGTTCTGCAGGAGTGTGGACTATAGGTTA

TGGTCATACTGCAGGTGTAAAAGAAGGTGATGTTTGCACACAAGAGGAA

GCTGAAAAATTATTAAGAGGAGATATCTTTAAATTTGAAGAGTATGTGC

AAGATAGTGTAAAGGTTGATTTAGACCAAAGTCAATTTGACGCATTAGT

TGCATGGACATTTAATTTAGGCCCAGGTAATTTAAGAAGTTCAACCATG

TTGAAAAAATTAAATAATGGAGAGTATGAATCTGTTCCTTTCGAAATGA

GAAGGTGGAATAAAGCAGGTGGTAAAACCTTAGATGGTTTAATCAGAAG

ACGCCAAGCAGAATCATTATTATTTGAAAGTAAAGAGTGGCATCAAGTA

TAA
(SEQ ID NO: 12)

GN4
Polynucleotide sequence
SEQ ID NO: 13
ATGCGTACATCCCAACGAGGCATCGACCTCATCAAATCCTTCGAGGGCC

TGCGCCTGTCCGCTTACCAGGACTCGGTGGGTGTCTGGACCATAGGTTA

CGGCACCACTCGGGGCGTCACCCGCTACATGACGATCACCGTCGAGCAG

GCCGAGCGGATGCTGTCGAACGACATTCAGCGCTTCGAGCCAGAGCTAG

ACAGGCTGGCGAAGGTGCCACTGAACCAGAACCAGTGGGATGCCCTGAT

GAGCTTCGTGTACAACCTGGGCGCGGCCAATCTGGCGTCGTCCACGCTG

CTCAAGCTGCTGAACAAGGGTGACTACCAGGGAGCAGCGGACCAGTTCC

CGCGCTGGGTGAATGCGGGCGGTAAGCGCTTGGATGGTCTGGTTAAGCG

TCGAGCAGCCGAGCGTGCGCTGTTCCTGGAGCCACTATCGTGA
(SEQ ID NO: 13)

GN14
Polynucleotide sequence
SEQ ID NO: 14
ATGAATAACGAACTTCCTTGGGTAGCCGAAGCCCGAAAGTATATCGGCC

TTCGCGAAGACACTTCGAAGACTTCGCATAACCCGAAACTTCTTGCCAT

GCTTGACCGCATGGGCGAATTTTCCAACGAATCCCGCGCTTGGTGGCAC

GACGACGAAACGCCTTGGTGCGGACTGTTCGTCGGCTATTGCTTGGGCG

TTGCCGGGCGCTACGTCGTCCGCGAATGGTACAGGGCGCGGGCATGGGA

AGCCCCGCAGCTTACGAAGCTTGACCGGCCCGCATACGGCGCGCTTGTG

ACCTTCACGCGAAGCGGCGGCGGCCACGTCGGTTTTATTGTGGGCAAGG

ATGCGCGCGGAAATCTTATGGTTCTTGGCGGTAATCAGTCGAACGCCGT

AAGTATCGCACCGTTCGCAGTATCCCGCGTAACCGGCTATTTCTGGCCG

TCGTTCTGGCGAAACAAGACCGCAGTTAAAAGCGTTCCGTTTGAAGAAC

GTTATTCGCTGCCGCTGTTGAAGTCGAACGGCGAACTTTCGACGAATGA

AGCGTAA
(SEQ ID NO: 14)

GN43
Polynucleotide sequences
SEQ ID NO: 15
ATGAATAACGAACTTCCTTGGGTAGCCGAAGCCCGAAAGTATATCGGCC

TTCGCGAAGACACTTCGAAGACTTCGCATAACCCGAAACTTCTTGCCAT

GCTTGACCGCATGGGCGAATTTTCCAACGAATCCCGCGCTTGGTGGCAC

GACGACGAAACGCCTTGGTGCGGACTGTTCGTCGGCTATTGCTTGGGCG

TTGCCGGGCGCTACGTCGTCCGCGAATGGTACAGGGCGCGGGCATGGGA

AGCCCCGCAGCTTACGAAGCTTGACCGGCCCGCATACGGCGCGCTTGTG

ACCTTCACGCGAAGCGGCGGCGGCCACGTCGGTTTTATTGTGGGCAAGG

ATGCGCGCGGAAATCTTATGGTTCTTGGCGGTAATCAGTCGAACGCCGT

AAGTATCGCACCGTTCGCAGTATCCCGCGTAACCGGCTATTTCTGGCCG

TCGTTCTGGCGAAACAAGACCGCAGTTAAAAGCGTTCCGTTTGAAGAAC

GTTATTCGCTGCCGCTGTTGAAGTCGAACGGCGAACTTTCGACGAATGA

AGCGTAA
(SEQ ID NO: 15)

What is claimed is:

1. A method of inhibiting the growth, or reducing the population of, or killing of at least one species of Gram-negative bacteria, the method comprising contacting the bacteria with a composition comprising an effective amount of a lysin polypeptide comprising an amino acid sequence at least 90% identical to a polypeptide sequence selected from the group consisting of SEQ ID NO: 3, SEQ ID NO: 7, and SEQ ID NO: 8, or a fragment thereof having lytic activity, wherein the lysin polypeptide or fragment thereof has the property of inhibiting the growth of, or reducing the initial population of, or killing at least one species of Gram-negative bacteria.

2. A method of treating a bacterial infection caused by one or more species of Gram-negative bacteria, comprising administering to a subject diagnosed with, at risk for, or exhibiting symptoms of a bacterial infection, a composition comprising an effective amount of a lysin polypeptide comprising an amino acid sequence at least 90% identical to a polypeptide sequence selected from the group consisting of SEQ ID NO: 3, SEQ ID NO: 7, and SEQ ID NO: 8, or a fragment thereof having lytic activity, wherein the lysin polypeptide or fragment thereof has the property of inhibiting the growth of, or reducing an initial population of, or killing one or more species of Gram-negative bacteria.

3. The method of claim 2, wherein the Gram-negative bacteria is selected from the group consisting of *Pseudomonas aeruginosa, Klebsiella* spp., *Enterobacter* spp., *Escherichia coli, Citrobacter freundii, Salmonella typhimurium, Yersinia pestis*, and *Franciscella tulerensis*.

4. The method of claim 2, wherein the lysin polypeptide amino acid sequence is at least 95% identical to a sequence selected from the group consisting of SEQ ID NO: 3, SEQ ID NO: 7, and SEQ ID NO: 8, or a fragment thereof having lytic activity.

5. The method of claim 2, wherein the lysin polypeptide amino acid sequence is selected from the group consisting of SEQ ID NO: 3, SEQ ID NO: 7, and SEQ ID NO: 8.

6. The method of claim 2, wherein the Gram-negative bacterial infection is an infection caused by *Pseudomonas aeruginosa*.

7. A method of treating a topical or systemic pathogenic bacterial infection caused by one or more species of Gram-negative bacteria in a subject, comprising administering to a subject a composition containing an effective amount of a lysin polypeptide comprising an amino acid sequence at least 90% identical to polypeptide sequence selected from the group consisting of SEQ ID NO: 3, SEQ ID NO: 7, and SEQ ID NO: 8, or a fragment thereof having lytic activity, wherein the polypeptide or fragment thereof has the property of inhibiting the growth of, or reducing an initial population of, or killing one or more species of Gram-negative bacteria.

8. A method of preventing or treating a Gram-negative bacterial infection comprising co-administering to a subject diagnosed with, at risk for, or exhibiting symptoms of a Gram-negative bacterial infection, a combination of a first effective amount of a composition comprising an effective amount of lysin polypeptide comprising amino acid sequence at least 90% identical to a polypeptide sequence selected from the group consisting of SEQ ID NO: 3, SEQ ID NO: 7, and SEQ ID NO: 8, or fragments thereof having lytic activity, and a second effective amount of an antibiotic suitable for the treatment of Gram-negative bacterial infection.

9. The method of claim 8, wherein the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

10. A method for augmenting the efficacy of an antibiotic suitable for the treatment of Gram-negative bacterial infection, comprising co-administering the antibiotic in combination with one or more lysin polypeptides comprising an amino acid sequence at least 90% identical to a polypeptide sequence selected from the group consisting of SEQ ID NO: 3, SEQ ID NO: 7, and SEQ ID NO: 8, or a fragment thereof having lytic activity, wherein administration of the combination is more effective in inhibiting the growth of, or reducing an initial population of, or killing the Gram-negative bacteria than administration of either the antibiotic or the lysin polypeptide or fragment thereof individually.

11. The method of claim 10, wherein the lysin polypeptide amino acid sequence is at least 95% identical to a sequence selected from the group consisting of SEQ ID NO: 3, SEQ ID NO: 7, and SEQ ID NO: 8, or a fragment thereof having lytic activity.

12. The method of claim 10, wherein the lysin polypeptide amino acid sequence is selected from the group consisting of SEQ ID NO: 3, SEQ ID NO: 7, and SEQ ID NO: 8.

13. The method of claim 10, wherein the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

\* \* \* \* \*

SEQUENCE LISTING

<160> NUMBER OF SEQ ID NOS: 21

<210> SEQ ID NO 1
<211> LENGTH: 126
<212> TYPE: PRT
<213> ORGANISM: Micavibrio aeruginosavorus

<400> SEQUENCE: 1

Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
    50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg
        115                 120                 125

<210> SEQ ID NO 2
<211> LENGTH: 147
<212> TYPE: PRT
<213> ORGANISM: Unknown
<220> FEATURE:
<223> OTHER INFORMATION: hypothetical protein GOS_817346 [marine
      metagenome] (GenBank: EDG23390.1)

<400> SEQUENCE: 2

Met Lys Ile Ser Leu Glu Gly Leu Ser Leu Ile Lys Lys Phe Glu Gly
1               5                   10                  15

Cys Lys Leu Glu Ala Tyr Lys Cys Ser Ala Gly Val Trp Thr Ile Gly
            20                  25                  30

Tyr Gly His Thr Ala Gly Val Lys Glu Gly Asp Val Cys Thr Gln Glu
        35                  40                  45

Glu Ala Glu Lys Leu Leu Arg Gly Asp Ile Phe Lys Phe Glu Glu Tyr
    50                  55                  60

Val Gln Asp Ser Val Lys Val Asp Leu Asp Gln Ser Gln Phe Asp Ala
65                  70                  75                  80

Leu Val Ala Trp Thr Phe Asn Leu Gly Pro Gly Asn Leu Arg Ser Ser
                85                  90                  95

Thr Met Leu Lys Lys Leu Asn Asn Gly Glu Tyr Glu Ser Val Pro Phe
            100                 105                 110

Glu Met Arg Arg Trp Asn Lys Ala Gly Gly Lys Thr Leu Asp Gly Leu
        115                 120                 125

Ile Arg Arg Gln Ala Glu Ser Leu Leu Phe Glu Ser Lys Glu Trp
    130                 135                 140

His Gln Val
145

<210> SEQ ID NO 3
<211> LENGTH: 144
<212> TYPE: PRT

<213> ORGANISM: Pseudomonas phage PAJU2

<400> SEQUENCE: 3

Met Arg Thr Ser Gln Arg Gly Ile Asp Leu Ile Lys Ser Phe Glu Gly
1               5                   10                  15

Leu Arg Leu Ser Ala Tyr Gln Asp Ser Val Gly Val Trp Thr Ile Gly
            20                  25                  30

Tyr Gly Thr Thr Arg Gly Val Thr Arg Tyr Met Thr Ile Thr Val Glu
        35                  40                  45

Gln Ala Glu Arg Met Leu Ser Asn Asp Ile Gln Arg Phe Glu Pro Glu
    50                  55                  60

Leu Asp Arg Leu Ala Lys Val Pro Leu Asn Gln Asn Gln Trp Asp Ala
65                  70                  75                  80

Leu Met Ser Phe Val Tyr Asn Leu Gly Ala Ala Asn Leu Ala Ser Ser
                85                  90                  95

Thr Leu Leu Lys Leu Leu Asn Lys Gly Asp Tyr Gln Gly Ala Ala Asp
            100                 105                 110

Gln Phe Pro Arg Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
    130                 135                 140

<210> SEQ ID NO 4
<211> LENGTH: 181
<212> TYPE: PRT
<213> ORGANISM: Pseudomonas phage Lu11

<400> SEQUENCE: 4

Met Asn Asn Glu Leu Pro Trp Val Ala Glu Ala Arg Lys Tyr Ile Gly
1               5                   10                  15

Leu Arg Glu Asp Thr Ser Lys Thr Ser His Asn Pro Lys Leu Leu Ala
            20                  25                  30

Met Leu Asp Arg Met Gly Glu Phe Ser Asn Glu Ser Arg Ala Trp Trp
        35                  40                  45

His Asp Asp Glu Thr Pro Trp Cys Gly Leu Phe Val Gly Tyr Cys Leu
    50                  55                  60

Gly Val Ala Gly Arg Tyr Val Arg Glu Trp Tyr Arg Ala Arg Ala
65                  70                  75                  80

Trp Glu Ala Pro Gln Leu Thr Lys Leu Asp Arg Pro Ala Tyr Gly Ala
                85                  90                  95

Leu Val Thr Phe Thr Arg Ser Gly Gly His Val Gly Phe Ile Val
            100                 105                 110

Gly Lys Asp Ala Arg Gly Asn Leu Met Val Leu Gly Gly Asn Gln Ser
        115                 120                 125

Asn Ala Val Ser Ile Ala Pro Phe Ala Val Ser Arg Val Thr Gly Tyr
    130                 135                 140

Phe Trp Pro Ser Phe Trp Arg Asn Lys Thr Ala Val Lys Ser Val Pro
145                 150                 155                 160

Phe Glu Glu Arg Tyr Ser Leu Pro Leu Leu Lys Ser Asn Gly Glu Leu
                165                 170                 175

Ser Thr Asn Glu Ala
            180

<210> SEQ ID NO 5
<211> LENGTH: 439
<212> TYPE: PRT

<213> ORGANISM: Pseudomonas sp.

<400> SEQUENCE: 5

```
Met Lys Arg Thr Thr Leu Asn Leu Glu Leu Glu Ser Asn Thr Asp Arg
1               5                   10                  15

Leu Leu Gln Glu Lys Asp Asp Leu Leu Pro Gln Ser Val Thr Asn Ser
            20                  25                  30

Ser Asp Glu Gly Thr Pro Phe Ala Gln Val Glu Gly Ala Ser Asp Asp
        35                  40                  45

Asn Thr Ala Glu Gln Asp Ser Asp Lys Pro Gly Ala Ser Val Ala Asp
    50                  55                  60

Ala Asp Thr Lys Pro Val Asp Pro Glu Trp Lys Thr Ile Thr Val Ala
65                  70                  75                  80

Ser Gly Asp Thr Leu Ser Thr Val Phe Thr Lys Ala Gly Leu Ser Thr
                85                  90                  95

Ser Ala Met His Asp Met Leu Thr Ser Ser Lys Asp Ala Lys Arg Phe
            100                 105                 110

Thr His Leu Lys Val Gly Gln Glu Val Lys Leu Lys Leu Asp Pro Lys
        115                 120                 125

Gly Glu Leu Gln Ala Leu Arg Val Lys Gln Ser Glu Leu Glu Thr Ile
    130                 135                 140

Gly Leu Asp Lys Thr Asp Lys Gly Tyr Ser Phe Lys Arg Glu Lys Ala
145                 150                 155                 160

Gln Ile Asp Leu His Thr Ala Tyr Ala His Gly Arg Ile Thr Ser Ser
                165                 170                 175

Leu Phe Val Ala Gly Arg Asn Ala Gly Leu Pro Tyr Asn Leu Val Thr
            180                 185                 190

Ser Leu Ser Asn Ile Phe Gly Tyr Asp Ile Asp Phe Ala Leu Asp Leu
        195                 200                 205

Arg Glu Gly Asp Glu Phe Asp Val Ile Tyr Glu Gln His Lys Val Asn
    210                 215                 220

Gly Lys Gln Val Ala Thr Gly Asn Ile Leu Ala Ala Arg Phe Val Asn
225                 230                 235                 240

Arg Gly Lys Thr Tyr Thr Ala Val Arg Tyr Thr Asn Lys Gln Gly Asn
                245                 250                 255

Thr Ser Tyr Tyr Arg Ala Asp Gly Ser Ser Met Arg Lys Ala Phe Ile
            260                 265                 270

Arg Thr Pro Val Asp Phe Ala Arg Ile Ser Ser Arg Phe Ser Leu Gly
        275                 280                 285

Arg Arg His Pro Ile Leu Asn Lys Ile Arg Ala His Lys Gly Val Asp
    290                 295                 300

Tyr Ala Ala Pro Ile Gly Thr Pro Ile Lys Ala Thr Gly Asp Gly Lys
305                 310                 315                 320

Ile Leu Glu Ala Gly Arg Lys Gly Gly Tyr Gly Asn Ala Val Val Ile
                325                 330                 335

Gln His Gly Gln Arg Tyr Arg Thr Ile Tyr Gly His Met Ser Arg Phe
            340                 345                 350

Ala Lys Gly Ile Arg Ala Gly Thr Ser Val Lys Gln Gly Gln Ile Ile
        355                 360                 365

Gly Tyr Val Gly Met Thr Gly Leu Ala Thr Gly Pro His Leu His Tyr
    370                 375                 380

Glu Phe Gln Ile Asn Gly Arg His Val Asp Pro Leu Ser Ala Lys Leu
385                 390                 395                 400
```

```
Pro Met Ala Asp Pro Leu Gly Gly Ala Asp Arg Lys Arg Phe Met Ala
            405                 410                 415

Gln Thr Gln Pro Met Ile Ala Arg Met Asp Gln Glu Lys Lys Thr Leu
        420                 425                 430

Leu Ala Leu Asn Lys Gln Arg
        435

<210> SEQ ID NO 6
<211> LENGTH: 39
<212> TYPE: PRT
<213> ORGANISM: Artificial Sequence
<220> FEATURE:
<223> OTHER INFORMATION: artificially-created modified fragment of GN4
      (SEQ ID NO: 3)

<400> SEQUENCE: 6

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Ala Ser
            20                  25                  30

Gln Ser Arg Glu Ser Gln Cys
        35

<210> SEQ ID NO 7
<211> LENGTH: 42
<212> TYPE: PRT
<213> ORGANISM: Pseudomonas phage PAJU2

<400> SEQUENCE: 7

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Ala Ala
            20                  25                  30

Glu Arg Ala Leu Phe Leu Glu Pro Leu Ser
        35                  40

<210> SEQ ID NO 8
<211> LENGTH: 31
<212> TYPE: PRT
<213> ORGANISM: Pseudomonas phage PAJU2

<400> SEQUENCE: 8

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Ala
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: artificially-created modified fragment of GN4
      (SEQ ID NO: 3)

<400> SEQUENCE: 9

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Lys
            20                  25                  30

<210> SEQ ID NO 10
```

<211> LENGTH: 43
<212> TYPE: PRT
<213> ORGANISM: Artificial Sequence
<220> FEATURE:
<223> OTHER INFORMATION: artificially-created modified fragment of GN4 (SEQ ID NO: 3)

<400> SEQUENCE: 10

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Ala Ala
            20                  25                  30

Glu Arg Ala Leu Phe Leu Glu Pro Leu Ser Cys
        35                  40

<210> SEQ ID NO 11
<211> LENGTH: 381
<212> TYPE: DNA
<213> ORGANISM: Micavibrio aeruginosavorus

<400> SEQUENCE: 11
atgacataca ccctgagcaa agaagcctg gataacctaa aaggcgttca tcccgatctg      60
gttgccgttg tccatcgcgc catccagctt acaccggttg atttcgcggt gatcgaaggc     120
ctgcgctccg tatcccgcca aaaggaactg gtggccgccg cgccagcaa gaccatgaac     180 agccgacacc tgacaggcca tgcggttgat ctagccgctt acgtcaatgg catccgctgg     240
gactggcccc tgtatgacgc catcgccgtg gctgtgaaag ccgcagcaaa ggaattgggt     300
gtggccatcg tgtggggcgg tgactggacc acgtttaagg atggcccgca ctttgaactg     360
gatcggagca aatacagatg a                                              381

<210> SEQ ID NO 12
<211> LENGTH: 444
<212> TYPE: DNA
<213> ORGANISM: Unknown
<220> FEATURE:
<223> OTHER INFORMATION: Marine metagenome; polynucleotide sequence for the polypeptide of SEQ ID NO: 2

<400> SEQUENCE: 12
atgaaaatta gtttagaggg attatctctc atcaaaaaat ttgagggttg taaactagaa     60
gcatacaaat gttctgcagg agtgtggact ataggttatg gtcatactgc aggtgtaaaa    120
gaaggtgatg tttgcacaca agaggaagct gaaaaattat aagaggaga tatctttaaa    180 tttgaagagt atgtgcaaga tagtgtaaag gttgatttag accaaagtca atttgacgca   240
ttagttgcat ggacatttaa tttaggccca ggtaatttaa gaagttcaac catgttgaaa   300
aaattaaata tggagagta tgaatctgtt cctttcgaaa tgagaaggtg gaataaagca   360
ggtggtaaaa ccttagatgg tttaatcaga agacgccaag cagaatcatt attatttgaa  420
agtaaagagt ggcatcaagt ataa                                         444

<210> SEQ ID NO 13
<211> LENGTH: 435
<212> TYPE: DNA
<213> ORGANISM: Pseudomonas phage PAJU2

<400> SEQUENCE: 13
atgcgtacat cccaacgagg catcgacctc atcaaatcct tcgagggcct gcgcctgtcc     60
gcttaccagg actcggtggg tgtctggacc ataggttacg gcaccactcg gggcgtcacc    120

```
cgctacatga cgatcaccgt cgagcaggcc gagcggatgc tgtcgaacga cattcagcgc    180
ttcgagccag agctagacag gctggcgaag gtgccactga accagaacca gtgggatgcc    240
ctgatgagct tcgtgtacaa cctgggcgcg gccaatctgg cgtcgtccac gctgctcaag    300
ctgctgaaca agggtgacta ccagggagca gcggaccagt tcccgcgctg ggtgaatgcg    360
ggcggtaagc gcttggatgg tctggttaag cgtcgagcag ccgagcgtgc gctgttcctg    420
gagccactat cgtga                                                     435
```

```
<210> SEQ ID NO 14
<211> LENGTH: 546
<212> TYPE: DNA
<213> ORGANISM: Pseudomonas phage Lu11

<400> SEQUENCE: 14
atgaataacg aacttccttg ggtagccgaa gcccgaaagt atatcggcct tcgcgaagac     60
acttcgaaga cttcgcataa cccgaaactt cttgccatgc ttgaccgcat gggcgaattt    120
tccaacgaat cccgcgcttg gtggcacgac gacgaaacgc cttggtgcgg actgttcgtc    180
ggctattgct tgggcgttgc cgggcgctac gtcgtccgcg aatggtacag ggcgcgggca    240
tgggaagccc cgcagcttac gaagcttgac cggcccgcat acggcgcgct tgtgaccttc    300
acgcgaagcg gcggcggcca cgtcggtttt attgtgggca aggatgcgcg cggaaatctt    360
atggttcttg gcggtaatca gtcgaacgcc gtaagtatcg caccgttcgc agtatcccgc    420
gtaaccggct atttctggcc gtcgttctgg cgaaacaaga ccgcagttaa aagcgttccg    480
tttgaagaac gttattcgct gccgctgttg aagtcgaacg gcgaactttc gacgaatgaa    540
gcgtaa                                                              546
```

```
<210> SEQ ID NO 15
<211> LENGTH: 546
<212> TYPE: DNA
<213> ORGANISM: Pseudomonas sp.

<400> SEQUENCE: 15
atgaataacg aacttccttg ggtagccgaa gcccgaaagt atatcggcct tcgcgaagac     60
acttcgaaga cttcgcataa cccgaaactt cttgccatgc ttgaccgcat gggcgaattt    120
tccaacgaat cccgcgcttg gtggcacgac gacgaaacgc cttggtgcgg actgttcgtc    180
ggctattgct tgggcgttgc cgggcgctac gtcgtccgcg aatggtacag ggcgcgggca    240
tgggaagccc cgcagcttac gaagcttgac cggcccgcat acggcgcgct tgtgaccttc    300
acgcgaagcg gcggcggcca cgtcggtttt attgtgggca aggatgcgcg cggaaatctt    360
atggttcttg gcggtaatca gtcgaacgcc gtaagtatcg caccgttcgc agtatcccgc    420
gtaaccggct atttctggcc gtcgttctgg cgaaacaaga ccgcagttaa aagcgttccg    480
tttgaagaac gttattcgct gccgctgttg aagtcgaacg gcgaactttc gacgaatgaa    540
gcgtaa                                                              546
```

```
<210> SEQ ID NO 16
<211> LENGTH: 8
<212> TYPE: PRT
<213> ORGANISM: Hepatitis B virus

<400> SEQUENCE: 16

Ser Gln Ser Arg Glu Ser Gln Cys
1               5
```

<210> SEQ ID NO 17
<211> LENGTH: 1320
<212> TYPE: DNA
<213> ORGANISM: Pseudomonas sp.

<400> SEQUENCE: 17

| | | | | | |
|---|---|---|---|---|---|
| atgaagagga | ccacgctcaa | tctggagctt | gaaagcaaca | ccgatcgcct | ccttcaggag | 60 |
| aaagacgacc | tcctgccgca | atcggtcacc | aattccagcg | acgaaggcac | gccttcgct | 120 |
| caggtagaag | gcgcctccga | cgacaacacc | gccgagcaag | actcggacaa | gccgggcgca | 180 |
| tctgtagccg | atgccgacac | caagcccgtc | gatcccgagt | ggaagaccat | caccgtcgcc | 240 |
| agtggcgata | cgctgtcgac | cgtattcacc | aaggcaggcc | tttccacctc | ggccatgcac | 300 |
| gacatgctga | ccagcagcaa | ggatgccaag | cgcttcaccc | atctgaaggt | cggccaggag | 360 |
| gtcaagctca | agctcgaccc | caaggagag | ctgcaggcac | tgcgagtcaa | gcagagcgaa | 420 |
| ctcgagacca | tcggcctgga | caagaccgac | aagggctact | ccttcaaacg | cgagaaggcc | 480 |
| cagatcgacc | tgcataccgc | ctatgcccat | ggccgcatca | ccagctcgct | gttcgttgcc | 540 |
| ggtcgtaacg | ccggcctgcc | ctataacctg | gtcacgtcgc | tgtcgaacat | cttcggctac | 600 |
| gacatcgact | tcgccctcga | tctgcgtgaa | ggcgacgagt | tcgacgtgat | ctacgaacaa | 660 |
| cacaaggtca | acggcaagca | agtggcgacc | ggcaatatcc | tcgccgcccg | cttcgtcaac | 720 |
| cgtggcaaga | cctacaccgc | cgtgcgctat | accaacaagc | agggcaatac | cagctactac | 780 |
| cgcgccgacg | gctccagcat | gcgcaaggca | ttcatccgta | cgccggtgga | tttcgcccgt | 840 |
| atcagctcgc | gcttctccct | gggccgccgc | cacccgatcc | tgaacaagat | ccgcgcacac | 900 |
| aagggcgtcg | actacgcagc | ccccatcggc | acaccgatca | aggccaccgg | agacggcaag | 960 |
| atcctcgaag | ccggacgcaa | ggggggctac | ggcaacgccg | tggtgatcca | gcacggccag | 1020 |
| cgctatcgga | ccatctacgg | acacatgagc | cgcttcgcca | agggtatccg | cgccggtacc | 1080 |
| agcgtgaagc | agggccagat | catcggttac | gtaggcatga | cgggcctggc | caccggcccg | 1140 |
| cacctgcact | acgagttcca | gatcaatggc | cgtcacgtcg | atccgctgag | cgccaagctg | 1200 |
| cccatggcgg | acccgctcgg | tggcgcagat | cgcaagcgct | tcatggcgca | gacccagccg | 1260 |
| atgatcgcgc | gcatggatca | ggagaagaaa | accctcctgg | ccctgaacaa | gcagcgctga | 1320 |

<210> SEQ ID NO 18
<211> LENGTH: 127
<212> TYPE: PRT
<213> ORGANISM: Streptomyces sp. 212

<400> SEQUENCE: 18

Met Ser Phe Gly Leu Ser Gln Arg Ser Arg Glu Arg Leu Lys Gly Val
1               5                   10                  15

His Pro Asp Leu Val Ala Val Glu Ala Ala Ile Arg Leu Thr Pro
            20                  25                  30

Val Asp Phe Met Ile Thr Glu Gly Leu Arg Thr Pro Ala Arg Gln Ala
            35                  40                  45

Glu Leu Val Arg Ala Gly Ala Ser Arg Thr Leu Asn Ser Arg His Leu
        50                  55                  60

Thr Gly His Ala Val Asp Val Ala Ala Trp Ile Asp Gly Glu Val Arg
65                  70                  75                  80

Trp Asp Trp Pro Leu Tyr Pro Arg Ile Ala Glu Ala Phe Lys Ala Ala
                85                  90                  95

Ala Lys Asp Arg Asp Val Ala Leu Ile Trp Gly Gly Asp Trp Pro Arg
                100                 105                 110

Leu Arg Asp Gly Pro His Phe Glu Leu Asp Arg Arg Gly Tyr Pro
            115                 120                 125

<210> SEQ ID NO 19
<211> LENGTH: 125
<212> TYPE: PRT
<213> ORGANISM: Escherichia coli

<400> SEQUENCE: 19

Met Pro Gly Lys Phe Arg Phe Ser Arg Ser Glu Lys Asn Leu Glu
1               5                   10                  15

Gly Val Lys Pro Gln Leu Val Ala Val Val Arg Arg Ala Leu Glu Leu
            20                  25                  30

Thr Glu Val Asp Phe Gly Ile Thr Glu Gly Leu Arg Ser Lys Tyr Arg
        35                  40                  45

Gln Lys Gln Leu Val Ala Ala Gly Lys Ser Gln Thr Met Asn Ser Arg
    50                  55                  60

His Leu Thr Gly Asp Ala Val Asp Val Val Ala Tyr Ile Gly Ser Gln
65                  70                  75                  80

Val Ser Trp Asp Trp Pro Leu Tyr Glu Lys Ile Ala Gln Ala Phe Lys
                85                  90                  95

Gln Ala Ala Ala Glu Leu Gly Thr Ala Ile Glu Trp Gly Gly Asp Trp
                100                 105                 110

Lys Thr Leu Lys Asp Gly Pro His Phe Gln Leu Lys Arg
            115                 120                 125

<210> SEQ ID NO 20
<211> LENGTH: 125
<212> TYPE: PRT
<213> ORGANISM: Enterobacteria phage phiP27

<400> SEQUENCE: 20

Met Ser Gly Lys Phe Arg Phe Ser Arg Ser Glu Lys Asn Leu Glu
1               5                   10                  15

Gly Val Lys Pro Gln Leu Val Ala Val Val Arg Arg Ala Leu Glu Leu
            20                  25                  30

Thr Glu Val Asp Phe Gly Ile Thr Glu Gly Leu Arg Thr Lys Glu Arg
        35                  40                  45

Gln Lys Gln Leu Val Ala Glu Gly Lys Ser Gln Thr Met Asn Ser Arg
    50                  55                  60

His Leu Thr Gly Asp Ala Val Asp Val Val Ala Tyr Ile Gly Ser Gln
65                  70                  75                  80

Val Ser Trp Asp Trp Pro Leu Tyr Glu Lys Ile Ala Gln Ala Phe Lys
                85                  90                  95

Gln Ala Ala Ala Glu Leu Gly Thr Ala Ile Glu Trp Gly Gly Asp Trp
                100                 105                 110

Lys Thr Leu Lys Asp Gly Pro His Phe Gln Leu Lys Trp
            115                 120                 125

<210> SEQ ID NO 21
<211> LENGTH: 138
<212> TYPE: PRT
<213> ORGANISM: Yersinia phage PY100

-continued

```
<400> SEQUENCE: 21

Met Glu Val Gln Pro Thr Ile Glu Glu Val Ser Met Gly Phe Lys Leu
1               5                   10                  15

Gly Ser Arg Ser Leu Gln Arg Leu Gln Gly Val His Pro Asp Leu Val
            20                  25                  30

Lys Val Val Lys Arg Ala Ile Glu Ile Ser Pro Val Asp Phe Thr Val
        35                  40                  45

Thr Glu Gly Leu Arg Thr Leu Glu Arg Gln Lys Glu Leu Phe Ala Lys
    50                  55                  60

Gly Ala Ser Lys Thr Met Arg Ser Arg His Leu Thr Gly His Ala Val
65              70                  75                  80

Asp Ile Ser Pro Leu Val Asp Gly Lys Val Ser Trp Asp Trp Lys Tyr
            85                  90                  95

Tyr Tyr Pro Met Ala Asp Ala Met Lys Gln Ala Ala Lys Glu Leu Asn
            100                 105                 110

Ile Pro Val Glu Trp Gly Gly Asp Trp Lys Thr Phe Lys Asp Gly Pro
        115                 120                 125

His Phe Gln Leu Pro Tyr Gly Val Tyr Lys
    130                 135
```